(12) United States Patent
Wu et al.

(10) Patent No.: US 12,403,019 B2
(45) Date of Patent: Sep. 2, 2025

(54) SYSTEMS AND METHODS FOR SURGICAL REGISTRATION

(71) Applicant: MAKO Surgical Corp., Weston, FL (US)

(72) Inventors: Zhu Wu, Weston, FL (US); Matthew Thompson, Fort Lauderdale, FL (US); Brent Mittelstadt, Fort Lauderdale, FL (US); Jamil Elbanna, Fort Lauderdale, FL (US)

(73) Assignee: MAKO Surgical Corp.

( * ) Notice: Subject to any disclaimer, the term of this patent is extended or adjusted under 35 U.S.C. 154(b) by 60 days.

(21) Appl. No.: 18/380,488

(22) Filed: Oct. 16, 2023

(65) Prior Publication Data

US 2024/0041613 A1 Feb. 8, 2024

Related U.S. Application Data

(63) Continuation of application No. 16/810,283, filed on Mar. 5, 2020, now Pat. No. 11,839,551.

(Continued)

(51) Int. Cl.
*A61F 2/46* (2006.01)
*A61B 34/10* (2016.01)
(Continued)

(52) U.S. Cl.
CPC .............. *A61F 2/46* (2013.01); *A61B 34/10* (2016.02); *A61F 2/32* (2013.01); *A61F 2/4607* (2013.01);
(Continued)

(58) Field of Classification Search
CPC .. A61F 2/46; A61F 2/32; A61F 2/4607; A61F 2002/30943; A61F 2002/4633;
(Continued)

(56) References Cited

U.S. PATENT DOCUMENTS

| 5,806,518 A | 9/1998 | Mittelstadt |
| 11,071,594 B2 | 7/2021 | Kostrzewski et al. |

(Continued)

FOREIGN PATENT DOCUMENTS

| JP | 2018-158104 A | 10/2018 |
| WO | WO 2018/013848 A1 | 1/2018 |

(Continued)

OTHER PUBLICATIONS

Australian Examination Report, AU 2020232318, dated May 10, 2022, 5 pgs.

(Continued)

*Primary Examiner* — Joel Lamprecht
(74) *Attorney, Agent, or Firm* — Polsinelli PC

(57) ABSTRACT

A system for surgical registration. The system may include at least one computing device in communication with a surgical navigation system and the surgical device. The at least one computing device: a) receiving external bone registration data corresponding to locations on the exterior surface of the femur; b) calculating a first registration transform based on the external bone registration data; c) transforming a first bone removal plan of a surgical plan to the operative coordinate system based on the first registration transform; d) receiving internal bone canal registration data corresponding to at least one of location or orientation data from the inner canal of the femur; e) calculating a second registration transform based on both of the external and internal bone canal bone registration data; and f) transforming a second bone removal plan of the surgical plan to the operative coordinate system based on the second registration transform.

17 Claims, 29 Drawing Sheets

Related U.S. Application Data

(60) Provisional application No. 62/814,057, filed on Mar. 5, 2019.

(51) Int. Cl.
 *A61F 2/32* (2006.01)
 *A61B 34/20* (2016.01)
 *A61F 2/30* (2006.01)

(52) U.S. Cl.
 CPC ... *A61B 2034/102* (2016.02); *A61B 2034/105* (2016.02); *A61B 2034/2068* (2016.02); *A61F 2002/30943* (2013.01); *A61F 2002/4633* (2013.01); *A61F 2002/4667* (2013.01)

(58) Field of Classification Search
 CPC ...... A61F 2002/4667; A61F 2002/4632; A61F 2/461; A61B 34/10; A61B 2034/102; A61B 2034/105; A61B 2034/2068; A61B 17/3403; A61B 2017/3411; A61B 34/74; A61B 34/76; A61B 90/50; A61B 2034/108; A61B 2034/2048; A61B 2034/2051; A61B 2034/2055; A61B 2034/2059; A61B 2034/252; A61B 2034/254; A61B 2090/3916; A61B 2090/3983; A61B 34/20; A61B 34/30; A61B 34/25; A61B 17/162; A61B 17/1659; A61B 17/1675; A61B 17/1735; A61B 17/1764; A61B 2034/107; A61B 2034/2065; A61B 17/175; G16H 20/40; G16H 50/50

See application file for complete search history.

(56) References Cited

U.S. PATENT DOCUMENTS

| | | |
|---|---|---|
| 2008/0010706 A1 | 1/2008 | Moses et al. |
| 2013/0169423 A1 | 7/2013 | Iorgulescu et al. |
| 2015/0328004 A1 | 11/2015 | Mofhouz |
| 2016/0157751 A1 | 6/2016 | Mahfouz |
| 2017/0258526 A1 | 9/2017 | Lang |
| 2018/0021097 A1 | 1/2018 | Quaid et al. |

FOREIGN PATENT DOCUMENTS

| | | |
|---|---|---|
| WO | WO 2018/045086 A1 | 3/2018 |
| WO | WO 2018/231775 A1 | 12/2018 |

OTHER PUBLICATIONS

EP Search Report, EP 20766825.2, dated Oct. 26, 2022, 10 pgs.
International Search Report and Written Opinion, PCT/US2020/021173, dated Jul. 8, 2020, 19 pgs.
Japanese Office Action, JP 2023-079394, dated Jan. 16, 2024, 5 pgs. (English translation).
Extended European Search Report, EP application No. 25174882.8, dated Jul. 21, 2025, 12 pages.

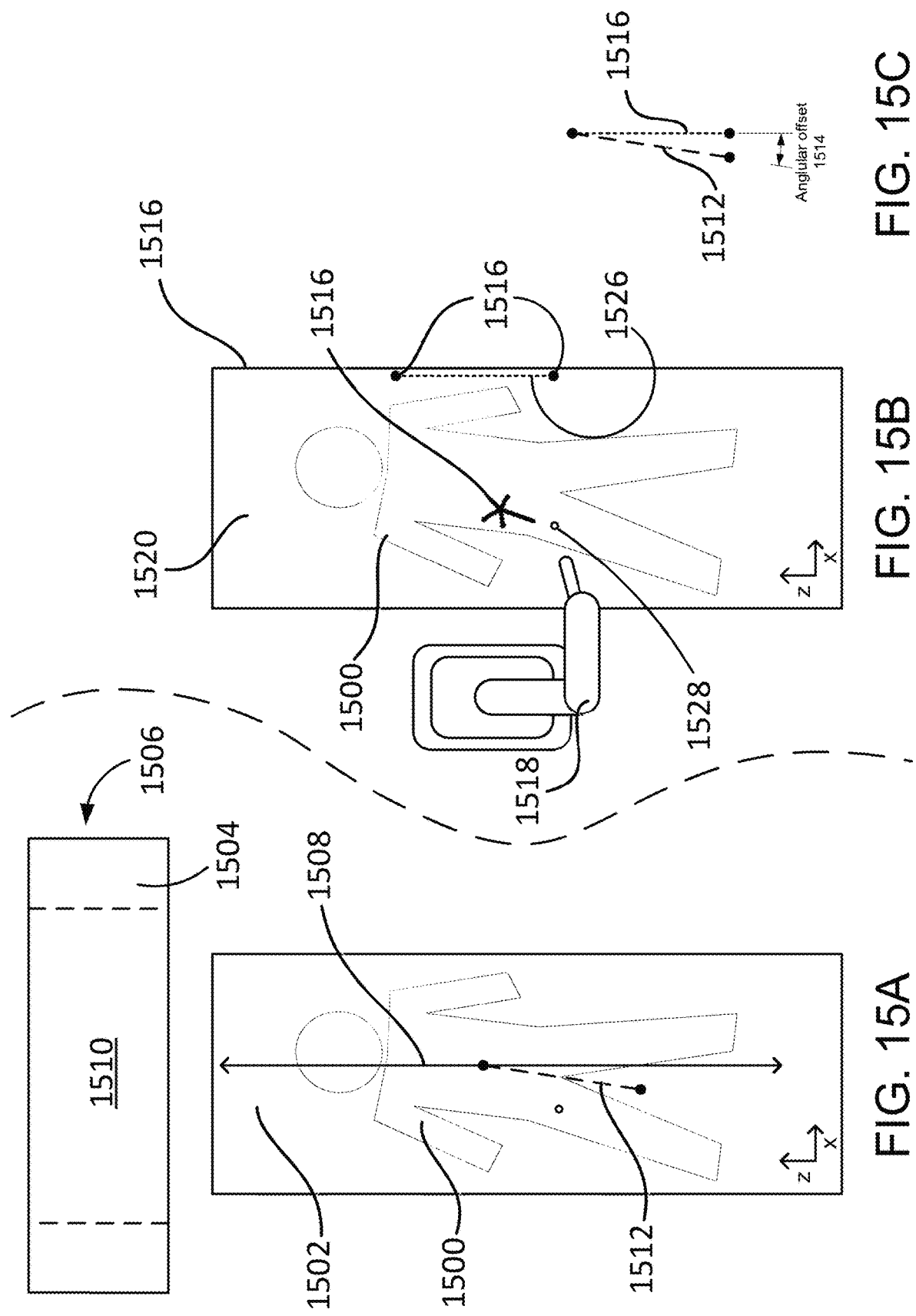

SYSTEMS AND METHODS FOR SURGICAL REGISTRATION

CROSS-REFERENCE TO RELATED APPLICATIONS

This application is a continuation of U.S. patent application Ser. No. 16/810,283, filed Mar. 5, 2020, which application claims the benefit of U.S. Provisional Application No. 62/814,057, filed Mar. 5, 2019. Each application referenced above is hereby incorporated by reference in its entirety into the present application.

TECHNICAL FIELD

The present disclosure relates generally to surgical systems for orthopedic joint replacement surgery and, more particularly, to methods of surgical registration.

BACKGROUND

Robotic systems are often used in applications that require a high degree of accuracy and/or precision, such as surgical procedures or other complex tasks. Such systems may include various types of robots, such as autonomous, tele-operated, and interactive.

Interactive robotic systems may be preferred for some types of surgery, such as joint replacement surgery, because they enable a surgeon to maintain direct, hands-on control of the surgical procedure while still achieving a high degree of accuracy and/or precision. For example, in knee replacement surgery, a surgeon can use an interactive, haptically guided robotic arm in a passive manner to sculpt bone to receive a joint implant, such as a knee implant. To sculpt bone, the surgeon manually grasps and manipulates the robotic arm to move a cutting tool (e.g., a rotating burr) that is coupled to the robotic arm to cut a pocket in the bone. As long as the surgeon maintains a tip of the burr within a predefined virtual cutting boundary or haptic boundary defined, for example, by a haptic object, the robotic arm moves freely with low friction and low inertia such that the surgeon perceives the robotic arm as essentially weightless and can move the robotic arm as desired. If the surgeon attempts to move the tip of the burr to cut outside the virtual cutting boundary, however, the robotic arm provides haptic feedback (e.g., forced resistance) that prevents or inhibits the surgeon from moving the tip of the burr beyond the virtual cutting boundary. In this manner, the robotic arm enables highly accurate, repeatable bone cuts. When the surgeon manually implants a knee implant (e.g., a patellofemoral component) on a corresponding bone cut the implant will generally be accurately aligned due to the configuration of and interface between the cut bone and the knee implant.

The above-described interactive robotic system may also be used in hip replacement surgery, which may require the use of multiple surgical tools having different functions (e.g., reaming, impacting), different configurations (e.g., straight, offset), and different weights. A system designed to accommodate a variety of tools is described in U.S. patent application Ser. No. 12/894,071, filed Sep. 29, 2010, entitled "SURGICAL SYSTEM FOR POSITIONING PROSTHETIC COMPONENT AND/OR FOR CONSTRAINING MOVEMENT OF SURGICAL TOOL", which is hereby incorporated by reference in its entirety.

During a hip replacement surgery, as well as other robotically assisted or fully autonomous surgical procedures, the patient bones including the pelvis and the femur are intra-operatively registered with corresponding virtual or computer bone models to correlate the pose (i.e., position and rotational orientation) of the actual, physical bone with the virtual bone models. The patient bone (physical space) is also tracked relative to the surgical robot, haptic device, or surgical tool, which may include at least one degree of freedom (e.g., rotating burr). In this way, the virtual cutting or haptic boundaries controlled and defined on the virtual bone model via a computer can be applied to the patient bone (physical space) such that the haptic device is constrained in its physical movement (e.g., burring) when working on the patient bone (physical space).

Intra-operative registration of the pelvis and femur can be challenging. And while certain systems and methods exist in the art for registration of a patient pelvis and femur, there is need in the art for registration methods that increase accuracy while decreasing registration time.

SUMMARY

Aspects of the present disclosure may include a system for registering a surgical device and a femur of a patient. The femur may include an exterior surface and an inner canal. The femur of the patient and the surgical device may be in an operative coordinate system. The system may include at least one computing device in communication with a surgical navigation system and the surgical device. The surgical navigation system may track the surgical device. The at least one computing device storing a surgical plan in a virtual coordinate space. The at least one computing device is configured for the following steps. The at least one computing device may receive external bone registration data corresponding to locations on the exterior surface of the femur. The at least one computing device may calculate a first registration transform based on the external bone registration data. The at least one computing device may transform a first bone removal plan of the surgical plan to the operative coordinate system based on the first registration transform. The at least one computing device may receive internal bone canal registration data corresponding to at least one of location or orientation data from the inner canal of the femur. The at least one computing device may calculate a second registration transform based on both of the external bone registration data and the internal bone canal registration data. The at least one computing device may transform a second bone removal plan of the surgical plan to the operative coordinate system based on the second registration transform.

In certain instances, the first bone removal plan may be defined in the virtual coordinate space and may include first coordinate locations for a first portion of bone removal from a virtual inner canal that may be representative of the inner canal of the femur of the patient.

In certain instances, the second bone removal plan may be defined in the virtual coordinate space and may include second coordinate locations for a second portion of bone removal from the virtual inner canal that may be representative of the inner canal of the femur of the patient.

In certain instances, the first portion of bone removal from the first bone removal plan includes less bone removal from the virtual canal than the first and second bone removal plans combined. In certain instances, the first bone removal plan includes only a partial femur canal preparation plan that may be less than a full canal preparation needed for implantation of a stem of a femoral implant. In certain instances, the first portion of bone removal from the first bone removal plan and the second portion of bone removal from the second bone removal plan collectively amount to a full canal preparation plan.

In certain instances, the second bone removal plan includes a robotic bone removal portion and a manual bone removal portion.

In certain instances, the manual bone removal portion may be planned for a broach.

In certain instances, the second coordinate locations for the second portion of bone removal includes the first coordinate locations for the first portion of bone removal.

In certain instances, the second coordinate locations for the second portion of bone removal from the second bone removal plan encompasses the first coordinate locations for the first portion of bone removal from the first bone removal plan.

In certain instances, the surgical navigation system may include a tracking device and at least one tool configured to be tracked in its movement by the tracking device.

In certain instances, the surgical plan further may include a position and orientation for a femoral neck etch, the at least one computing device configured for receiving femoral neck etch data corresponding to physical marks on the femoral neck, the marks being less than a complete resection of the femoral neck.

In certain instances, the at least one computing device is further configured for comparing the first registration transform to the second registration transform, and proceeding with one of the first registration transform or the second registration transform based on the comparison.

Aspects of the present disclosure may include a computer implemented method of registration of a surgical device and a femur of a patient. The femur includes an exterior surface and an inner canal. The surgical device and the femur of the patient are in an operative coordinate system. The computer implemented method may include the following steps. The method may include the step of receiving external bone registration data corresponding to locations on the exterior surface of the femur. The method may include the step of calculating a first registration transform based on the external bone registration data. The method may include the step of transforming a first bone removal plan of a surgical plan to the operative coordinate system based on the first registration transform, the first bone removal plan including a partial femoral canal preparation plan that may be less than a full canal preparation plan needed for receiving a stem of a femoral implant. The method may include the step of receiving internal bone canal registration data corresponding to at least one of location or orientation data from the inner canal of the femur. The method may include the step of calculating a second registration transform based on both of the external bone registration data and the internal bone canal registration data. And the method may include the step of transforming a second bone removal plan of the surgical plan to the operative coordinate system based on the second registration transform.

In certain instances, the method may further include: determining a planned implant placement of an implant model relative to a femoral bone model, the femoral bone model being representative of the femur of the patient.

In certain instances, the method may further include: determining a surgical plan in order to achieve the planned implant placement, the surgical plan may include the first bone removal plan and the second bone removal plan.

In certain instances, the first bone removal plan may be planned in a virtual coordinate system relative to a femoral bone model representative of the femur, the virtual coordinate system being different than the operative coordinate system. And, transforming the first bone removal plan to the operative coordinate system based on the first registration transform may include mapping the first bone removal plan to the femur in the operative coordinate system in the same position and orientation that the first bone removal plan may be relative to the femoral bone model in the virtual coordinate system.

In certain instances, the second bone removal plan may be planned in a virtual coordinate system relative a femoral bone model representative of the femur, the virtual coordinate system being different than the operative coordinate system. And, transforming the second bone removal plan to the operative coordinate system based on the second registration transform may include mapping the second bone removal plan to the femur in the operative coordinate system in the same position and orientation that the second bone removal plan may be relative to the femoral bone model in the virtual coordinate system.

In certain instances, the second bone removal plan includes removal of bone from the inner canal of the femur, and the second bone removal plan encompasses the bone removal from the first bone removal plan. In certain instances, second bone removal plan includes removal of additional bone beyond the bone in the first bone removal plan.

Aspects of the present disclosure may include a system for registering patient data of a first bone in a first coordinate system with a surgical plan associated with the first bone in a second coordinate system that may be different than the first coordinate system. The first bone may include a head portion and a shaft portion extending from the head portion. The system may include at least one computing device in communication with a surgical navigation system that may include a tracking device and at least one tool configured to be tracked in its movement by the tracking device. The at least one computing device storing the surgical plan in the second coordinate system. The surgical plan may include a virtual bone model representative of the first bone, a first bone removal plan associated with the virtual bone model, and a second bone removal plan associated with the virtual bone model. The at least one computing device configured for receiving a first point-cloud of data associated with the first bone, the first point-cloud of data may include first data associated with the head portion of the first bone. The at least one computing device configured for calculating a first registration transform from the first point-cloud of data. The at least one computing device configured for, using the first registration transform, transforming the first bone removal plan of the surgical plan to the first coordinate system in a position and orientation relative to the first bone as the first bone removal plan existed in the second coordinate system relative to the virtual bone model. The at least one computing device configured for receiving a second point-cloud of data associated with the first bone, the second point-cloud of data may include second data associated with an internal portion of the shaft portion of the first bone. The at least one computing device configured for calculating a second registration transform from both of the first and second point-clouds of data. And, the at least one computing device configured for, using the second registration transform, transforming the second bone removal plan of the surgical plan to the first coordinate system in a position and orientation relative to the first bone as the second bone removal plan existed in the second coordinate system relative to the virtual bone model.

In certain instances, the first and second point-cloud of data may be gathered intra-operatively via a surgical device that may be tracked in its movement by the tracking device of the surgical navigation system.

In certain instances, the first bone removal plan includes a first plan for partial removal of bone from a virtual canal of the virtual bone model.

In certain instances, the second bone removal plan includes a second plan for full removal of bone from the virtual canal of the virtual bone model, the first and second bone removal plans being for preparation of implantation of a stem of a femoral implant.

Aspects of the present disclosure may include one or more tangible computer-readable storage media storing computer-executable instructions for performing a computer process on a computing system. The computer process may include the following steps. The computer process may include the step of receiving a plurality of image scans of a patient pelvis. The computer process may include the step of generating a three-dimensional bone model of the patient pelvis from the plurality of image scans. The computer process may include the step of identifying a scan axis associated with the plurality of image scans, the scan axis defined along a long axis of a scanning table of an imaging machine. The computer process may include the step of identifying a bone axis associated with the three-dimensional bone model of the patient pelvis. The computer process may include the step of determining an angular offset between the scan axis and the bone axis. The computer process may include the step of determining a virtual center of rotation of at least one virtual bone relative to a three-dimensional bone model of the patient pelvis. The computer process may include the step of using the angular offset and the virtual center of rotation as constraints in a registration transform to be employed in a surgical registration procedure.

Aspects of the present disclosure may include one or more tangible computer-readable storage media storing computer-executable instructions for performing a computer process on a computing system. The computer process may include the following steps. The computer process may include the step of receiving a point-cloud of data from at least one tool of a surgical navigation system, the at least one tool tracked in its movement by a tracking device of the surgical navigation system. The at least one tool may be configured to store data points in the point-cloud data. The point-cloud of data may include first data and second data in a common coordinate system. The first data may include a pair of points located on or proximate a surgical table. The second data may include a plurality of points corresponding to a concave portion of a joint surface of between a first bone may include the concave portion and a second bone may include a convex portion. The computer process may include the step of determining a vector between the pair of points of the first data. The computer process may include the step of determining a center of rotation from the second data, the center of rotation being of the second bone relative to the first bone. The computer process may include the step of employing a registration transform that registers the point-cloud of data with a three-dimensional computer model of at least the first bone, the vector and the center of rotation being constraints in the registration transform.

Aspects of the present disclosure may include a computer-implemented method for surgical registration including the following steps. The method may include the step of receiving a point-cloud of data from at least one tool of a surgical navigation system, the at least one tool tracked in its movement by a tracking device of a surgical navigation system. The at least one tool configured to store data points in the point-cloud data based on its position relative to the tracking device. The point-cloud of data may include first data and second data in a first coordinate system. The first data may include first and second coordinate points located on or proximate a surgical table. The second data may include one or more coordinate points corresponding to a center-of-rotation of a joint formed between a pair of bones. The method may include the step of employing a registration transform that registers the point-cloud of data with a plurality of coordinate points associated with a three-dimensional computer model of or approximating the pair of bones and the joint. The plurality of coordinate points may include one or more coordinate points corresponding to a center-of-rotation of the joint. The plurality of coordinate points in a second coordinate system.

In certain instances, the first and second coordinate points located on or proximate the surgical table are aligned parallel with a long axis of the surgical table.

In certain instances, the first data may include a third coordinate point located on or proximate the surgical table, the third coordinate point may be located on an opposite side of the surgical table from the first and second coordinate points.

In certain instances, the three-dimensional computer model of or approximating the pair of bones and the joint may be generated from pre-operative image scans of the pair of bones and the joint.

In certain instances, the three-dimensional computer model of or approximating the pair of bones and the joint may include a generic bone model approximating the pair of bones and the joint.

In certain instances, the three-dimensional computer model of or approximating the pair of bones and the joint may include a statistical bone model approximating the pair of bones and the joint.

Aspects of the present disclosure may include a surgical registration system including the following. A registration needle that may include a distal tip and a proximal light emitting diode (LED) optical marker, the proximal LED optical marker configured to be tracked by a tracking device of a surgical navigation system. A needle template that may include a template block having a plurality of through-holes extending therethrough, the plurality of through-holes are spaced-apart from each other on the template block, and each of the plurality of through-holes are configured to guide the registration needle along a trajectory. And an optical localization tracker coupled to the needle template, the optical localization tracker configured to be tracked by the tracking device of the surgical navigation system.

Aspects of the present disclosure may include a system for registering patient data gathered intra-operatively of a vertebra with a computer model of the vertebra in a coordinate system. The vertebra may include a cortical bone shell having an outer surface and an inner surface, and cancellous bone interior of the cortical bone shell. The vertebra may define a spinal cord canal bounded by the cortical bone shell. The system may include a surgical navigation system including a tracking device and at least one tool configured to be tracked in its movement by the tracking device, the at least one tool may include an end effector having a cutting element at a distal end thereof, and a load cell configured to sense a load on the cutting element. The system may also include at least one computing device in communication with the surgical navigation system, the at least one computing device storing the computer model of the vertebra in the coordinate system. The at least one computing device configured for receiving load data associated with a load experienced by the cutting element at the distal end of the end effector when the cutting element contacts the cortical bone shell and the cancellous bone. The at least one computing device configured for identifying, based on the load data, when the cutting element contacts the inner surface of the cortical bone shell. The at least one computing device configured for receiving a point-cloud of data associated with the vertebra, the point-cloud of data may include coordinate locations on the inner surface of the cortical bone shell, the point-cloud of data collected via the cutting element at the distal end of the end effector. The at least one computing device configured for at least one of running or updating a transform to register the point-cloud of data associated with the vertebra to the computer model of the vertebra in a common coordinate system.

BRIEF DESCRIPTION OF THE DRAWINGS

FIG. 15A depicts an overhead view of a patient on an imaging table.

FIG. 15B depicts an overhead view of a patient on an operating room table.

FIG. 15C depicts an angular offset between a vector determined in the operating room and a pelvic axis determined from the patient's orientation on the imaging table.

DETAILED DESCRIPTION

The present application incorporates by reference the following applications in their entireties: International Application PCT/US2017/049466, filed Aug. 30, 2017, entitled "SYSTEMS AND METHODS FOR INTRA-OPERATIVE PELVIC REGISTRATION"; U.S. patent application Ser. No. 12/894,071, filed Sep. 29, 2010, entitled "SURGICAL SYSTEM FOR POSITIONING PROSTHETIC COMPONENT AND/OR FOR CONSTRAINING MOVEMENT OF SURGICAL TOOL"; U.S. patent application Ser. No. 13/234,190, filed Sep. 16, 2011, entitled "SYSTEMS AND METHOD FOR MEASURING PARAMETERS IN JOINT REPLACEMENT SURGERY"; U.S. patent application Ser. No. 11/357,197, filed Feb. 21, 2006, entitled "HAPTIC GUIDANCE SYSTEM AND METHOD"; U.S. patent application Ser. No. 12/654,519, filed Dec. 22, 2009, entitled "TRANSMISSION WITH FIRST AND SECOND TRANSMISSION ELEMENTS"; U.S. patent application Ser. No. 12/644,964, filed Dec. 22, 2009, entitled "DEVICE THAT CAN BE ASSEMBLED BY COUPLING"; and U.S. patent application Ser. No. 11/750,807, filed May 18, 2007, entitled "SYSTEM AND METHOD FOR VERIFYING CALIBRATION OF A SURGICAL DEVICE".

I. Overview

Figure 1A:
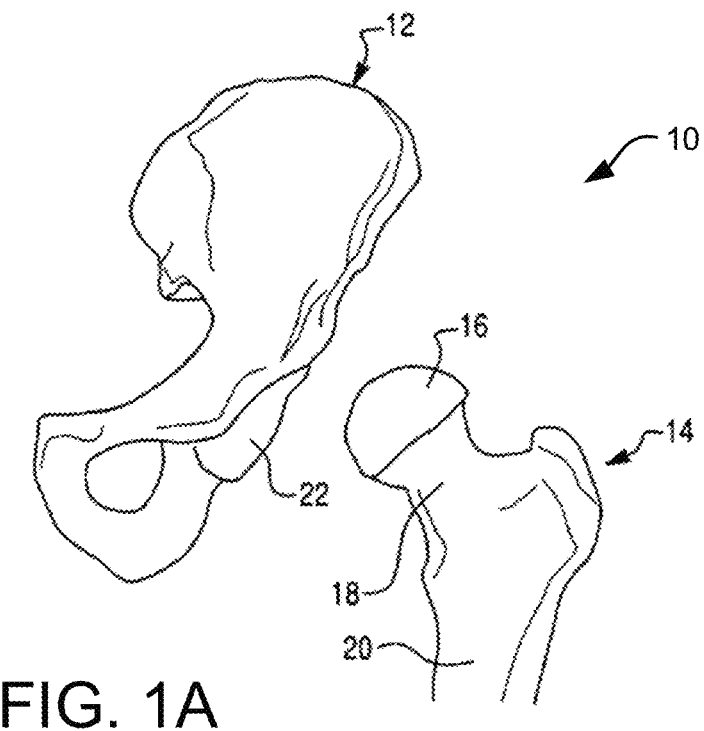
FIG. 1A is a perspective view of a femur and a pelvis.
Figure 1B:
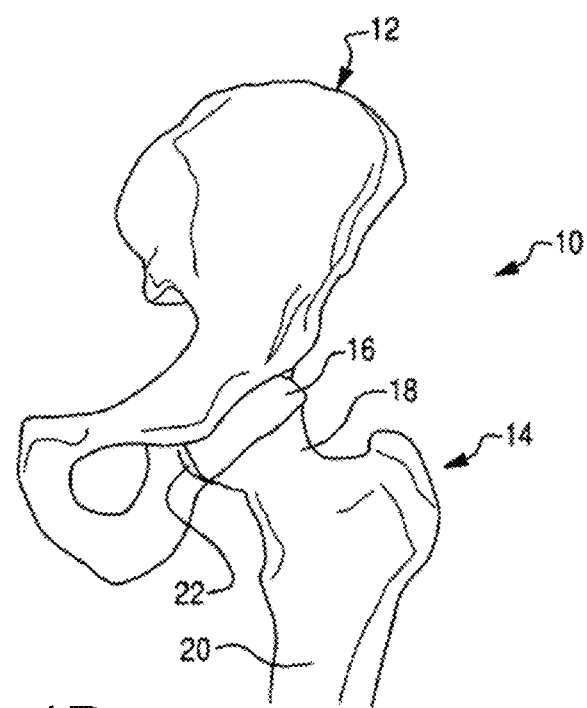
FIG. 1B is a perspective view of a hip joint formed by the femur and pelvis of FIG. 1A.

The hip joint is the joint between the femur and the pelvis and primarily functions to support the weight of the body in static (e.g., standing) and dynamic (e.g., walking) postures. FIG. 1A illustrates the bones of an operative side of a hip joint 10, which include a left pelvis or ilium 12 and a proximal end of a left femur 14. While a right pelvis and proximal end of a right femur is not shown in FIG. 1A, such a discussion herein is applicable to both the right and the left femur and pelvis without limitation. Continuing on, the proximal end of the femur 14 includes a femoral head 16 disposed on a femoral neck 18. The femoral neck 18 connects the femoral head 16 to a femoral shaft 20. As shown in FIG. 1B, the femoral head 16 fits into a concave socket in the pelvis 12 called the acetabulum 22, thereby forming the hip joint 10. The acetabulum 22 and femoral head 16 are both covered by articular cartilage that absorbs shock and promotes articulation of the joint 10.

Figure 2B:
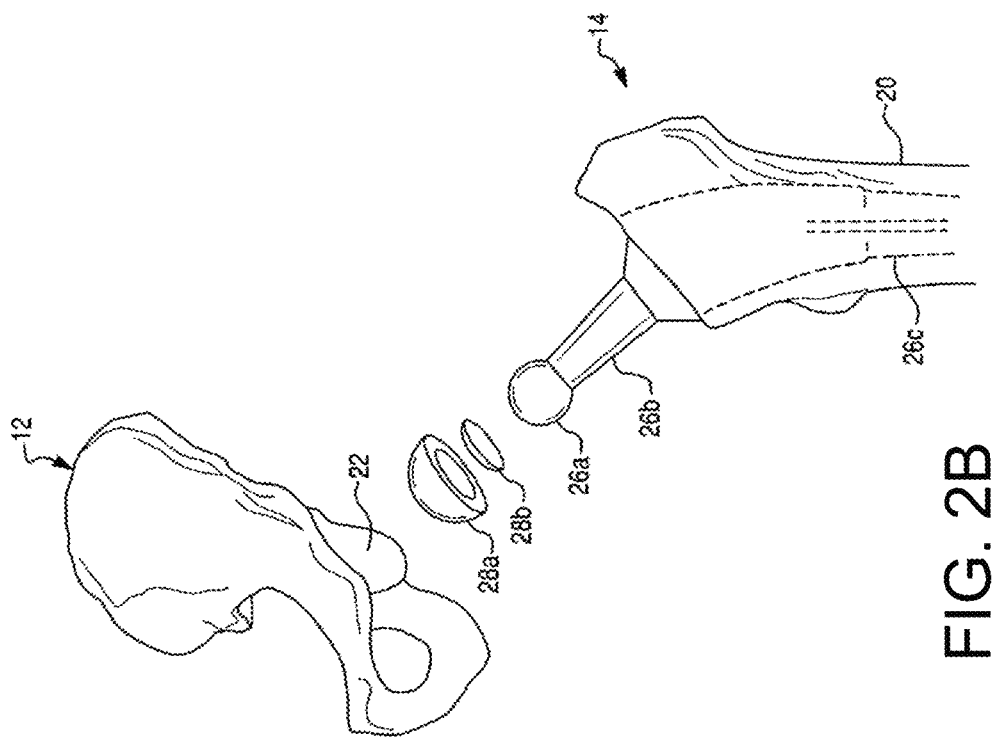
FIG. 2B is a perspective view illustrating placement of the femoral component and acetabular component of FIG. 2A in relation to the femur and pelvis of FIG. 1A, respectively.
Figure 2A:
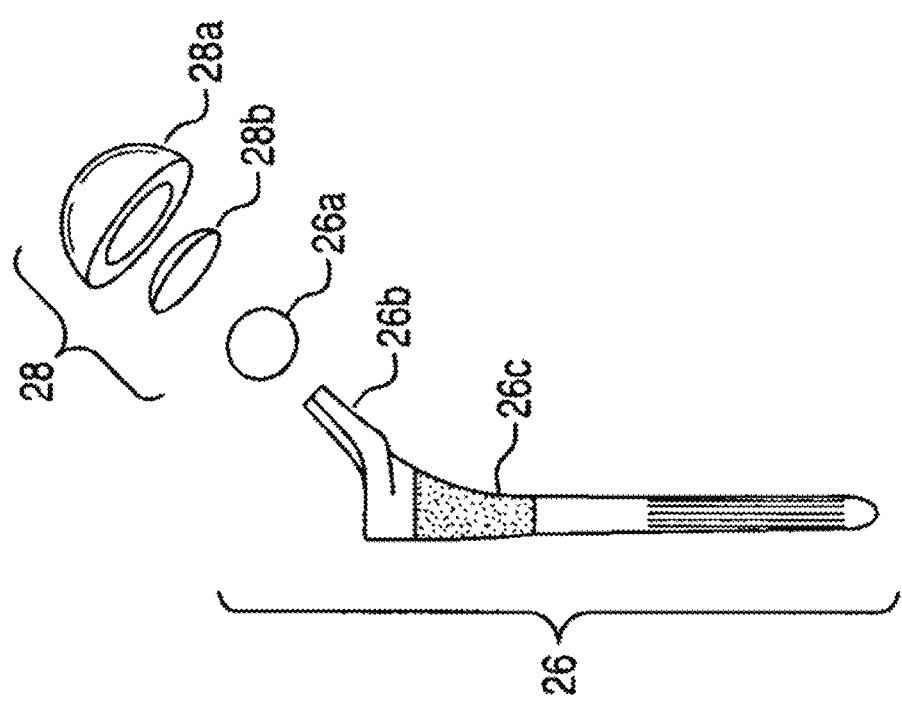
FIG. 2A is an exploded perspective view of a femoral component and an acetabular component for a total hip replacement procedure.

Over time, the hip joint 10 may degenerate (e.g., due to osteoarthritis) resulting in pain and diminished functionality. As a result, a hip replacement procedure, such as total hip arthroplasty or hip resurfacing, may be necessary. During hip replacement, a surgeon replaces portions of a patient's hip joint 10 with artificial components. In total hip arthroplasty, the surgeon removes the femoral head 16 and neck 18 and replaces the native bone with a prosthetic femoral component 26 comprising a head 26a, a neck 26b, and a stem 26c (shown in FIG. 2A). As shown in FIG. 2B, the stem 26c of the femoral component 26 is anchored in a cavity the surgeon creates in the intramedullary canal of the femur 14. Alternatively, if disease is confined to the surface of the femoral head 16, the surgeon may opt for a less invasive approach in which the femoral head is resurfaced (e.g., using a cylindrical reamer) and then mated with a prosthetic femoral head cup (not shown). Similarly, if the natural acetabulum 22 of the pelvis 12 is worn or diseased, the surgeon resurfaces the acetabulum 22 using a reamer and replaces the natural surface with a prosthetic acetabular component 28 comprising a hemispherical shaped cup 28a (shown in FIG. 2A) that may include a liner 28b. To install the acetabular component 28, the surgeon connects the cup 28a to a distal end of an impactor tool and implants the cup 28a into the reamed acetabulum 22 by repeatedly striking a proximal end of the impactor tool with a mallet. If the acetabular component 28 includes a liner 28b, the surgeon snaps the liner 28b into the cup 28a after implanting the cup 28a. Depending on the position in which the surgeon places the patient for surgery, the surgeon may use a straight or offset reamer to ream the acetabulum 22 and a straight or offset impactor to implant the acetabular cup 28a. For example, a surgeon that uses a postero-lateral approach may prefer straight reaming and impaction whereas a surgeon that uses an antero-lateral approach may prefer offset reaming and impaction.

II. Exemplary Robotic System

Figure 3A:
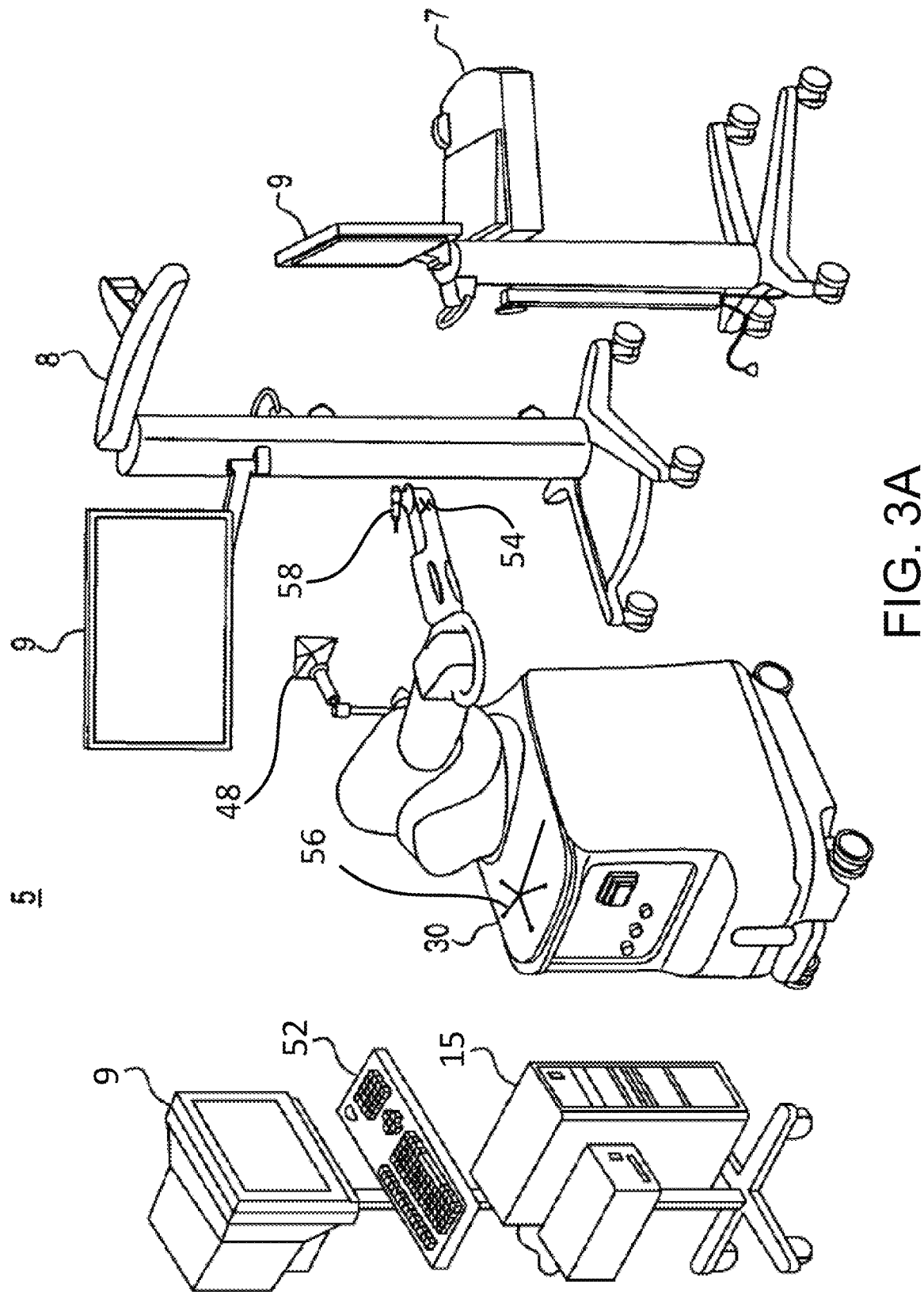
FIG. 3A is a perspective view of an embodiment of a surgical system.

A surgical system described herein may be utilized to perform hip replacement, as well as other surgical procedures. As shown in FIG. 3A, an embodiment of a surgical system 5 for surgical applications according to the present disclosure includes a computer assisted navigation system 7, a tracking device 8, a computer 15, a display device 9 (or multiple display devices 9), and a robotic arm 30.

Figure 3B:
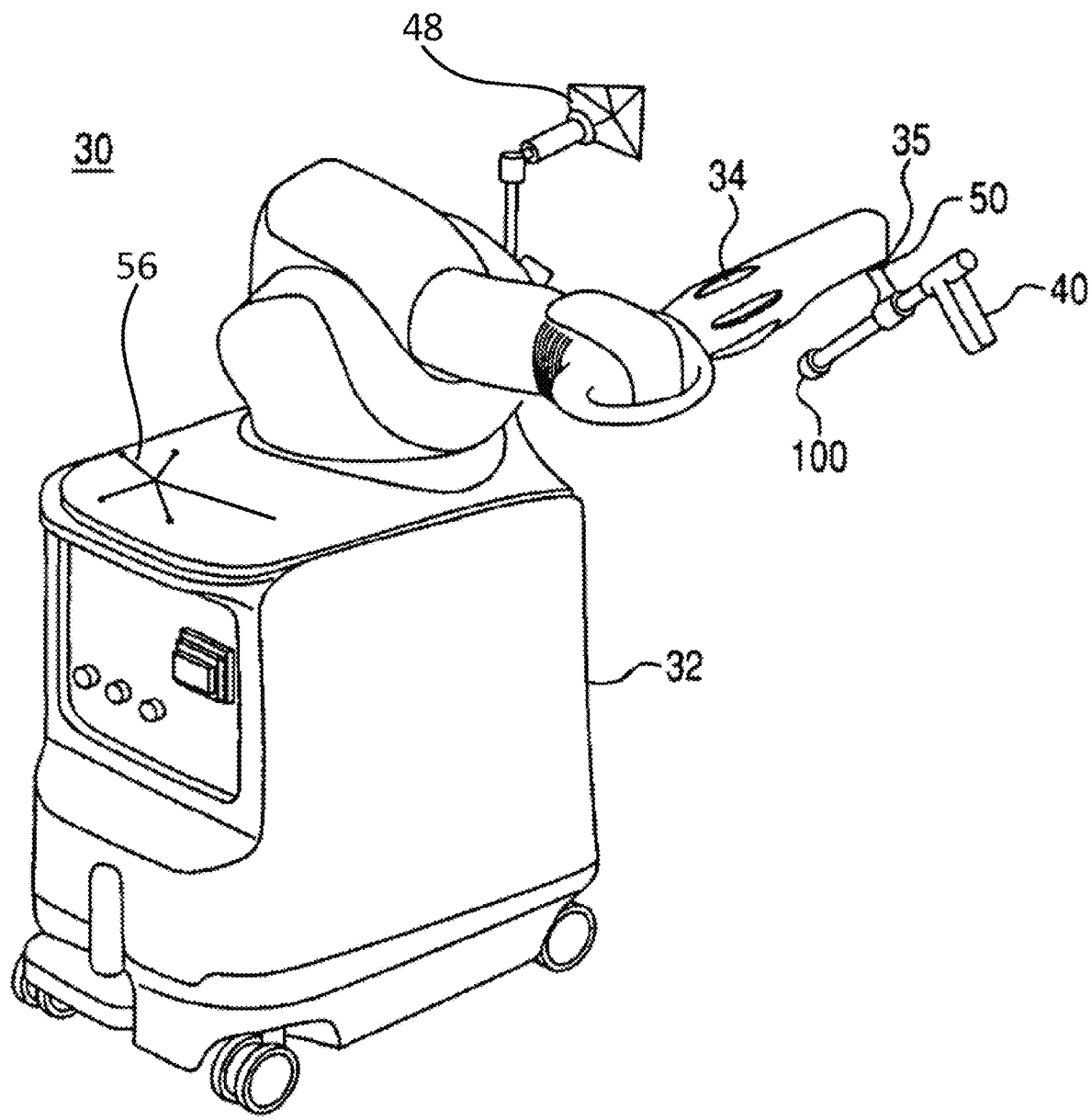
FIG. 3B is a perspective view of an embodiment of a robotic arm of the surgical system of FIG. 3A.

The robotic arm 30 can be used in an interactive manner by a surgeon to perform a surgical procedure on a patient, such as a hip replacement procedure. As shown in FIG. 3B, the robotic arm 30 includes a base 32, an articulated arm 34, a force system (not shown), and a controller (not shown). A surgical tool 58 (e.g., a rotary burring device as seen in FIG. 3A, an end effector 40 having an operating member as seen in FIG. 3B) is coupled to an end of the articulated arm 34, and the surgeon manipulates the surgical tool 58 by grasping and manually moving the articulated arm 34 and/or the surgical tool.

The force system and controller are configured to provide control or guidance to the surgeon during manipulation of the surgical tool. The force system is configured to provide at least some force to the surgical tool via the articulated arm 34, and the controller is programmed to generate control signals for controlling the force system. In one embodiment, the force system includes actuators and a backdriveable transmission that provide haptic (or force) feedback to constrain or inhibit the surgeon from manually moving the surgical tool beyond predefined virtual boundaries defined by haptic objects as described, for example, in U.S. patent application Ser. No. 11/357,197 (Pub. No. US 2006/0142657), filed Feb. 21, 2006, and/or U.S. patent application Ser. No. 12/654,519, filed Dec. 22, 2009, each of which is hereby incorporated by reference herein in its entirety. In a certain embodiment the surgical system is the RIO™. Robotic Arm Interactive Orthopedic System manufactured by MAKO Surgical Corp. of Weston, Fla. The force system and controller may be housed within the robotic arm 30, or may be part of an autonomous or handheld unit. Generally, the method of surgical registration may be done with a robotic arm of a surgical robot operating autonomously, or being guided by a surgeon under haptic controls. Similarly, the method of surgical registration may be done via a handheld unit operating within a permissible zone of operation.

The tracking device 8 is configured to track the relative locations of the surgical tool 58 (coupled to the robotic arm 30) and the patient's anatomy. The surgical tool 58 can be tracked directly by the tracking device 8. Alternatively, the pose of the surgical tool can be determined by tracking the location of the base 32 of the robotic arm 30 and calculating the pose of the surgical tool 58 based on joint encoder data from joints of the robotic arm 30 and a known geometric relationship between the surgical tool and the robotic arm 30. In particular, the tracking device 8 (e.g., an optical, mechanical, electromagnetic, or other known tracking system) tracks (or enables determination of) the pose (i.e., position and orientation) of the surgical tool and the patient's anatomy so the navigation system 7 knows the relative relationship between the tool and the anatomy.

In operation, a user (e.g., a surgeon) manually moves the robotic arm 30 to manipulate the surgical tool 58 (e.g., the rotary burring device, the end effector 40 having an operating member) to perform a surgical task on the patient, such as bone cutting or implant installation. As the surgeon manipulates the tool 58, the tracking device 8 tracks the location of the surgical tool and the robotic arm 30 provides haptic (or force) feedback to limit the surgeon's ability to move the tool 58 beyond a predefined virtual boundary that is registered (or mapped) to the patient's anatomy, which results in highly accurate and repeatable bone cuts and/or implant placement. The robotic arm 30 operates in a passive manner and provides haptic feedback when the surgeon attempts to move the surgical tool 58 beyond the virtual boundary. The haptic feedback is generated by one or more actuators (e.g., motors) in the robotic arm 30 and transmitted to the surgeon via a flexible transmission, such as a cable drive transmission. When the robotic arm 30 is not providing haptic feedback, the robotic arm 30 is freely moveable by the surgeon and preferably includes a virtual brake that can be activated as desired by the surgeon. During the surgical procedure, the navigation system 7 displays images related to the surgical procedure on one or both of the display devices 9.

To aid in tracking the various pieces of equipment within the system, the robotic arm 30 may include a device marker 48 to track a global or gross position of the robotic arm 30, a tool end marker 54 to track the distal end of the articulating arm 34, and a free-hand navigation probe 56 for use in the registration process. Each of these markers 48, 54, 56 (among others such as navigation markers positioned in the patient's bone) is trackable by the tracking device 8 with optical cameras, for example.

The computer 15 may include a display and an input device (e.g., keyboard, mouse) and is configured to communicate with the navigation system 7, the tracking device 8, the various display devices 9 in the system, and the robotic arm 30. Furthermore, the computer 15 may receive information related to a particular surgical procedure and perform various functions related to performance of the surgical procedure. For example, the computer 15 may have software as necessary to perform functions related to image analysis, surgical planning, registration, navigation, image guidance, and haptic guidance. A more detailed analysis of an example computing system having one or more computing units that may implement various systems and methods discussed herein, is described subsequently in reference to FIG. 14.

FIG. 3B depicts an end effector 40 particularly suited for use in robotic assisted hip arthroplasty. The end effector 40 is configured to be mounted to an end of the robotic arm 30. The end effector 40 includes a mounting portion 50, a housing, a coupling device, and a release member. The end effector 40 is configured to individually and interchangeably support and accurately position multiple operating members relative to the robotic arm 30. As seen in FIG. 3B, the end effector 40 is coupled to an operating member 100. The end effector 40 and related tools, systems, and methods are described in U.S. patent application Ser. No. 12/894,071, filed Sep. 29, 2010, which is hereby incorporated by reference in its entirety.

The mounting portion (or mount) 50 preferably couples the end effector 40 to the robotic arm 30. In particular, the mounting portion 50 extends from the housing and is configured to couple the end effector 40 to a corresponding mounting portion 35 of the robotic arm 30 using, for example, mechanical fasteners, such that the mounting portions are fixed relative to one another. The mounting portion 50 can be attached to the housing or formed integrally with the housing and is configured to accurately and repeatedly position the end effector 40 relative to the robotic arm 30. In one embodiment, the mounting portion 50 is a semi-kinematic mount as described in U.S. patent application Ser. No. 12/644,964, filed Dec. 22, 2009, and hereby incorporated by reference herein in its entirety.

The end effector 40 in FIG. 3B is one example of a surgical tool that can be tracked and used by the surgical robotic arm 30. Other tools (e.g., drills, burrs) as known in the art can be attached to the robotic arm for a given surgical procedure.

III. Pre-operative Planning a Surgical Procedure

Prior to the surgical procedure, a preoperative CT (computed tomography) scan of the patient's pelvis 12 and femur 14 is generated with a medical imaging device. While the discussion will focus on CT scans, other imaging modalities (e.g., MRI) may be similarly be employed. Additionally, and alternatively, X-ray images derived from the CT scan and/or the three-dimensional models 512, 514 can be used for surgical planning, which may be helpful to surgeons who are accustomed to planning implant placement using actual X-ray images as opposed to CT based models. Additionally, a generic model of the bone or a statistical model of the bone could be used. The models could be morphed to the patient's bone during the registration process. Additionally, or alternatively, patient specific bone models may also be generated using a combination of two-dimensional X-ray images either with or without patient data collected during registration (e.g., 2D to 3D models).

The CT scan may be performed by the surgeon or at an independent imaging facility. Additionally, or alternatively, intra-operative imaging methods may be employed to generate a patient model of the bone. For example, various boney surfaces of interest may be probed with a tracked probe to generate a surface profile of the surface of interest. The surface profile may be used as the patient bone model. Accordingly, the present disclosure is applicable to all methods of generating a patient bone model or a portion thereof.

Figure 4:
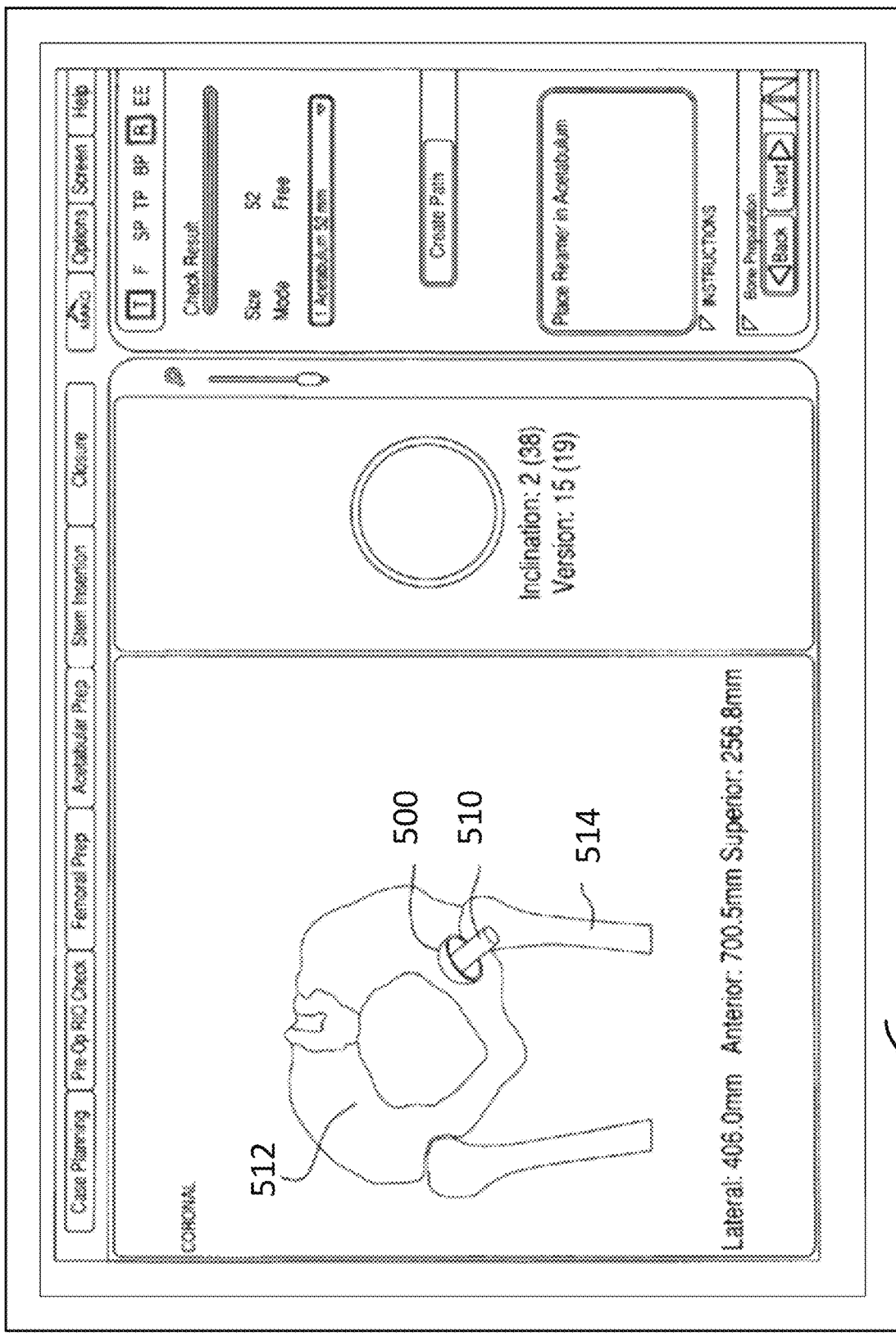
FIG. 4 illustrates an embodiment of a computer display for use during a surgical procedure.

As shown in FIG. 4, the CT scan or data from the CT scan is segmented and to obtain a three-dimensional model 512 of the pelvis 12 and a three-dimensional model 514 of the femur 14. The three-dimensional models 512, 514 are used by the surgeon to construct a surgical plan. The surgeon generates a surgical plan by designating a desired pose (i.e., position and orientation) of the acetabular component and the femoral component relative to the models 512, 514 of the patient's anatomy. For example, a planned pose 500 of the acetabular cup can be designated and displayed on a computer display, such as the display device 9. During the surgical procedure, motion of the patient's anatomy and the surgical tool in physical space are tracked by the tracking device 8, and these tracked objects are registered to corresponding models in the navigation system 7 (image space). As a result, objects in physical space are correlated to corresponding models in image space. Therefore, the surgical system 5 knows the actual position of the surgical tool relative to the patient's anatomy and the planned pose 500, and this information is graphically displayed on the display device 9 during the surgical procedure.

In certain embodiments, the models 512, 514 may be of the full bone surfaces 12, 14 respectively. In certain embodiments, the models 512, 514 may be trimmed three dimensional models providing only critical regions of interest such as the acetabulum 22 and femoral head 16. That is, the trimmed three-dimensional models represent only a portion of the full bone models 512, 514. In certain embodiments, the models 512, 514 may be the combination of multiple models. For example, model 512 may be the combination of individual three-dimensional models of the operative pelvis, non-operative pelvis, and spine.

IV. Intra-operative Procedures

A.

Figure 5:
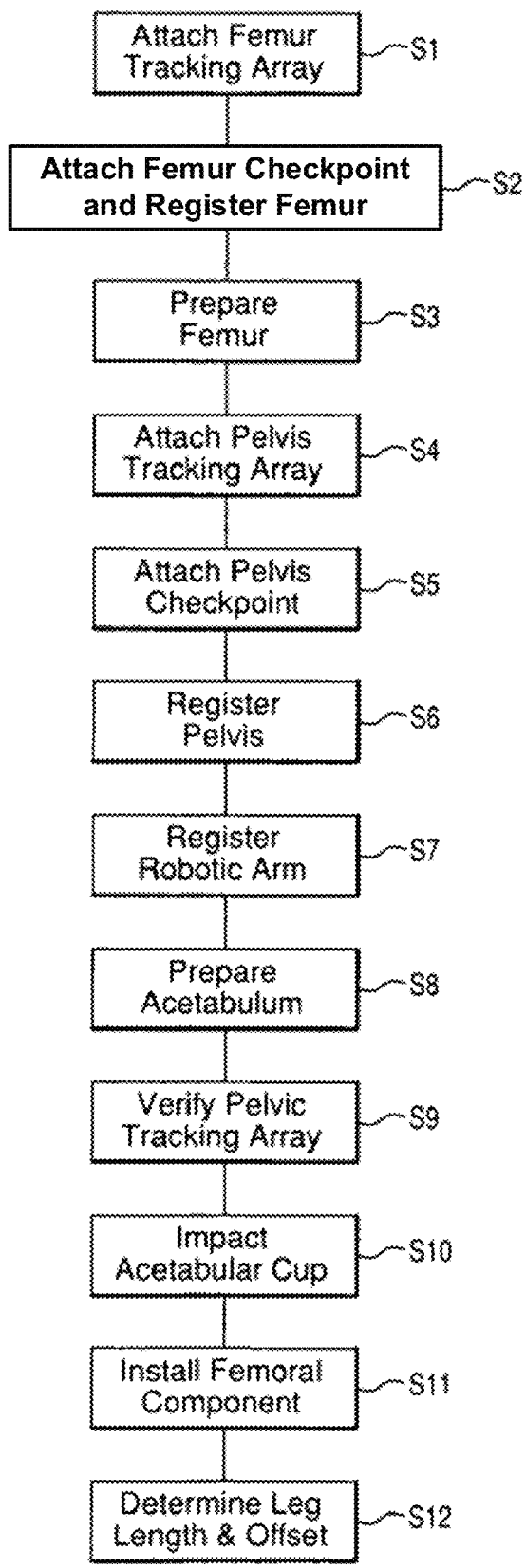
FIG. 5 illustrates an embodiment of steps of a hip replacement procedure.

FIG. 5 illustrates an embodiment of intra-operative steps of performing a total hip replacement. In this embodiment, steps S1-S7, S9, S11, and S12 can be performed with or without robotic assistance. In other embodiments, S1-S2 may not be required, S3-S5 could be done before S1-S2, and S7 could be done at any point before S8. Steps S8 and S10 are preferably performed using the robotic arm 30. For example, step S8 (reaming) can be performed using the robotic arm 30 of FIG. 3 with the end effector 40 coupled to the operating member 100, and step S10 (impacting) can be performed using the robotic arm 30 with the end effector 40 coupled to another operating member.

B. Tracking and Registration of Femur

In step S1 of the surgical procedure, a tracking array is attached to the femur 14 to enable the tracking device 8 to track motion of the femur 14. In step S2, the femur 14 is registered to correlate the pose of the femur 14 (physical space) with the three-dimensional model 514 of the femur 14 in the navigation system 7 (image space). Additionally, the femur checkpoint may be attached. In step S3, the femur is prepared for surgery.

The following description provides exemplary methods of preparing and registering the femur in a surgical procedure on a patient's hip. In certain instances, methods of femoral preparation and registration will be described with reference to FIGS. 8-13. Additionally, certain steps of the preoperative planning of the femur implant and femur preparation will be described as well.

Figure 8:
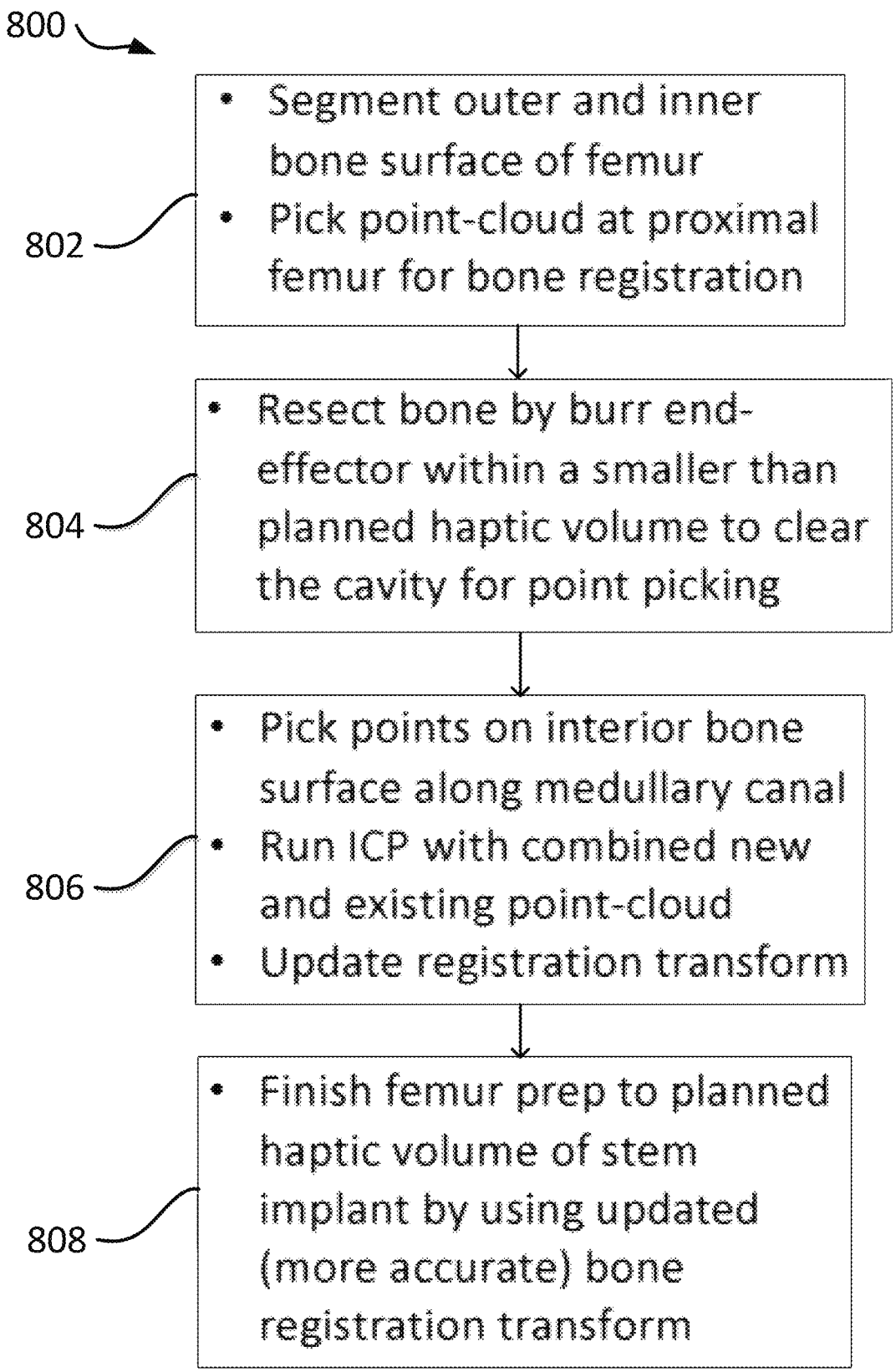
FIG. 8 illustrates steps of a femoral registration method.
Figures 9A, 9B, 9C, 9D:
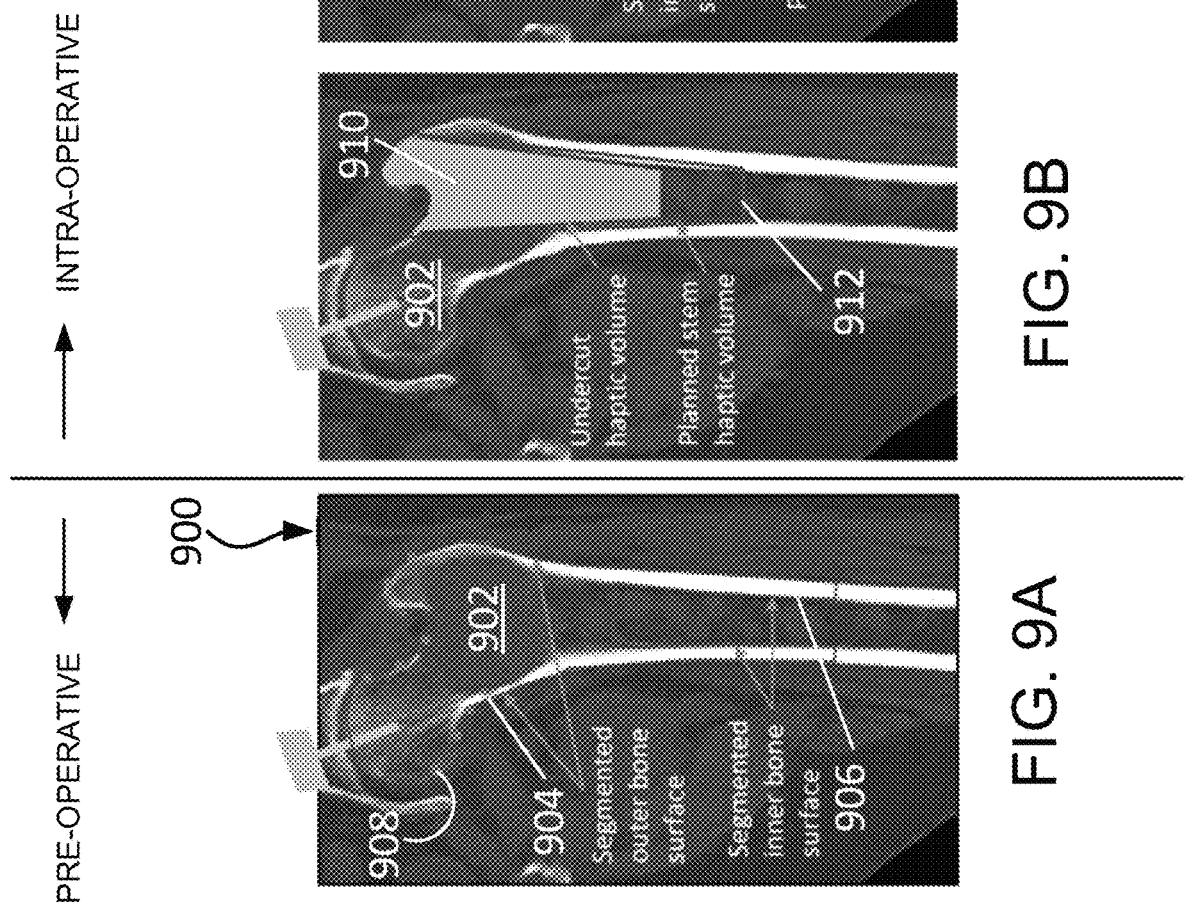
FIG. 9A depicts a pre-operative image of a proximal femur undergoing segmentation.
FIG. 9B depicts a proximal femur with the canal partially resected.
FIG. 9C depicts a proximal femur being probed internally along the femoral canal.
FIG. 9D depicts a proximal femur fully resected along the femoral canal.

To begin, reference is made to FIGS. 8 and 9A-9D. In certain instances, the registration method 800 may include picking points on both an exterior surface of a proximal portion of the femur, and an interior bone surface such as, for example, along the medullary cavity, which is to be prepared for the implantation of a stem of a femoral implant component. In this way, the registration transform may include internal and external bone information to increase the accuracy of the transform. As seen in FIG. 8, the registration method 800 may include segmenting or modeling the outer and inner bone surfaces of the femur at 802. A single medical image 900 of the proximal femur 902 is shown in FIG. 9A, where both the outer bone surface 904 and the inner bone surface 906 are identified for segmentation. While only a single medical image 900 is shown, the registration method 800 may include segmenting a plurality of medical images encompassing the full bone. Thus, the inner and outer bone surfaces of each of the plurality of medical images may be segmented.

The registration method 800, at 802 of FIG. 8, may additionally include identifying a point-cloud at the proximal femur. As seen in FIG. 9A, a series of points 908 and their respective locations are identified and stored in the point-cloud. As seen in the figure, the series of points 908 are located on femoral neck, femoral head, and greater trochanter.

While step 802 of the registration method 800 takes place prior to the surgical procedure, steps 804 through 808 take place intra-operatively. The registration method 800, at 804 of FIG. 8, may include resecting the proximal femur by a burr end-effector within a smaller than planned haptic volume to clear the bone cavity for point picking. As seen in FIG. 9B, the proximal femur 902 has been resected within a volume 910 that is smaller than a volume 912 for subsequent resection for placement of the stem of an implant.

Referring back to FIG. 8, the registration method 800, at 806, may include the surgeon picking, logging, or capturing points on an interior bone surface along the medullary canal. As seen in FIG. 9C, a tracked probe 914 having a pointed tip may be used to capture points on an interior bone surface along the medullary canal of the proximal femur 902. The probe tip may extend through the undercut volume 910 and into the stem volume 912 to the points 916 for capture. The registration method 800, at 806, may also include running an optimization method such as, for example, an iterative closest point (ICP) transform with combined new and existing point-cloud data, and the registration transform may be updated.

At step 808 of the registration method 800, preparation of the femur may be finished to the planned volume (i.e., using the burr end-effector) for subsequent implantation of the stem of the femoral component. As seen in FIG. 9D, the full volume 912 has been resected for the implantation of the stem of the femoral component.

Figure 10:
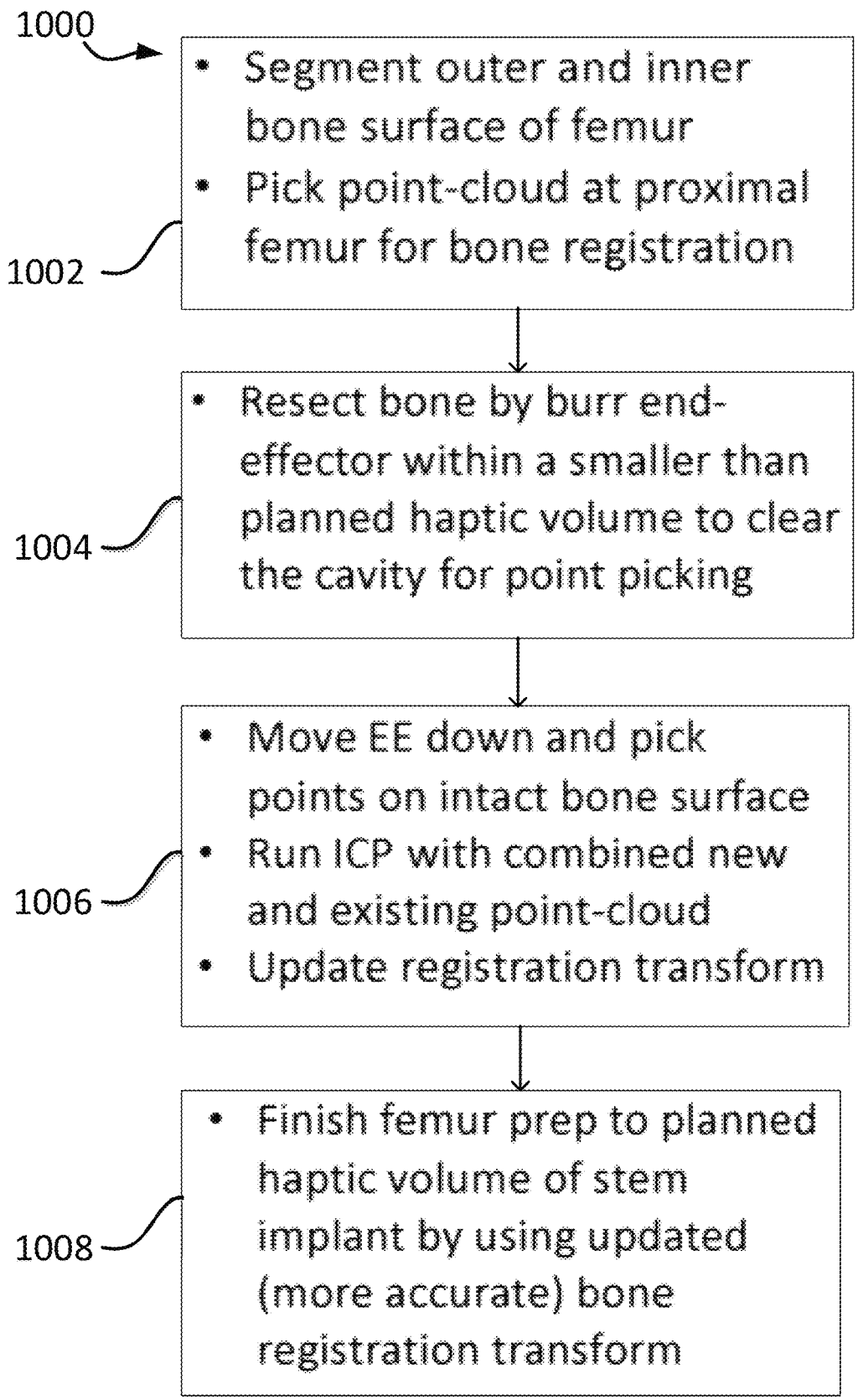
FIG. 10 illustrates steps of a femoral registration method.
Figure 11:
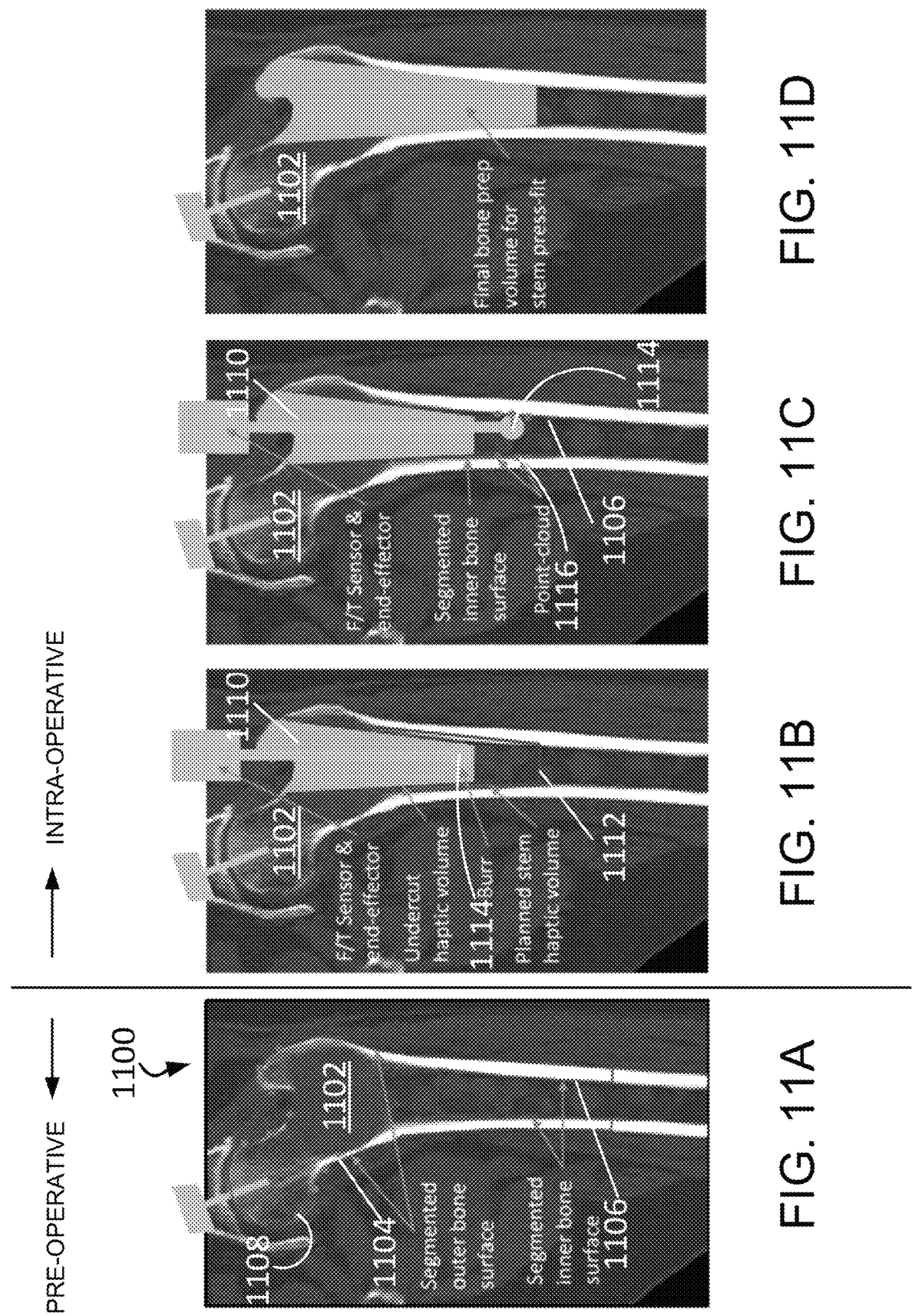
FIG. 11A depicts a pre-operative image of a proximal femur undergoing segmentation.
FIG. 11B depicts a proximal femur with the femoral canal partially resected.
FIG. 11C depicts a proximal femur with the femoral canal partially resected, and with the internal surfaces of the femur being probed with a burr of an end effector.
FIG. 11D depicts a proximal femur with the femoral canal fully resected.

Another femur registration method 1000 is shown in FIGS. 10 and 11A-11D. As seen in FIG. 10, the registration method 1000 may include segmenting an outer and an inner bone surface of the femur, at step 1002. Step 1002 additionally includes picking a point-cloud at the proximal femur for bone registration. FIG. 11A depicts a medical image 1100 of a proximal femur 1102 where both the outer bone surface 1104 and the inner bone surface 1106 are identified for segmentation. The medical image 1100 also includes a series of points 1108 stored in the point-cloud. As seen in the figure, the series of points 1108 are located on femoral neck, femoral head, and greater trochanter.

While step 1002 of the registration method 1000 takes place prior to the surgical procedure, steps 1004 through 1008 take place intra-operatively. Step 1004 of FIG. 10 includes resecting the proximal femur with a burr of an end-effector within a smaller volume than ultimately planned for the implantation of a stem of a femoral implant component. This smaller volume clears the internal femoral cavity for point picking. As seen in FIG. 11B, a burr 1114 of an end effector resects a volume 1110 within an interior part of the proximal end of the femur 1102. Generally, the burr 1114 may resect with a distal or downward trajectory though the femoral neck and greater trochanter. In certain instances, the femoral head may remain un-resected at this point of the procedure. The resected volume 1110, as seen in FIG. 11B, is within the confines of a larger, final preparation volume 1112 that will be resected later in the procedure.

Step 1006 of FIG. 10 includes moving the burr of the end effector (or other tool attached to the end of the end effector) down (distally) the femoral canal and picking, logging, or capturing points on intact bone surfaces on the inner portion of the bone. The bone surface may also be detected automatically by monitoring the state of the motors in the system to determine when contact with a hard surface is made. Then, the iterative closest point (ICP) calculation is run with combined new and existing point-cloud data. The registration transform is then updated. As seen in FIG. 11C, the surgeon extends the burr 1114 through the undercut haptic volume 1110 till the burr 1114 contacts the inner bone surface 1106. The surgeon captures, logs, or picks points 1116 on the inner bone surface 1106. The location of these points is used to update the registration transform. Additionally, or alternatively, the system may automatically detect the burr TCP contacting the inner intact cortical bone surface, or it may be measured using a force/torque sensor (or other type of sensor) attached to the burr end effector.

Step 1008 of FIG. 10 includes finishing the resection of the femoral canal to the planned resection volume or haptic volume for the placement of the stem of the femoral implant component using the updated bone registration transform. As seen in FIG. 11D, the femoral canal is fully resected to the full resection volume 1112 accord to the surgical plan.

Figure 12:
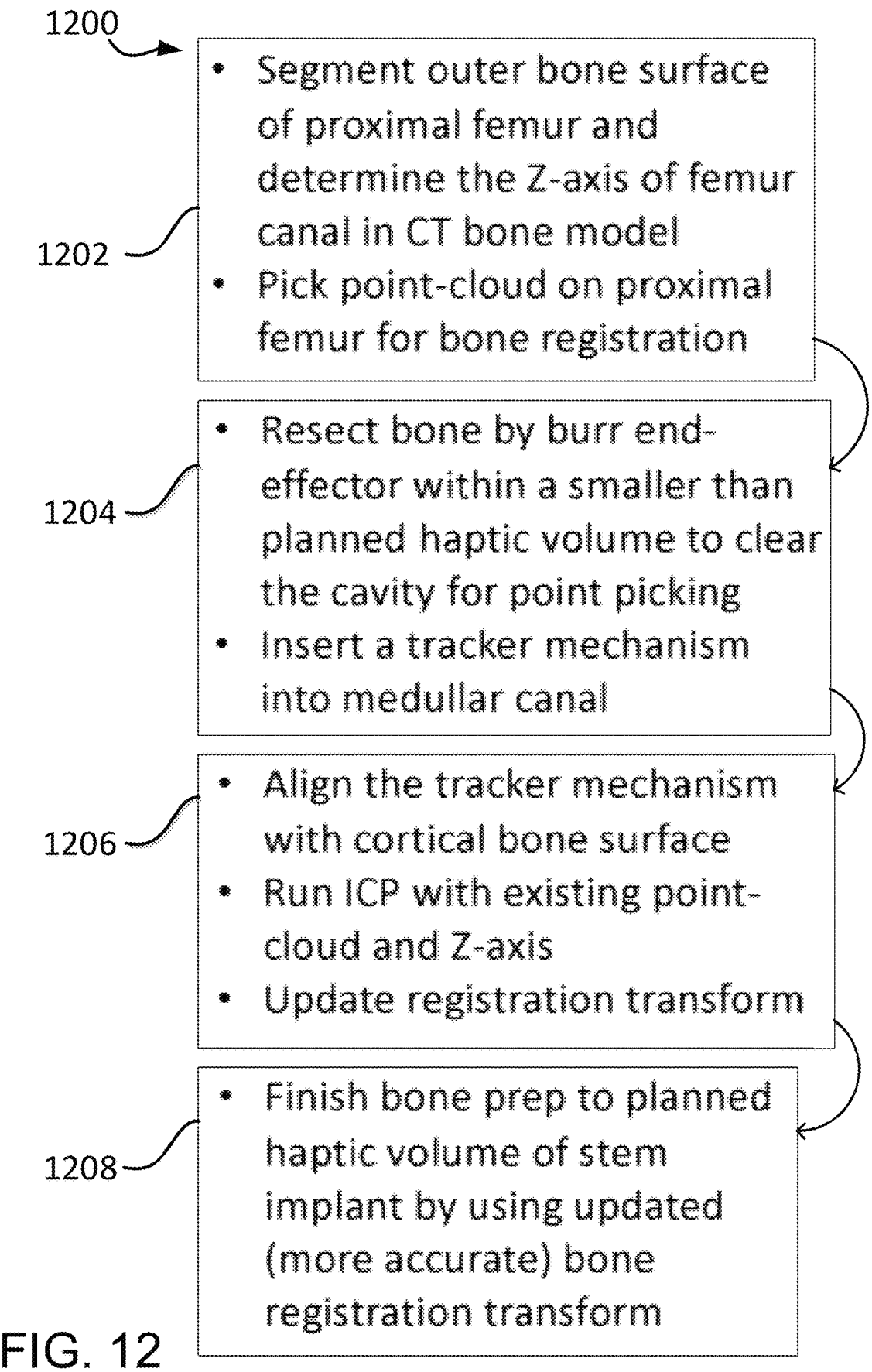
FIG. 12 illustrates steps of a femoral registration method.
Figures 13A, 13B, 13C, 13D:
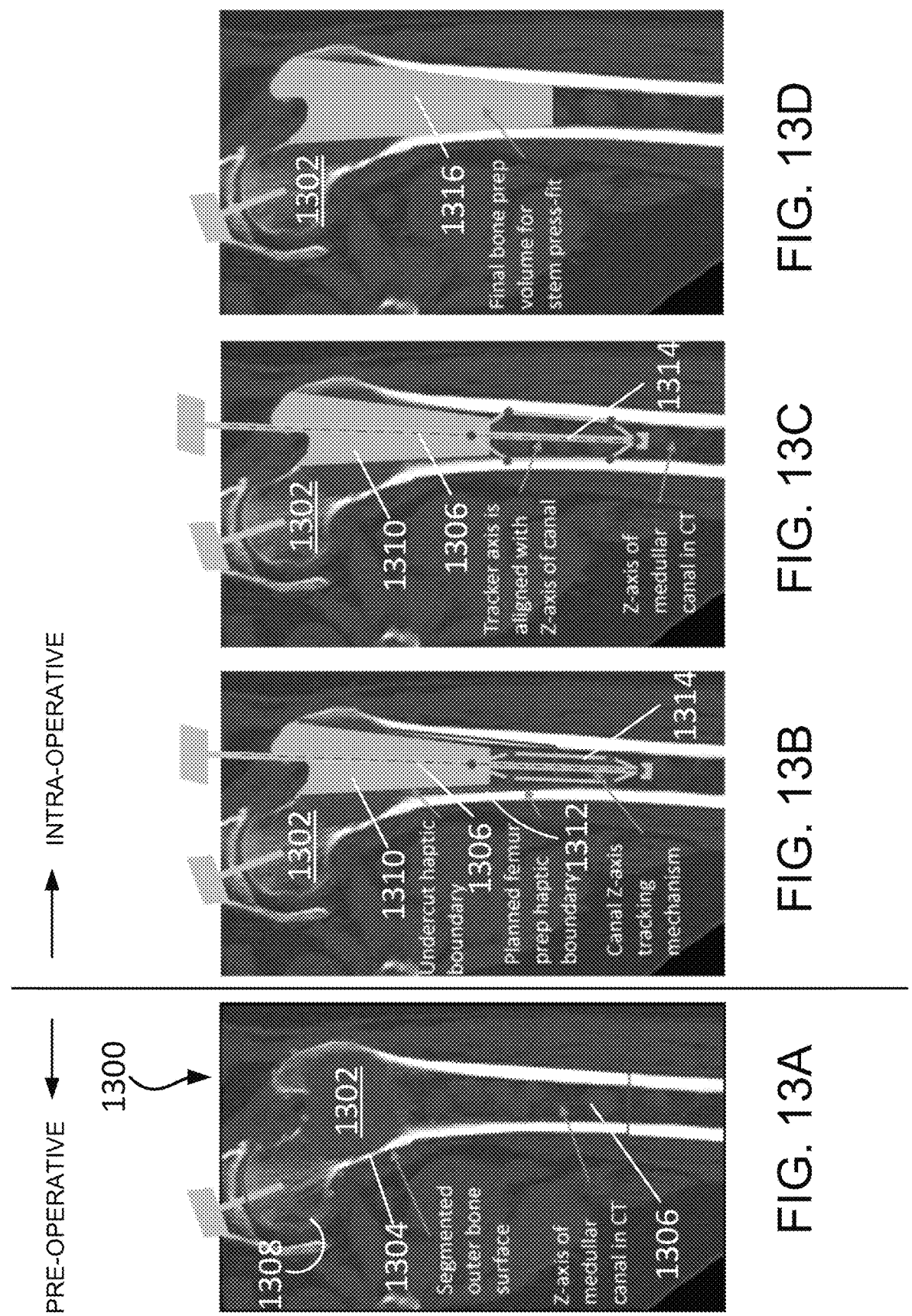
FIG. 13A depicts a pre-operative image of a proximal femur undergoing segmentation.
FIG. 13B depicts a proximal femur with the femoral canal partially resected, and with a registration tool extending into the femoral canal.
FIG. 13C depicts a proximal femur with the femoral canal partially resected, and with the registration tool extended into the femoral canal, and with the tool expanded to the internal bone surfaces.
FIG. 13D depicts a proximal femur with the femoral canal fully resected.

Another femur registration method 1200 is shown in FIGS. 12 and 13A-13D. As seen in FIG. 12, the registration method 1200 may include, at step 1202, segmenting an outer bone surface of the proximal femur, and determining the femoral canal axis or the femoral anatomic Z-axis of the femur canal in a bone model constructed from medical images of the proximal femur. Additionally, step 1202 may include picking a point-cloud on the proximal femur outer surface for bone registration. This particular femur registration method 1200 does not include segmentation of the inner bone surface. As seen in FIG. 13A, a medical image 1300 of a plurality of medical images are taken of a patient's proximal femur 1302. The outer bone surfaces 1304 of the proximal femur 1302 in the medical images 1300 are segmented, and a femoral anatomic Z-axis 1306 of the femur canal is determined from the plurality of medical images. The figure also shows a plurality of points 1308 of a point-cloud on the proximal femur 1302. The plurality of points 1308 are spaced along portions of the femoral head, femoral neck, and greater trochanter.

While step 1202 of the registration method 1200 takes place preoperatively, steps 1204 through 1208 take place intra-operatively. Step 1204 of FIG. 12 includes resecting the proximal femur with a burr of an end-effector within a smaller volume than the fully resected haptic volume for the implantation of the stem of a femoral implant component. The smaller volume of the resection of step 1204 is intended to clear the cavity for point picking. Additionally, at step 1204, a surgeon may insert a tracker mechanism into the medullar canal. As seen in FIG. 13B, an initial volume 1310 within the femoral canal is resected via a burr of an end-effector. The initial volume 1310 is less than the full resection volume 1312 that will be used for the implantation of the stem of the femoral implant component. After the initial volume 1310 is resected, a tracker mechanism or tool 1314 is inserted into the femoral canal. As seen in FIG. 13B, the tracker mechanism 1314 includes a distal expansion mechanism, a shaft extending proximally from the distal positioning mechanism, and a tracker at a proximal end of the tracker mechanism. The tracker mechanism 1314 may be inserted into the femoral canal such that the distal positioning mechanism extends past the initial volume 1310 and into the bone of the femoral canal.

Step 1206 of FIG. 12 may include aligning the tracker mechanism 1314 with the cortical bone surface on the interior side of the femur. Reference is made to FIG. 13C, which shows the tracker mechanism 1314 in a laterally expanded orientation within the femoral canal such that the shaft is generally parallel with the femoral anatomic Z-axis 1306. As seen in the figure, the distal positioning mechanism 1314 may include a plurality of members extending longitudinally (parallel with the shaft) that are configured to expand radially outward so as to contact the inner cortical bone surfaces of the femur 1302. The plurality of members may have a plurality of markers capable of being seen under medical imaging to verify the plurality of members are contacting the cortical bone surfaces of the femur. As seen in the figure, when the plurality of members contacts the cortical bone surface, the shaft extending proximally from the distal positioning mechanism is parallel to the femoral anatomic Z-axis 1306. In certain instances, the location of the bone contact points may be tracked inside the tracker mechanism 1314. The mechanism 1314 may include two, three, or more contact points capable of centering the tool in the canal so as to register the center point at any given position. In such an instance, a tool axis may not be needed. In certain instances, the contact points on the tracker mechanism 1314 could be spring expandable, and actively track and map the internal walls of the bone as the tool is inserted into the canal.

Turning back to FIG. 12, the registration method 1200 at step 1206 may also include running an iterative closest point (ICP) calculation with the existing point-cloud and the femoral anatomic Z-axis determination, and the registration transform may be updated accordingly.

Step 1208 of FIG. 12 may include finishing the bone preparation by removing the tracker mechanism 1314 and resecting the remaining portion of the femoral canal to the final resection volume, which may have been updated based on the registration transform. As seen in FIG. 13D, the proximal femur 1302 may be fully resected to the final resection volume 1316 for the implantation of the stem of the femoral implant component.

Figure 13E:
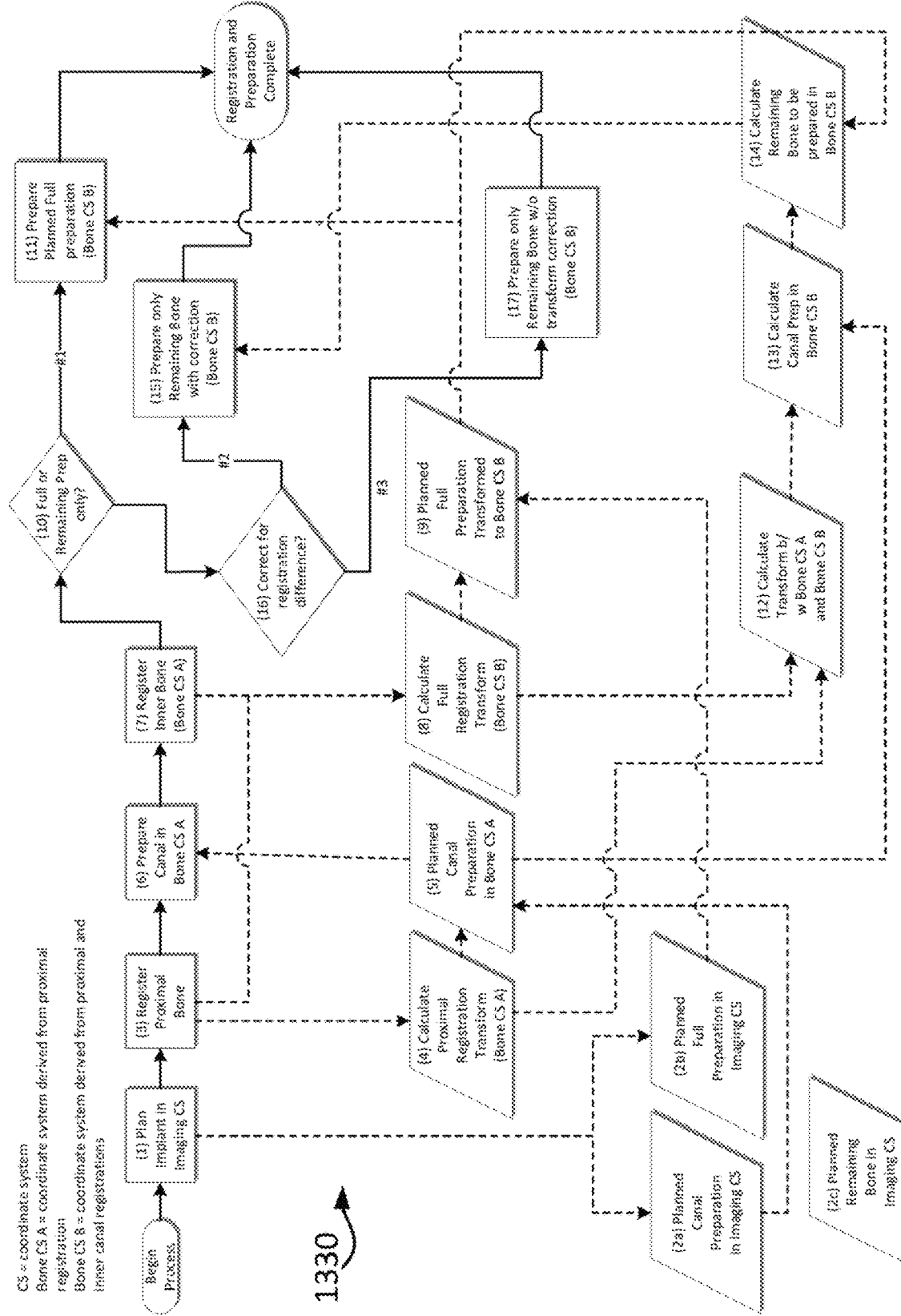
FIG. 13E depicts an exemplary flowchart for planning and performing a surgical procedure on a proximal femur.

Another femur registration method 1330 is shown in FIG. 13E. As seen in FIG. 13E, the registration method 1330 may include the following operations or steps. In certain instances, the method 1330 may include planning the placement of an implant relative to a computer model of a patient bone in an imaging coordinate system (1). The implant plan in (1) may provide the planned initial femur canal preparation (2a) (to be used in canal registration) and the planned full preparation (2b) (to receive an implant stem) in the imaging coordinate system since the two planned preparations of the femoral canal may be related to the overall implant plan. A difference (e.g., volume difference) between the full (2b) and canal (2a) preparation can also be calculated in the imaging space (2c).

Continuing on with the method 1330 in FIG. 13E, after the implant planning (otherwise known as preoperative planning) (1), the surgeon may register the proximal femur (3) using any known registration method. From the proximal femur registration (3), the proximal registration transform to bone coordinate system (Bone CS A) is calculated (4). Using the proximal registration transform from (4), the planned femur canal preparation from (2) is transformed to the Bone CS A (5). Knowing the femur canal preparation plan in Bone CS A from (5), the system can then prepare the canal in Bone CS A (6) by physically burring out the proximal canal of the femur according to the planned canal preparation determined in (2a).

With the proximal femoral canal burred-out or otherwise prepared, the surgeon may then register the inner bone (7) which is now exposed by the burring. The proximal registration in (3) may be combined with the inner bone registration in (7), to calculate a full bone registration transformation to Bone CS B (8). With the full bone transformation from (8), the full bone preparation plan from (2a) is transformed to Bone CS B (9).

The decision box in 10 defines where the design may be split between full preparation or remaining preparation only.

In instance #1: Prepare full bone preparation (ignoring previously prepared canal). Knowing the full preparation plan in Bone CS B from (9), the system can then prepare the proximal femur according to the full preparation plan in Bone CS B (11) by physically burring out the proximal femoral canal according to the full preparation plan from (2b). Registration and preparation of the bone is complete in this first instance.

Instance #2 or #3 will now be described.

The decision box in (16) defines where the design may be split between preparing remaining bone with or without correction for the transform between the proximal registration (Bone CS A) and full registration (Bone CS B).

Instance #2: Preparing remaining bone with transform correction. The difference between Bone CS A from (4) and Bone CS B from (8) is calculated. Knowing the transform difference above, the femur canal prep in Bone CS A (5) can be transformed to Bone CS B (13). The remaining bone in Bone CS B (14) may be calculated by subtracting the canal prep in Bone CS B (13) from the full planned preparation in Bone CS B (9). Knowing the remaining bone in Bone CS B, the system can then prepare the remaining bone in Bone CS B (15) by burring the remaining bone in the proximal femur canal according to the full preparation plan. Registration and preparation of the bone is complete in this second instance.

Instance #3: Preparing remaining bone without transform correction. The planned remaining bone from (2c) is transformed into Bone CS B knowing the transform from (8). The system can then prepare the assumed remaining bone in Bone CS B (17) with the assumption that the differences between Bone CS A and Bone CS B are minimal and any unprepared bone due to the difference will be floating and removable from the canal. Registration and preparation of the bone is complete in this third instance.

Figure 13F:
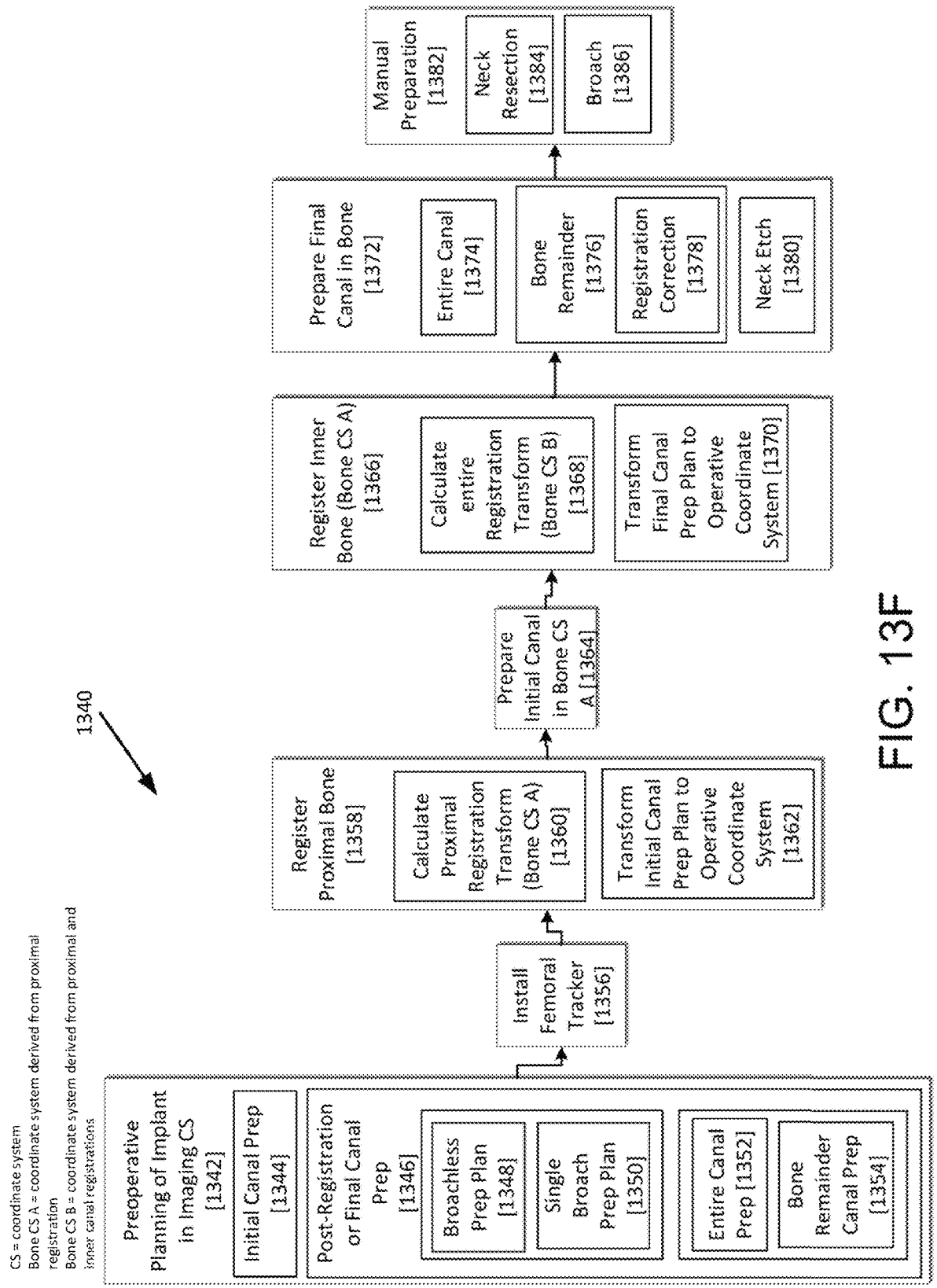
FIG. 13F depicts an exemplary flowchart for planning and performing a surgical procedure on a proximal femur.

Another femur registration method 1340 is shown in FIG. 13F. The first step 1342 of the method 1340 is preoperative planning the arthroplasty procedure such as a total hip replacement, for example. More particular, the step 1342 may include planning the implant placement of a femoral implant relative to the patient's femur in a preoperative coordinate system. This may include selection of implant size, shape, type, and manufacturer, among other variables. Additionally, the preoperative planning of the implant may include virtually positioning and orienting an implant model (e.g., virtual three-dimensional implant model representative of a physical implant provided by the manufacturer) relative to a patient bone model (e.g., virtual three-dimensional bone model representative of the patient's physical femur). The implant model may be provided by the manufacturer. The patient bone model may be generated from preoperative scans of the patient's leg. The patient bone model may be generated from a statistical model, a generic model, or other type of model that represents or approximates the shape, size, and configuration of the patient's physical bone.

Once a final implant position and orientation is determined to achieve a particular surgical outcome, a surgical plan can be determined to achieve the final implant position and orientation. For instance, the final implant position and orientation will determine the corresponding position and orientation of bone to be removed from the canal of the femur so the stem of the femoral implant can be accurately positioned therein in order to achieve the desired or planned final implant position and orientation.

As part of the preoperative planning step 1342, the method 1340 may also include planning or determining an initial canal preparation plan, at step 1344. The initial canal preparation plan may be also be called a first bone removal plan of the surgical plan. In the actual, physical surgery, the femoral canal will be prepared by, for example, being bored longitudinally in the place where the stem of the femoral implant will eventually be positioned. As described herein, the femoral canal will be prepared in at least two steps: initial canal preparation for registration purposes; and final canal preparation for implantation of the femoral implant. The step 1344 of determining an initial canal preparation plan may include determining coordinate locations for a partial bone removal of the femoral canal. The step 1344 may also include determining a cut path for a surgical device to facilitate removal of the bone from the femoral canal. The coordinate locations and the cut path may be defined in a coordinate system relative to preoperative bone model used for planning the final implant position and orientation. As described herein, the initial canal preparation plan may only include a partial canal preparation that includes less bone removal (e.g., less depth, less diameter) than a full canal preparation needed for implantation of the stem of the femoral implant.

One reason for the initial canal preparation plan to be a partial bone removal from the femoral canal as opposed to a full preparation of the femoral canal is that partial bone removal allows for an additional registration step involving data from the femoral canal that takes place prior to the full preparation of the femoral canal. This additional registration of the internal femoral canal may lead to a more accurate registration process and thus a more accurate full preparation of the femoral canal. For at least these reasons, the preoperative planning of the bone removal may be split into at least a first bone removal plan including a plan for partial removal of bone from the femoral canal (for registration purposes), and a second bone removal plan including a plan for full removal of bone from the femoral canal to achieve the final implant position and orientation that was preoperatively planned.

The next step 1346 of the method 1340 may include planning or determining a final canal preparation plan. The final canal preparation plan may be also be called a second bone removal plan of the surgical plan. Alternatively, the final canal preparation plan may be called a post-registration canal preparation plan. This step 136 of the method 1340 includes a plan for the preparation of the femoral canal beyond the initial canal preparation from step 1344. In certain instances, this step 1346 includes the plan for preparation of the femoral canal so the canal is sufficiently bored out to receive the stem of the femoral implant.

The step 1346 may include a number of sub-steps such as the following: planning a broachless femoral preparation plan, at step 1348; planning a single broach preparation plan, at step 1350; planning an entire canal preparation plan, at step 1352; and planning only a bone remainder canal preparation plan, at step 1354. Each of these sub-steps will be described in turn.

In determining the final canal preparation plan, at step 1346, the method may include a broachless preparation plan, at step 1348. In this step 1348, the femoral canal is planned to be prepared fully robotically without manual broaching by a surgeon. In this way, no portion of the bone is left for manual preparation by the surgeon; stated differently, the entire final preparation plan (whether entire canal prep or bone remainder canal prep only) is robotically prepared.

As an alternative to a broachless preparation plan, the final canal preparation plan may include a single broach preparation plan, at step 1350. In this step 1350, the femoral canal is planned to be prepared partially by robotic control, with a final broach performed manually by a surgeon. In this way, a small portion of bone removal needed to implant the implant is left off of the final canal preparation plan so that the surgeon can manually perform a final broach. In traditional (non-robotic) surgery, a surgeon may use a series of broaches of increasing size to prepare the femoral canal. In this case, a final (single) broach may be utilized since the final canal preparation plan was performed robotically without the need for broaches. Permitting the surgeon to perform a final broach of the femoral canal enables the surgeon to make any final adjustments to implant fit, and may also lessen the chance of removal of too much bone from the canal via robotic preparation since the surgeon could trial the implant fit while broaching.

Separate from determine whether the final canal preparation plan will include a broachless plan, at step 1348, or a single broach plan, at step 1350, the final canal preparation plan 1346 may also include a determination of whether to plan the preparation of the entire femoral canal (including bone removal from the area of the initial canal preparation), at step 1352, or whether to plan the preparation of only the bone remainder of the bone canal (bone that was not removed by the initial canal preparation), at step 1354.

At step 1352, the final canal preparation plan may include planning the preparation of the entire femoral canal. This may include preparation of the femoral canal that was previously prepared by the initial canal preparation plan. The difference being that a second registration will have taken place that includes more registration data as compared to the first registration (e.g., registration data from both the inner canal and exterior surface of femur), possibly increasing the accuracy of the mapping of the surgical plan from the preoperative coordinate system including the second bone removal plan to the operative coordinate system. Thus, there may be improvements to the accuracy of the locations of bone removal following the second registration. Therefore, planning preparation of the entire femoral canal would benefit by re-milling or re-removing the portions of the bone that were initially planned to be removed in the initial canal preparation plan.

In addition to re-removing the portions of bone that were initially planned to be removed in the initial canal preparation plan, at step 1344, the planning for the preparation of the entire femoral canal, at step 1352, may include planning coordinate locations for bone removal of the remaining portions of bone sufficient for implantation of the stem of the femoral implant. It is noted that a final canal preparation plan that includes the preparation of the entire femoral canal according to step 1352 may include a broachless preparation plan according to step 1348 or a single broach preparation plan according to step 1350.

At step 1354, the final canal preparation plan may include planning the preparation of only the bone remainder of the femoral canal. This may include preparation of the femoral canal that was not previously prepared by the initial canal preparation plan. In certain instances, there may not be significant accuracy improvement from the second registration; therefore, the increased time it takes to re-prepare the bone as done in the entire canal preparation plan, at step 1352, may not be worth marginal increase in accuracy. If there was, however, a substantial increase in accuracy improvement from the second registration, this may indicate that preparation of the entire canal is beneficial.

The planning for the preparation of only the bone remainder of the femoral canal, at step 1354, may include planning coordinate locations for bone removal of the remaining portions of bone sufficient for implantation of the stem of the femoral implant. It is noted that a final canal preparation plan that includes the preparation of only the bone remainder of the femoral canal according to step 1354 may include a broachless preparation plan according to step 1348 or a single broach preparation plan according to step 1350.

In one instance, the final canal preparation plan may include a plan to prepare the entire femoral canal, according to step 1352, and with a broachless preparation plan, according to step 1348. In one instance, the final canal preparation plan may include a plan to prepare the entire femoral canal, according to step 1352, and with a single broach preparation plan, according to step 1350. In one instance, the final canal preparation plan may include a plan to prepare only the bone remainder of the femoral canal, according to step 1354, and with a broachless preparation plan, according to step 1348. In one instance, the final canal preparation plan may include a plan to prepare only the bone remainder of the femoral canal, according to step 1354, and with a single broach preparation plan, according to step 1350.

After the preoperative planning, at step 1342, is complete, the surgery may commence. As part of the surgery, a femoral track may be installed or coupled to the patient bone, at step 1356. The femoral tracker provides a reference to the surgical navigation system so that the surgical robot is spatially aware of the proximity of the patient's bone in the operative coordinate system.

Once the tracker is installed, the proximal bone of the femur is registered (assuming it is already dislocated from the hip), at step 1358. More particularly, the femoral head may be registered by collecting, logging, capturing points with a surgical device (e.g., tracked pointer, end effector of robotic arm) on the exterior surface of the femoral head. The captured points (also known as registration data) may be stored in a point-cloud of data, and may be spatially oriented relative to each other according to their locations on the exterior surface of the femoral head. A sufficient number of points are collected in order to approximate the shape of the surface to be registered.

The surgical navigation system is capable of spatially locating the captured points relative to the femoral tracker. The internal canal preparation plan, from step 1344, is defined relative to the preoperative bone model that represents the patient's femur. Thus, the goal of registration is to accurately transform or map the preoperative surgical plan (e.g., internal canal preparation plan) to the operative coordinate space relative to the actual femur in the same position and orientation that the surgical plan was in relation to the preoperative bone model. In this way, the surgical robotic arm and the surgical plan will be in the same coordinate system, and the robotic arm can be operated to perform the surgical plan on the actual patient bone so as to accomplish the preparation of the femur as planned preoperatively at step 1342.

Once the points are captured on the proximal femur, the computer of the system calculates a registration transform based on the captured points on the proximal femur, at step 1360. The registration transform is a mathematical algorithm mapping the coordinate points associated with the initial canal preparation plan from the preoperative coordinate system to the captured points on the physical femur in the operative coordinate system. From the registration transform, the surgical plan including the initial canal preparation plan, from step 1344, is transformed or mapped to the operative coordinate system, at step 1362.

With the initial canal preparation plan defined in the operative coordinate system, the method 1340 now includes preparing the initial canal in the proximal femur according to the initial canal preparation plan, at step 1364. As described with reference to step 1344, the initial canal preparation plan may include a partial preparation of the femoral canal that is less than full preparation of the femoral canal for implantation of the stem of an implant. For example, the robotic arm of the surgical robot may be used to bore or mill through the greater trochanter and into the central canal (i.e., femoral canal). The bone may be, for example, milled distally until the inner surfaces of the cortical bone are reached. The cortical bone is much harder than the spongy bone leading to the cortical bone; thus, it is easily identified during the procedure. The inner cortical bone is also easily identified in the preoperative bone model. Therefore, the inner cortical bone provides areas for registration that can be combined with the registration points on the proximal femur. The combined points may be advantageous for producing a more accurate registration transform since the points are spaced apart from each other, and are on different surfaces of the bone (inner and outer). Registration of the proximal femur and central canal is possible since the femoral head is still intact (i.e., not yet resected).

After the initial, partial preparation of the central canal, the method 1340 may include registering the inner canal, at step 1366. The inner canal may be registered in any number of ways. As an example, a surgical device (e.g., tracked probe, end effector of surgical arm, any of the devices previously described) may be used to collect, log, or capture points on the internal cortical bone surface of the femoral canal. As another example, a surgical device (e.g., tracked probe, end effector of surgical arm, any of the devices previously described) may be used to collect, log, or capture orientation data associated with the femoral canal. Orientation data may be an axis, such as a longitudinal axis of the femoral canal. The captured points and/or the orientation data may be defined as registration data. The registration data may be stored as a point-cloud of data in a computer.

Once the inner bone is registered, the method 1340 may include calculating a registration transform using the registration data from the femoral canal (e.g., captured points) and the registration data from the exterior surface of the proximal femur (e.g., captured points and/or orientation data). Since the second registration transform, at step 1368, includes additional data from the inner canal, as compared to the first registration, at step 1360, the registration transform may have improved accuracy as compared with the first registration transform.

At step 1370, the method 1340 may include transforming or mapping the final canal preparation plan, from step 1346, to the operative coordinate system based on the calculated registration transform of step 1368. This step maps the coordinate locations and/or instructions for bone removal for the final canal preparation plan from the preoperative coordinate system to the operative coordinate system in the same position and orientation as the surgical plan was oriented and positioned relative to the preoperative bone model. In this way, the final canal preparation plan is in the operative coordinate system with the patient's femur and the surgical robot.

Following transforming the final canal preparation plan to the operative coordinate system, the method 1340 may include, at step 1372, preparing the femur according to the final canal preparation plan. How the femur is prepared depends on the parameters of the final canal preparation plan as preoperatively defined at step 1346. For a preoperatively planned preparation of the entire canal, at step 1352, the physical preparation of the entire canal will take place at step 1374. In this step, the entire femoral canal may be milled or otherwise removed. This includes milling the previous portion of the bone that was previously removed at step 1364, as well as preparing the bone remainder that was not previously removed. As described previously, the initial canal preparation, at step 1364, was only a partial preparation of the femoral canal for the purpose of registration of the bone surfaces or axes associated with the canal. The final preparation of the femur canal is to remove sufficient bone to receive the stem of the femoral implant. As described previously, the entire canal preparation may take advantage of the second registration that involves data from the exterior and interior portions of the femur. Thus, the entire femur preparation may still remove bone from the initially prepared portion of the femur since the coordinates may have changed due to the subsequent registration.

For a preoperatively planned preparation of only the bone remainder of the femoral canal, at step 1354, the physical preparation of the bone remainder will take place at step 1376. In this step, the bone remainder or portion of the femur canal that was not previously removed is prepared (i.e., removed) in order to make way for the stem of the femoral implant. This may include milling down into the femoral canal only the portions of bone that were not previously removed. This step may include a sub-step 1378 of deciding whether to use the first registration transform that was calculated with points on the exterior of the proximal femur, or the second registration transform that was calculated with points on the exterior of the proximal femur and femoral canal data taken from the femoral canal.

Following the physical preparation of the femoral canal, and prior to the resection of the femoral head, the method 1340 may include, at step 1380, marking the femoral neck in preparation for a manual resection of the neck. In a robotic hip surgery, the femoral tracker may be coupled to the femoral head. And thus robotic navigation will cease to function when the femoral head is resected as the tracker will no longer be able to correctly identify the location of the remaining portion of the femur. For at least this reason, the femoral neck is marked (e.g., etched) via robotically controlled and navigated guidance to provide guidance to the surgeon when manually resecting the neck. The femoral neck mark may be an etch or burr into the bone along the planned resection plane. The etch or burr may be a cut into the bone that does not fully resect the bone. That is, the cut into the bone may not extend through the cortical bone. Instead, the cut provides a visible mark for the surgeon to use or verify correct placement of a saw blade.

The manual preparation of the femur is shown at step 1382. The neck resection is shown at step 1384 and may include the surgeon using a bone saw with or without additional guides or jigs to manually resect the femoral head at the neck. If the final canal preparation included a single broach preparation plan, at step 1350, the surgeon may then broach the femoral canal at step 1386. Since the navigated robot prepared the rest of the femoral canal preparation, the only remaining part of the manual preparation of the canal prior to implant trialing and implant fitting is for the surgeon to use a single broach to remove the last remaining portions of the bone. This provides the surgeon with an opportunity to make minor adjustments to the femoral canal and/or trial the implant as he or she broaches to provide an accurate implant fit.

The following is a description of an exemplary system implementing the method 1340 of FIG. 13F. The system may register a surgical device, such as a surgical robot, and a bone of a patient, such as a femur. The femur may include an exterior surface such as the femoral head, neck, and greater trochanter. The femur may also include an inner canal or femoral canal. The surgical device and the femur are in the same operative coordinate system (e.g., operating room). The system may include at least one computing device in communication with a surgical navigation system and the surgical device. The surgical navigation system may include a tracking device and at least one tool (e.g., tracked probe, tracking arrays positioned on surgical robot and/or patient) configured to be tracked in its movement by the tracking device. The surgical navigation system is also configured to track the surgical device and/or a tracking array on the surgical device. The at least one computing device stores a surgical plan in a virtual coordinate space. The surgical plan may include data from the preoperative planning of the implant placement from step 1342 of the method 1340 of FIG. 13F. The surgical plan may also include the initial canal preparation plan, also known as the first bone removal plan, at step 1344 of the method 1340 of FIG. 13F. The surgical plan may also include the final canal preparation plan, also known as the second bone removal plan, at step 1346 of the method 1340 of FIG. 13F. The second bone removal plan may include the plans for a broachless preparation plan at step 1348, a single broach preparation plan at step 1350, an entire canal preparation plan at step 1352, and/or the bone remainder preparation plan at step 1354, among other steps, such as the neck etch plan.

The at least one computing device is configured to do the following: a) receive external bone registration data corresponding to locations on the exterior surface of the femur. This bone registration data may correspond to the registration of the proximal bone from step 1358 of the method 1340 of FIG. 13F. For instance, the surgeon may capture, collect, or log points on the patient's proximal femur (e.g., head, neck) using a tracked probe that is tracked by the surgical navigation system in the operative coordinate system. Next, the at least one computing device is configured to: b) calculate a first registration transform based on the external bone registration data. This step may correspond to step 1360 of the method 1340 of FIG. 13F. The at least one computing device may then: c) transform the first bone removal plan of the surgical plan to the operative coordinate system based on the first registration transform. This step may correspond to step 1362 of the method 1340 of FIG. 13F. The at least one computing device may also: d) receive internal bone canal registration data corresponding to at least one of location or orientation data from the inner canal of the femur. This step may correspond to step 1366 of the method 1340 of FIG. 13F. For instance, the surgeon may capture, collect, or log points on the patient's inner femoral canal that was partially prepared for the purpose of accessing and registering to provide additional registration data that can be used for the final preparation of the femur canal.

The at least one computing device may also: e) calculate a second registration transform based on both the external bone registration data and the internal bone registration data. This step may correspond to the step 1368 of the method 1340 of FIG. 13F. And the at least one computing device may also: f) transform the second bone removal plan of the surgical plan to the operative coordinate system based on the second registration transform. This step may correspond to step 1370 of the method 1340 of FIG. 13F.

The exemplary system described in the previous paragraphs may be additionally or alternatively described as a computer implemented method of registration of a surgical device and a patient bone (e.g. femur). The computer implemented method may include the steps described by the at least one computer in steps a) through f), among others.

The exemplary system described in the previous paragraphs may also be additionally or alternatively described as one or more tangible computer-readable storage media storing computer-executable instructions for performing a computer process on a computing system, such as the at least one computing device described in the previous paragraphs. The computer process may include the steps a) through f), among others, described with reference to the at least one computing device.

C. Tracking and Registration of Pelvis

1. Overview

In step S4 of FIG. 5, an acetabular tracking array is attached to the pelvis 12 to enable the tracking device 8 to track motion of the pelvis 12. In step S5, a checkpoint may be attached to the pelvis 12 for use during the surgical procedure to verify that the acetabular tracking array has not moved in relation to the pelvis 12. The checkpoint can be, for example, a checkpoint as described in U.S. patent application Ser. No. 11/750,807 (Pub. No. US 2008/0004633), filed May 18, 2007, and hereby incorporated by reference herein in its entirety.

Figure 6:
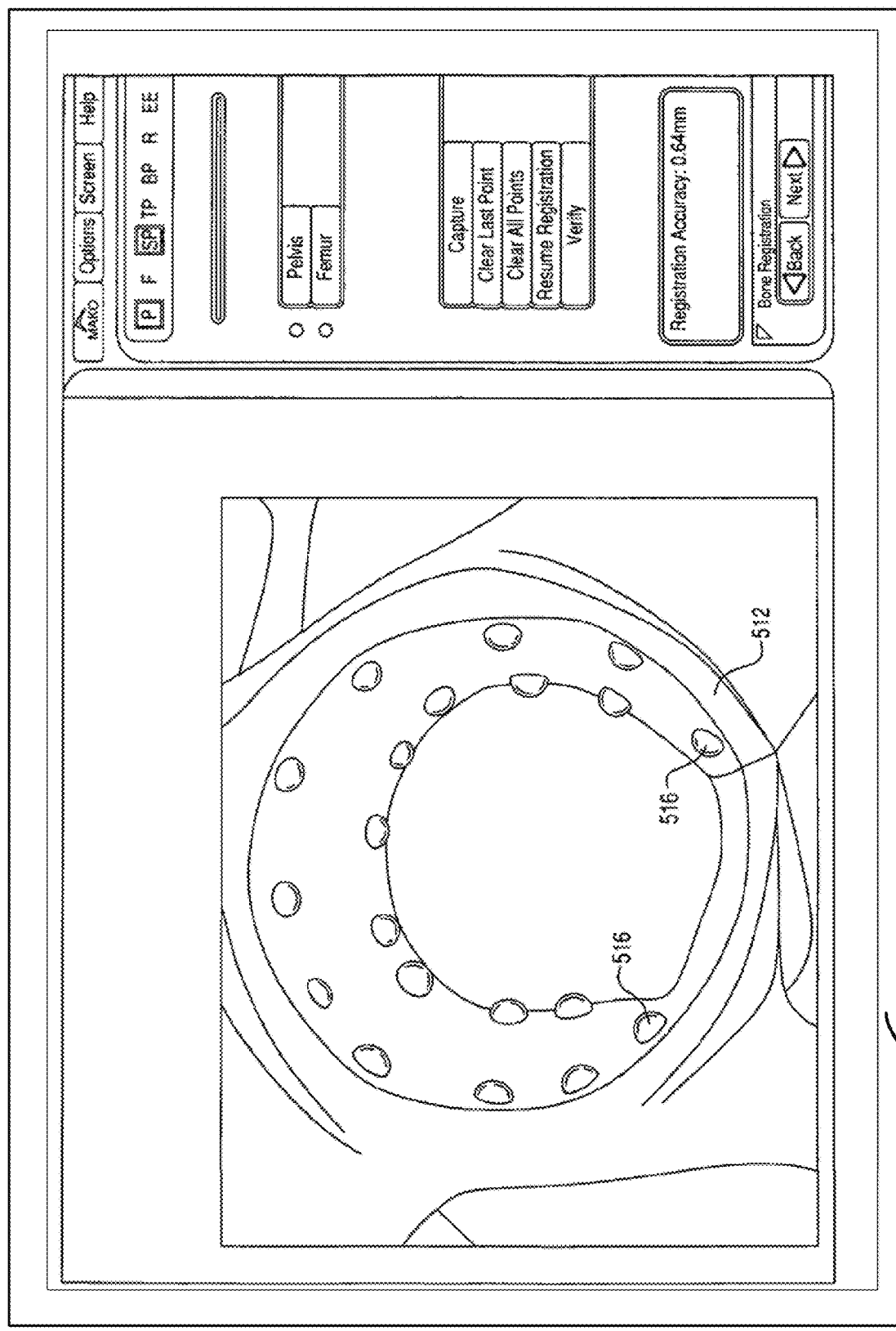
FIGS. 6 and 7 illustrate an embodiment of a pelvic registration method shown on a display screen.

In step S6, the pelvis 12 is registered to correlate the pose of the pelvis 12 (physical space) with the three-dimensional model 512 of the pelvis 12 in the navigation system 7 (image space). In certain embodiments, as shown in FIG. 6, registration is accomplished using the tracked navigation probe 56 to collect points on the pelvis 12 (physical space) that are then matched to corresponding points on the three-dimensional model 512 of the pelvis 12 (image space). In certain embodiments, registration may be accomplished using a tool that is coupled to the end effector 40 of the robotic arm 30. In certain embodiments, registration may be accomplished with any tool or device that is tracked with the navigation system 7. Two methods of registering the three-dimensional model 512 of the pelvis (image space) and the pelvis 12 (physical space) are described in the subsequent sections of this application.

2. Pelvic Registration Method

As shown in FIG. 6, the display device 9 may show the representation 512 of the pelvis 12, including one or more registration points 516. The registration points 516 help the surgeon understand where on the actual anatomy to collect points with the tracked probe. The registration points 516 can be color coded to further aid the surgeon. For example, a registration point 516 on the pelvis 12 to be collected next with the tracked probe can be colored yellow, while registration points 516 that have already been collected can be colored green and registration points 516 that will be subsequently collected can be colored red. After registration, the display device 9 can show the surgeon how well the registration algorithm fit the physically collected points to the representation 512 of the pelvis 12.

Figure 7:
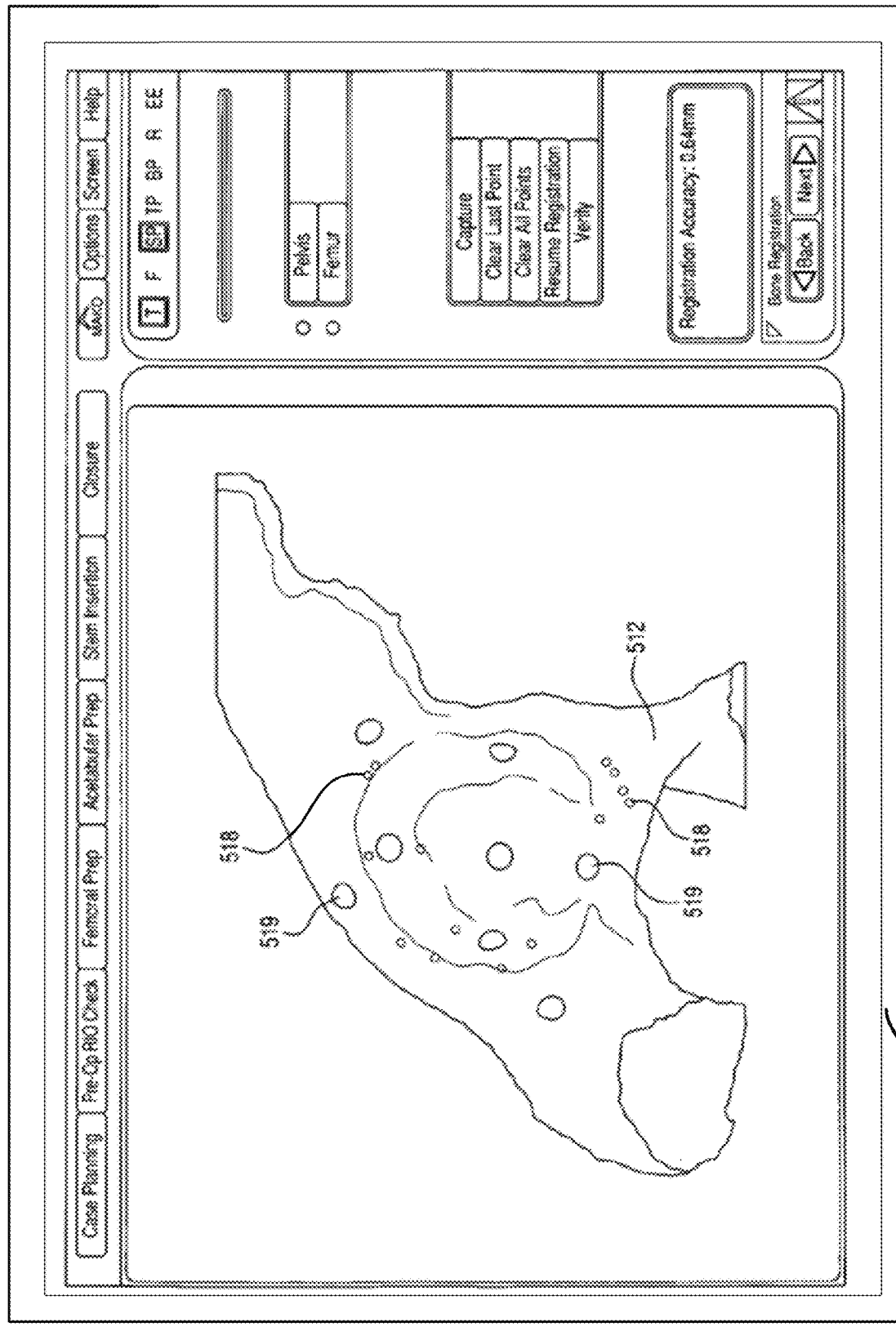

For example, as shown in FIG. 7, error points 518 can be displayed to illustrate how much error exists in the registration between the surface of the representation 512 and the corresponding surface of the physical pelvis 12. In one embodiment, the error points 518 can be color coded, for example, with error points 518 representing minimal error displayed in green and error points 518 representing increasing amounts of error displayed in blue, yellow, and red. As an alternative to color coding, error points 518 representing different degrees of error could have different shapes or sizes. Verification points 519 can also be displayed. The verification points 519 illustrate to the surgeon where to collect points with the tracked probe to verify the registration. When a registration point 519 is collected, the software of the navigation system 7 displays the error (e.g., numerically in millimeters) between the actual point collected on the anatomy and the registered location of the representation 512 in physical space. If the registration error is too high, the surgeon re-registers the pelvis 12 by repeating the registration process of step S6.

This type of registration method requires the surgeon to continually switch his or her focus from the display device 9 showing the representation 512 of the pelvis 12, including one or more registration points 516, to the patient's physical pelvis 12 in order to collect accurate points. Switching focus takes time, and accurately estimating where the registration points 516 are on the patient's physical pelvis 12 takes even more time. In such a registration method described in this section, it may take at least forty-three points to complete an accurate registration.

Additional pelvic registrations methods S6 involving determining a center of rotation of the acetabulum based on pre-operative images and intra-operative point collection are described in related application PCT/US2017/049466, filed Aug. 30, 2017, which is hereby incorporated by reference in its entirety into the present application. The methods described may reduce the total number of collected points as compared with the previously described registration method. For example, with the method described in this section, a surgeon may complete an accurate registration with thirty-two points or less. Additionally, much of the registration described in this section is a region-based point collection, as opposed to a point-based point collection. In a region-based point collection, the surgeon is permitted to collect points within a region of the patient's bone, as opposed to an exact point as identified on the three-dimensional bone model 512. This permits the surgeon to focus on the patient's anatomy, and collect points within the permitted region on the bone without having to switch his or her focus to the display screen 9 and back to the patient's physical pelvis 12. Collecting points within a permitted region increases accuracy as it is easier for the surgeon to collect points within a region encompassing many possible locations of permissible points, as compared with a single permissible point.

3. Pelvic Registration Method Utilizing a Z-Axis of an Imaging Table and a Z-Axis of an Operating Table.

Reference is made to FIGS. 14A-14B and 15A-15C, which illustrates a pelvic registration method 1400 utilizing acetabular center of rotation data and patient positioning data from the patient during a pre-operative image scan (e.g., CT, MRI) and while in the operating room. More particularly, the registration method 1400 assumes an orientation of a patient lying, for example, supine on an imaging table for a pre-operative image scan (e.g., CT, MRI) is the same or similar to an orientation of the same patient lying in the same position (e.g., supine in this example) on an operating room table. This patient orientation data or patient positioning data may be used in conjunction with acetabular center of rotation data, among other data, that may be determined from the pre-operative image scans and from capturing points on the patient's acetabulum intra-operatively in registering a three-dimensional bone model of the patient's pelvis with the patient's physical pelvis in the operating room.

Figure 14A:
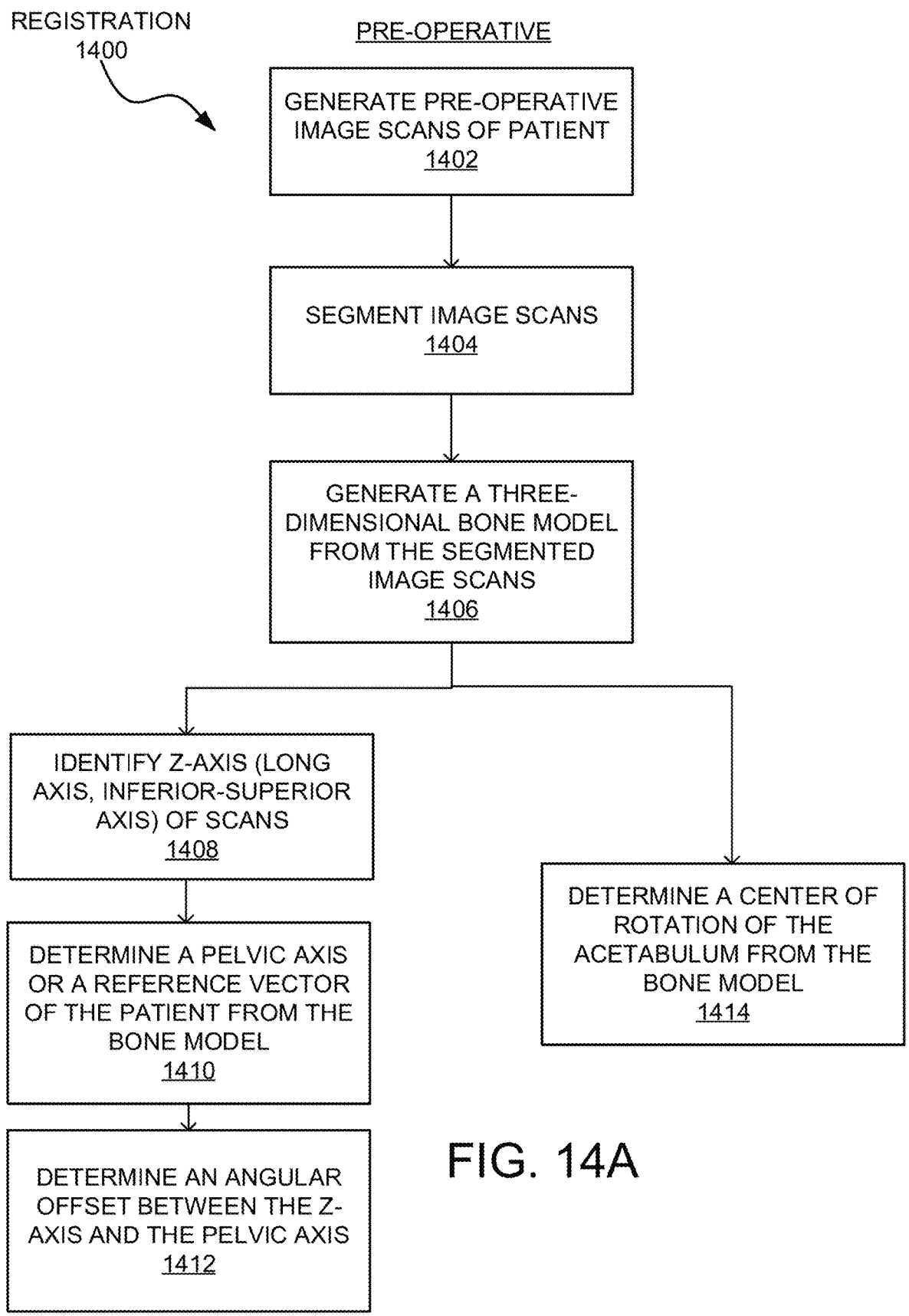
FIG. 14A illustrates pre-operative steps of a registration method utilizing information from a patient's orientation on an imaging table.
Figure 14B:
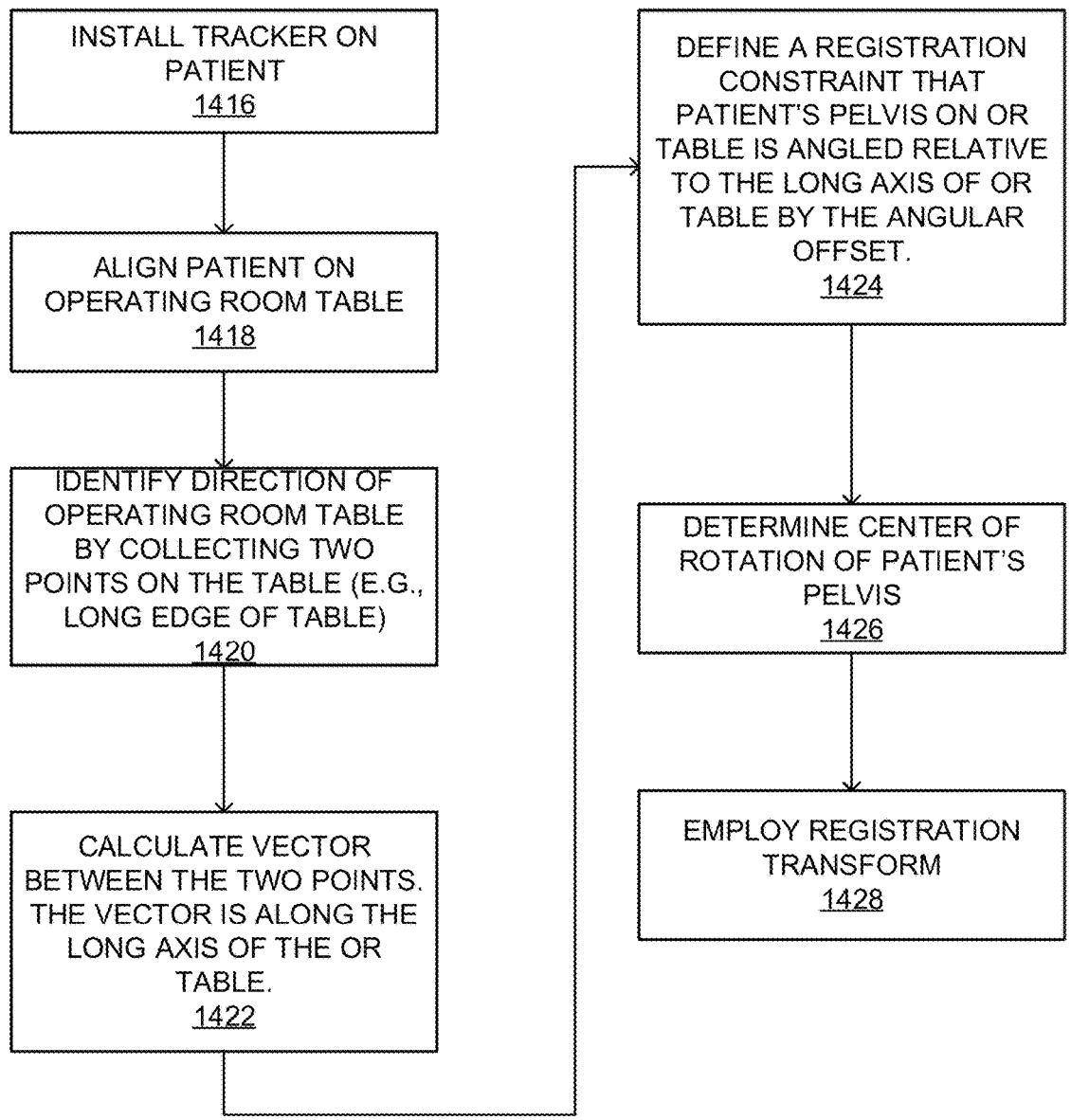
FIG. 14B illustrates intra-operative steps of a registration method utilizing information from a patient's orientation on an imaging table.

To begin, reference is made to FIGS. 14A and 14B, which illustrate exemplary steps of the registration method 1400. At step 1402 of FIG. 14A, the registration method 1400 may include generating pre-operative image scans of a patient. The image scans may be generated via a variety of imaging modalities including computed tomography (CT), magnetic resonance imaging (MRI), and X-ray, among others. To generate the image scans, a patient 1500 lying supine on an imaging table 1502 may be imaged via an imaging arm 1504 of an imaging machine 1506, as seen in FIG. 15A. At step 1404 of the registration method 1400 of FIG. 14A, the image scans may be segmented along the bone contour lines of the images. Once all the image scans are segmented, a three-dimensional bone model of the diseased area (e.g., ilium and femur) may be generated from the segmented image scans, at step 1406 of FIG. 14A. As an alternative to generating a three-dimensional bone model from the segmented image scans, a generic 3D bone model or statistical 3D bone model being representative of the patient bone may be generated.

At this point, the pre-operative steps of the registration method 1400 may diverge. Steps 1408, 1410, and 1412 may refer to the patient positioning data portion of the registration method 1400, whereas step 1414 may refer to the center of rotation calculation portion of the method 1400.

At step 1408 of FIG. 14A, the Z-axis, long axis, or superior-inferior axis may be identified from the scanned images or from the three-dimensional bone model. As seen in FIG. 15A, the Z-axis 1508 extends longitudinally down the table and from the patient's 1500 head to toes. The Z-axis 1508 may be identified in the scanned images as the axis the imaging table 1502 extends relative to the imaging arm 1504. For example, in a CT scan, the imaging table 1502 may be motorized so as to translate the table 1502 and patient 1500 positioned thereon along the Z-axis 1508 through an opening or through-way 1510 of the imaging arm 1504. In this orientation, the scans may be oriented perpendicular to the Z-axis 1508. The Z-axis 1508 may be identified in a coordinate system with the bone model.

At step 1410 of FIG. 14A, the registration method 1400 may include determining a pelvic axis 1512 (or a reference vector) of the patient 1500 from the scanned images or the bone model. The pelvic axis 1512 may be an axis bisecting the patient's pelvis between the pubic symphysis and generally equidistant between the pair of anterior superior iliac spines on the opposing ilium. Various methods described herein or known in the art may be used to determine the pelvic axis 1512.

At step 1412 of FIG. 14A, the registration method 1400 may include determining an angular offset between the Z-axis 1508 and the pelvic axis 1512. The angular offset 1514 may be seen in FIG. 15C, which will be discussed subsequently.

At step 1414 of FIG. 14A, the registration method 1400 may include determining a center of rotation of the acetabulum from the bone model. Determining the center of rotation may be done by any method described herein or any method known in the art. An example method of determining a center of rotation of a patient's acetabulum in a bone model generated from pre-operative images is described in PCT/US2017/049466, filed Aug. 30, 2017, which is hereby incorporated by reference in its entirety into the present application. Another example method of determining a center of rotation of a patient's acetabulum is via a kinematic analysis or motion analysis of the patient's femur relative to the pelvis.

Reference is made to FIGS. 14B and 15B, which illustrate the steps of the registration method 1400 that may occur intra-operatively. At step 1416 of FIG. 14B, the registration method 1400 may include installing a tracker on the patient's pelvis. As seen in FIG. 15B, the patient 1500 is in an operating room, lying supine on an operating room table 1520. The patient 1500 may also lay in a lateral decubitus position on the table 1520, and it can reasonably be assumed that going from supine to lateral decubitus is approximately a pure rotation about the long axis of the patient 1500. A robotic arm 1518 may be situated proximate the operating room table 1520. As seen in the figure, the tracker 1516 may be installed on the diseased side of the pelvis.

At step 1418 of FIG. 14B, the registration method 1400 may include positioning or aligning the patient 1500 on the operating room table 1520, as seen in FIG. 15B, in the same orientation as the patient was lying on the imaging table 1502. At step 1420, the registration method 1400 may include collecting two points 1522 on the operating room table 1520 along the long edge 1524 of the table 1520. A vector 1526 may be calculated between the two points 1522, at step 1422 of the method 1400. This vector 1526 may be analogous to the Z-axis 1508 of the scanned images in that the patient 1500 is lying in a supine position in likely the same orientation on the imaging table 1502 and the operating room table 1520. The vector 1526 may be determined and saved by the system in a common coordinate system with the positioning data for the tracker 1516. Additionally, or alternatively, a pointer or tracked probe may be used to identify the table axis. For instance, the pointer may be positioned in space so it is aligned with the long edge 1524 of the table 1520, and the system may capture the axis of the pointer. Additionally, or alternatively, the pointer could be aligned with the patient by, for example, placing the pointer along the midline of the patient with the pointed tip facing the patient's head. This method would also work with the patient lying on his or her side.

Step 1424 of the registration method 1400 of FIG. 14B may include defining a registration constraint that the patient's pelvis, on the operating room table 1520, is angled relative to the vector 1526 (or the long axis of the OR table 1520) by the angular offset 1514 as shown in FIG. 15C. The angular offset 1514 may be defined as an angle between the Z-axis 1508 and the pelvic axis 1512, or the angular offset 1514 may be defined as an angle between the vector 1526 on the OR table 1520 and the pelvic axis 1512 (assuming the vector 1526 and the pelvic axis 1512 are in a common coordinate system).

At step 1426 of FIG. 14B, the registration method 1400 may include determining a center of rotation of the patient's pelvis. The center of rotation 1528 is shown in FIG. 15B. This step 1426 may be accomplished via any method known in the art, and may be accomplished via the method described in PCT/US2017/049466, filed Aug. 30, 2017, which is hereby incorporated by reference in its entirety into the present application. In the aforementioned PCT application, the method describes picking points on the patient's acetabulum and forming a sphere based on the points. From the sphere, a center of rotation can be determined.

Once the center of rotation is found, at step 1426, and the registration constraint correlating to the angular offset is found, at step 1424, the registration transform may be employed at step 1428 of FIG. 14B. The registration transform merges the bone model (determined from pre-operative image scans of the patient's body) with the patient's physical body on the operating room table 1520 such that the robotic arm 1518 of FIG. 15C may be used to operate on the patient's body in a controlled manner and according to a pre-determined plan.

Knowing the center of rotation of the patient's pelvis, at step 1426, effectively locks the position of the pelvis in a coordinate system during the registration transform. Knowing only a single fixed point (center of rotation), however, means that the pelvis is unconstrained from rotating along three axes in this coordinate system. Thus, more information is needed to merge the bone model and the physical pelvis. The registration transform may use the registration constraint, of step 1428, by locking the orientation of the patient's pelvis relative to the vector 1526 during registration. Since the vector 1526 includes coordinates in three directions (x,y,z), the orientation of the pelvis may be determined when combining the information from the vector 1526 and the center of rotation 1528.

Figure 14C:
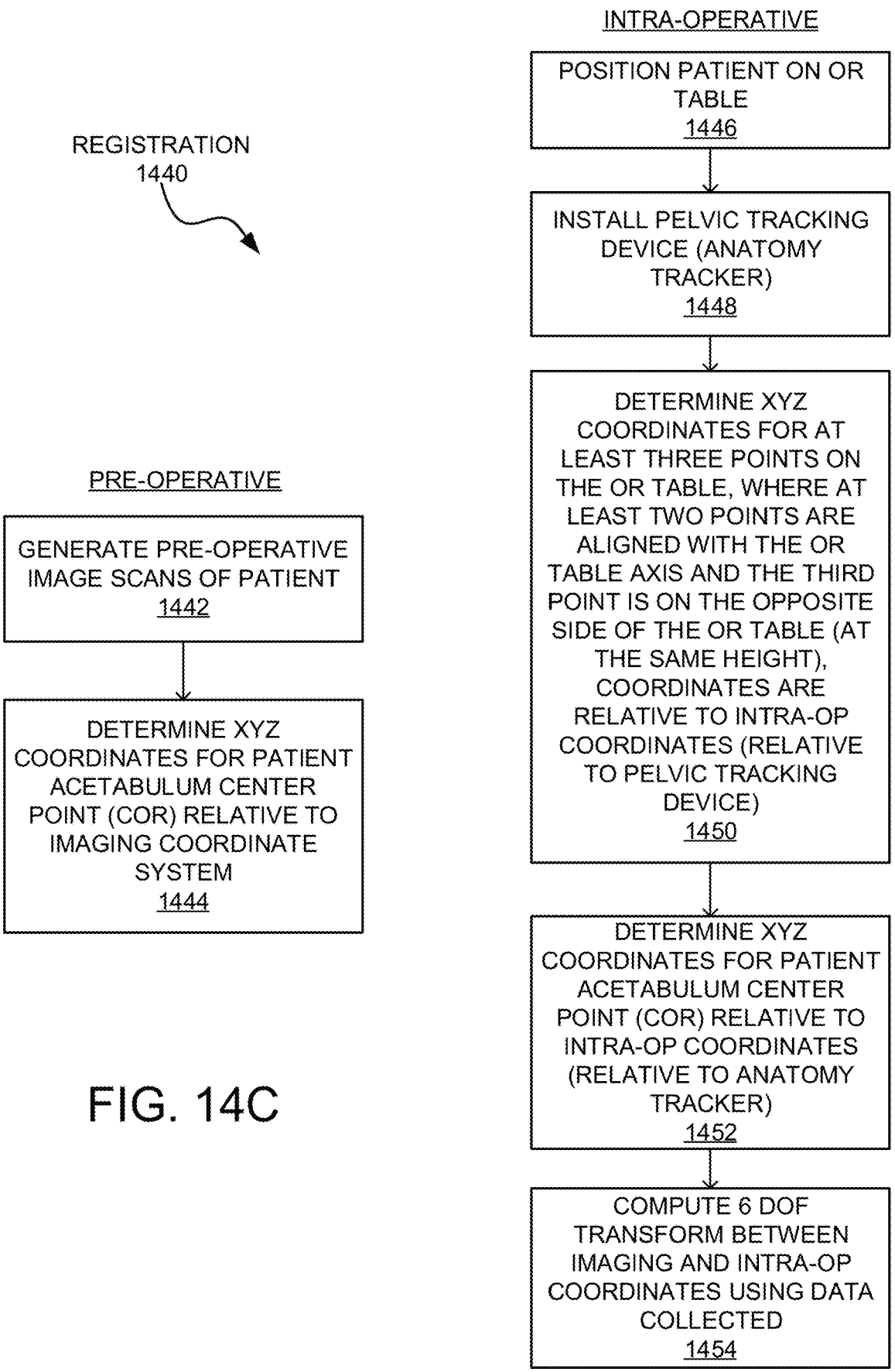
FIG. 14C illustrates pre-operative and intra-operative steps of a registration method.
Figure 15E:
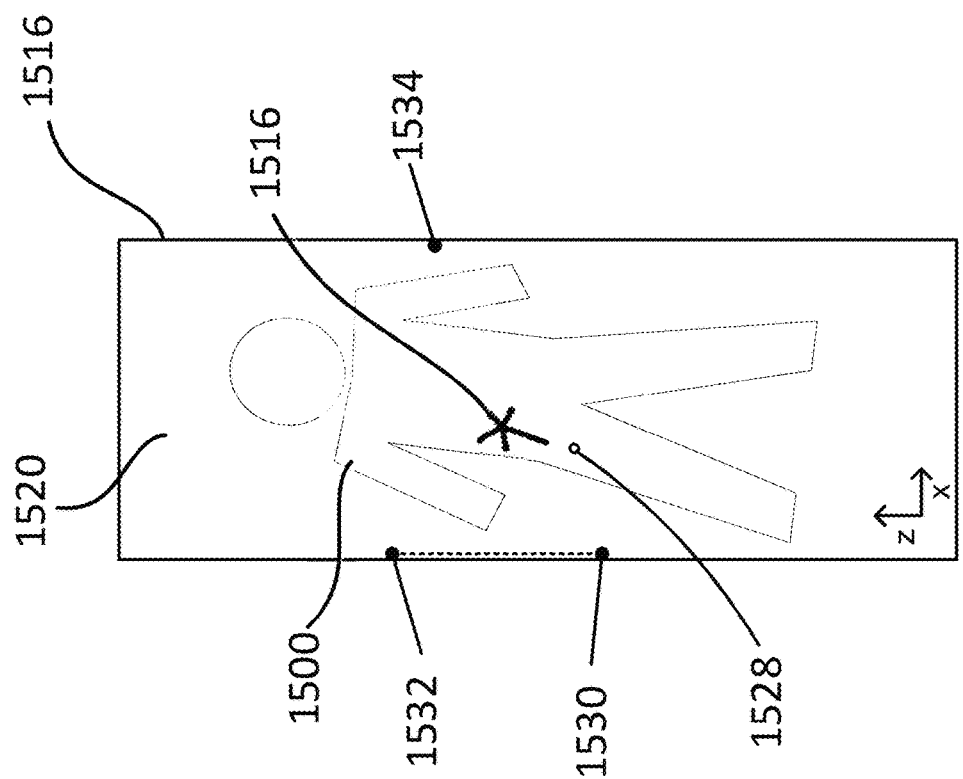
FIG. 15E depicts an overhead view of a patient on an operating room table.
Figure 15D:
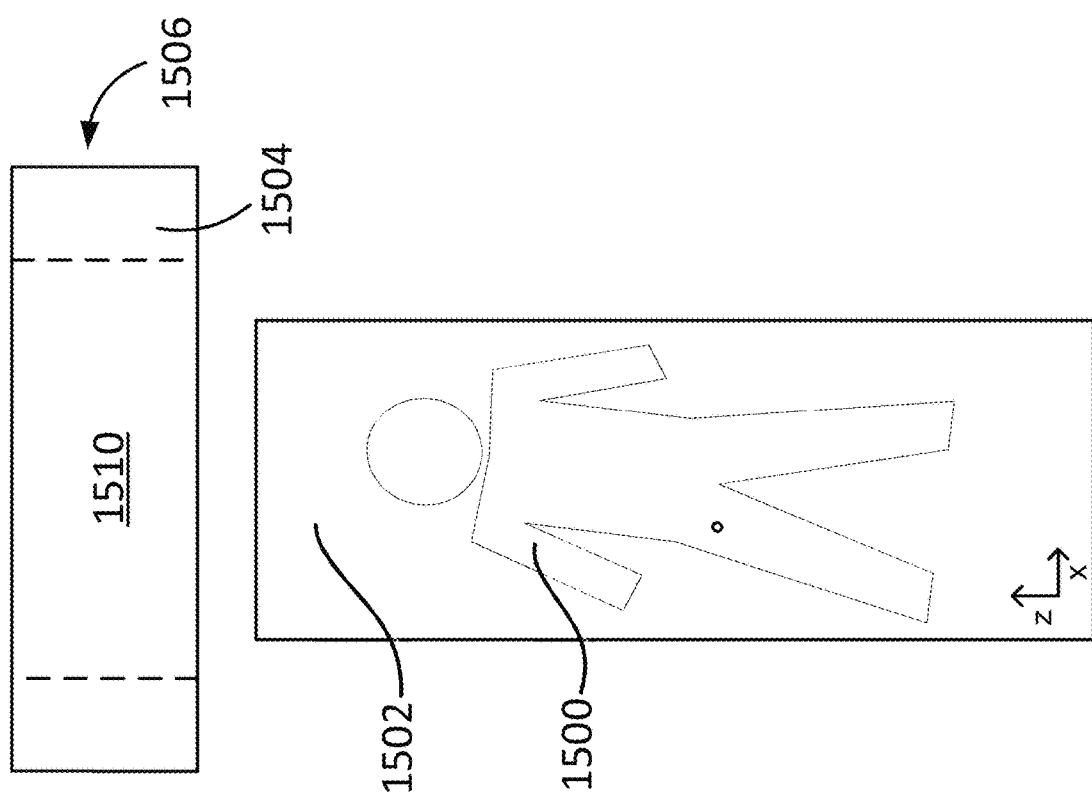
FIG. 15D depicts an overhead view of a patient on an imaging table.

Additionally, or alternatively, the surgical registration method may be as illustrated in FIGS. 14C and 15D-15E. FIG. 14C illustrates a flowchart showing exemplary steps in a surgical registration method 1440. FIG. 15D illustrates an overhead view of a patient 1500 on an imaging table 1502 about to undergo an imaging event (e.g., CT, MRI). FIG. 15E illustrates the patient 1500 on an operating room table 1520 about to undergo a surgical procedure. The registration method 1440 takes information about the pre-operative position and orientation of the patient 1500 on the imaging table 1502 and assumes certain information about the position and orientation of the patient will be consistent when the patient lies on the operating room table 1520.

Referring to FIG. 14C, at step 1442, image scans of the patient 1500 are generated. The image scans may be CT, X-ray, or MRI, among other imaging modalities. At step 1444, the acetabulum center of rotation (COR) may be determined relative to the imaging coordinate system. The imagine device may include its own coordinate system (x, y, z) based on the translational movements of the imaging table 1502, for example (as seen in FIG. 15D, the table 1502 lies in the xz plane). That is, the table 1502 may translate in the z-direction in order to move the patient and table within the opening 1510 of the imaging arm 1504 of the imaging device 1506. The table 1502 may additionally translate in the x-direction and y-direction to center the patient and table within the opening 1510 of the arm 1504.

The COR of the acetabulum may be identified by a user selecting the COR within the image scans, for example, by selecting the COR in multiple coordinate views (e.g., coronal, sagittal, axial). Additionally, or alternatively, the method 1440 may include generating a three-dimensional bone model of the patient bone either from the image scans, a statistical bone model, or generic bone model, among others. And, any method known in the art or described herein may be used to identify the COR from the bone model within the imaging coordinate system. It is noted, the COR may be a three-dimensional location (x, y, z) of one or more points relative to an origin (0, 0, 0) of the imaging coordinate system.

Moving to the intra-operative portion of the method 1440, at step 1446 of FIG. 14C, and as also seen in FIG. 15E, the patient 1500 is positioned on the OR table 1520. At step 1448, a pelvic tracking device (anatomy tracker) 1516 is attached to the patient's diseased pelvis.

At step 1450, the XYZ coordinates of the operating room table 1520 are identified. More particularly, at least three points 1530, 1532, 1534 are identified on the table 1520, where two points 1530, 1532 are located on the same side of the table (e.g., edge of the table so as to be at the same point on the x-axis), and one point 1534 is located on the opposite side of the table 1520. The two points 1530, 1532 may be oriented or aligned with the OR table axis or Z-axis, as shown in FIG. 15E. All points 1530, 1532, and 1534 may be positioned at the same position along the y-axis. Stated differently, the three points 1530, 1532, 1534 may be positioned at the same height relative to a plane defined by the top of the OR table 1520. The three points 1530, 1532, 1534 may be captured or logged with a tracked pointer of the system, and may be identified relative to the position of the pelvic tracking device 1516 in the intra-operative coordinate system. As an alternative to collecting points 1530, 1532, 1534 on the OR table 1520, the table axes (x, y, z) may be determined by translating the table in order along the corresponding axes to ascertain the applicable vectors. In certain instances, it may be advantageous to determine the points 1530, 1532 prior to extensive leg manipulation to ensure the patient has not moved (e.g., before femoral dislocation).

At step 1452, the XYZ coordinates of the acetabulum center point (COR) may be determined in the intra-operative coordinate system (relative to the anatomical tracker 1516, or another point. The COR may be determined based on any method described herein or known in the art. In certain instances, the COR may be determined from a range of motion analysis. In certain instances, the COR may be determined based on a point-picking approach after the femoral head is dislocated from the acetabulum.

At this point, at least the following points are identified within the intra-operative coordinate system: points 1530, 1532, and 1534 located on the OR table 1520, and the COR of the patient's acetabulum. And at least the following points are identified within the pre-operative imaging coordinate system: COR of the acetabulum, as well as the coordinate axes (x, y, z), which correlate to the translational movement of the imaging table 1502.

Next, at step 1454 of FIG. 14C, a six degree-of-freedom (DOF) transform is computed between the imaging coordinate points and the intra-operative coordinate points so as to register the pre-operative images to the intra-operative position of the patient 1500. In this way, a robotic arm or handheld surgical device of an autonomous or haptic-driven device may be able to identify the position and orientation of patient for performance of a surgical procedure.

Figure 14D:
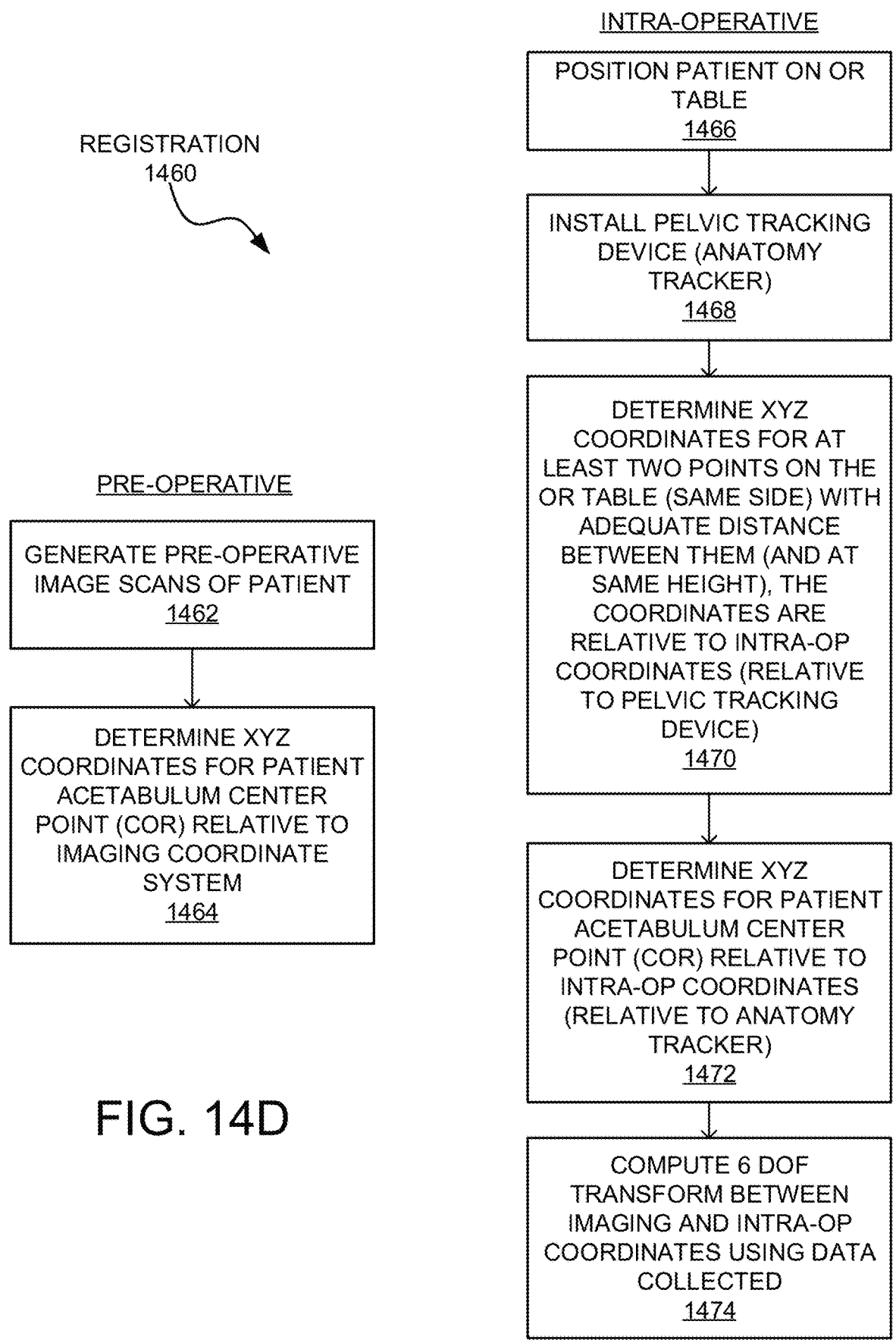
FIG. 14D illustrates pre-operative and intra-operative steps of a registration method.
Figure 15G:
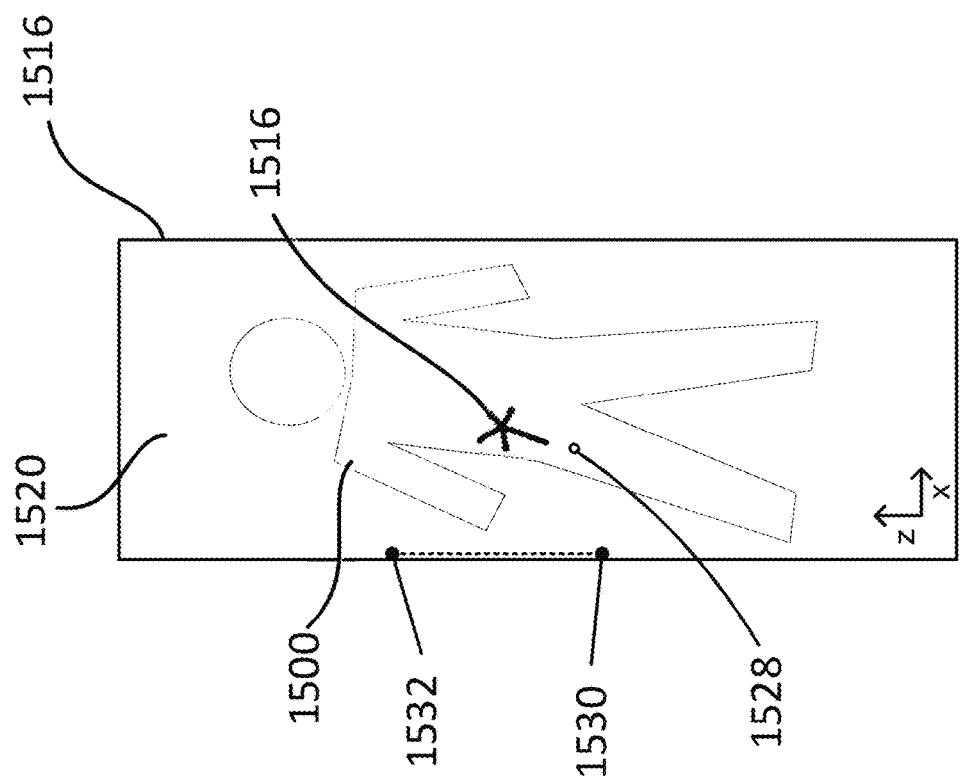
FIG. 15G depicts an overhead view of a patient on an operating room table.
Figure 15F:
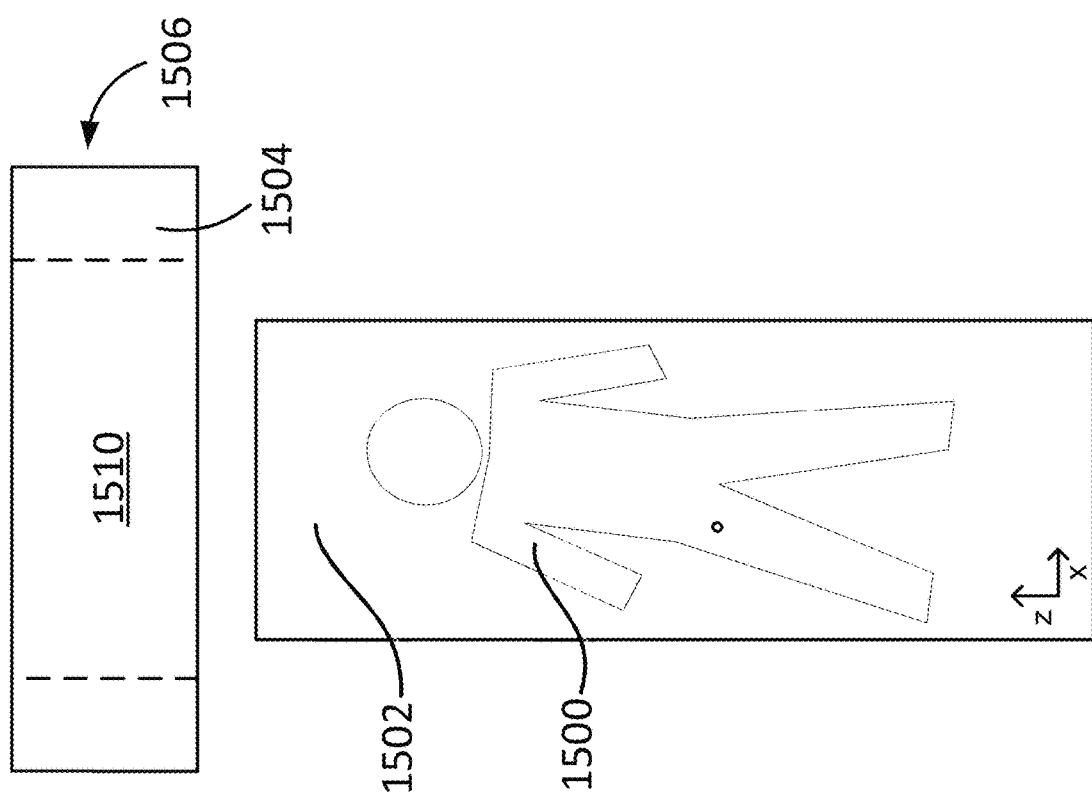
FIG. 15F depicts an overhead view of a patient on an imaging table.

Additionally, or alternatively, the surgical registration method may be as illustrated in FIGS. 14D and 15F-15G. FIG. 14D illustrates a flowchart showing exemplary steps in a surgical registration method 1460. FIG. 15F illustrates an overhead view of a patient 1500 on an imaging table 1502 about to undergo an imaging event (e.g., CT, MRI). FIG. 15G illustrates the patient 1500 on an operating room table 1520 about to undergo a surgical procedure. The registration method 1460 takes information about the pre-operative position and orientation of the patient 1500 on the imaging table 1502 and assumes certain information about the position and orientation of the patient will be consistent when the patient lies on the operating room table 1520.

Referring to FIG. 14D, at step 1462, image scans of the patient 1500 are generated. The image scans may be CT, X-ray, or MRI, among other imaging modalities. At step 1464, the acetabulum center of rotation (COR) may be determined relative to the imaging coordinate system. The imagine device may include its own coordinate system (x, y, z) based on the translational movements of the imaging table 1502, for example (as seen in FIG. 15F, the table 1502 lies in the xz plane). That is, the table 1502 may translate in the z-direction in order to move the patient and table within the opening 1510 of the imaging arm 1504 of the imaging device 1506. The table 1502 may additionally translate in the x-direction and y-direction to center the patient and table within the opening 1510 of the arm 1504.

The COR of the acetabulum may be identified by a user selecting the COR within the image scans, for example, by selecting the COR in multiple coordinate views (e.g., coronal, sagittal, axial). Additionally, or alternatively, the method 1460 may include generating a three-dimensional bone model of the patient bone either from the image scans, a statistical bone model, or generic bone model, among others. And, any method known in the art or described herein may be used to identify the COR from the bone model within the imaging coordinate system. It is noted, the COR may be a three-dimensional location (x, y, z) of one or more points relative to an origin (0, 0, 0) of the imaging coordinate system.

Moving to the intra-operative portion of the method 1460, at step 1466 of FIG. 14D, and as also seen in FIG. 15G, the patient 1500 is positioned on the OR table 1520. At step 1468, a pelvic tracking device (anatomy tracker) 1516 is attached to the patient's diseased pelvis.

At step 1470, the XYZ coordinates of the operating room table 1520 are identified. More particularly, at least three points 1530, 1532 are identified on the table 1520, where the two points 1530, 1532 are located on the same side of the table 1520 (e.g., edge of the table so as to be at the same point on the x-axis). The two points 1530, 1532 may be oriented or aligned with the OR table axis or Z-axis, as shown in FIG. 15G. The points 1530, 1532 may be positioned at the same position along the y-axis. Stated differently, the two points 1530, 1532 may be positioned at the same height relative to a plane defined by the top of the OR table 1520. The two points 1530, 1532 may be captured or logged with a tracked pointer of the system, and may be identified relative to the position of the pelvic tracking device 1516 in the intra-operative coordinate system. As an alternative to collecting points 1530, 1532 on the OR table 1520, the table axes (x, y, z) may be determined by translating the table in order along the corresponding axes to ascertain the applicable vectors. In certain instances, it may be advantageous to determine the points 1530, 1532 prior to extensive leg manipulation to ensure the patient has not moved (e.g., before femoral dislocation).

At step 1472, the XYZ coordinates of the acetabulum center point (COR) may be determined in the intra-operative coordinate system (relative to the anatomical tracker 1516, or another point. The COR may be determined based on any method described herein or known in the art. In certain instances, the COR may be determined from a range of motion analysis. In certain instances, the COR may be determined based on a point-picking approach after the femoral head is dislocated from the acetabulum.

At this point, at least the following points are identified within the intra-operative coordinate system: points 1530, 1532 located on the OR table 1520, and the COR of the patient's acetabulum. And at least the following points are identified within the pre-operative imaging coordinate system: COR of the acetabulum, as well as the coordinate axes (x, y, z), which correlate to the translational movement of the imaging table 1502.

Next, at step 1474 of FIG. 14D, a six degree-of-freedom (DOF) transform is computed between the imaging coordinate points and the intra-operative coordinate points so as to register the pre-operative images to the intra-operative position of the patient 1500. In this way, a robotic arm or handheld surgical device of an autonomous or haptic-driven device may be able to identify the position and orientation of patient for performance of a surgical procedure.

D. Registering of Robotic Arm

Referring back to FIG. 5, after registering the pelvis at step S6, the robotic arm 30 may be registered at step S7. In this step, the robotic arm 30 is registered to correlate the pose of the robotic arm 30 (physical space) with the navigation system 7 (image space). The robotic arm 30 can be registered, for example, as described in U.S. patent application Ser. No. 11/357,197 (Pub. No. US 2006/0142657), filed Feb. 21, 2006, and hereby incorporated by reference herein in its entirety.

E. Preparation of the Acetabulum and Performance of the Surgical Procedure

In operation, the surgeon can use the robotic arm 30 of FIG. 3B to facilitate a joint replacement procedure, such as reaming bone and implanting an acetabular cup for a total hip replacement or hip resurfacing procedure. As explained above, the robotic arm 30 includes a surgical tool configured to be coupled to a cutting element (for reaming) and to engage a prosthetic component (for impacting). For example, as seen in FIG. 3B, for reaming, the end effector 40 can couple to the operating member 100, which couples to a cutting element. Similarly, for impacting, the end effector 40 can couple to another operating member, which engages the prosthetic component. The robotic arm 30 can be used to ensure proper positioning during reaming and impacting.

In step S8 of FIG. 5, the surgeon resurfaces the acetabulum 22 using a reamer, such as the operating member 100, coupled to the robotic arm 30 of FIG. 3B. As described above in connection with the operating member 100, the surgeon couples the appropriate operating member (e.g., a straight or offset reamer) to the end effector 40, connects the cutting element to the received operating member, and manually manipulates the robotic arm 30 to ream the acetabulum 22. During reaming, the robotic arm 30 provides haptic (force feedback) guidance to the surgeon. The haptic guidance constrains the surgeon's ability to manually move the surgical tool to ensure that the actual bone cuts correspond in shape and location to planned bone cuts (i.e., cuts consistent with the surgical plan). In certain instances, an autonomous or hand held system may work within a defined virtual boundary without haptic feedback or guidance.

In step S9 of FIG. 5, the surgeon verifies that the registration (i.e., the geometric relationship) between the acetabular tracking array and the pelvis 12 is still valid by contacting the pelvis checkpoint with a tracked probe as described, for example, in U.S. patent application Ser. No. 11/750,807 (Pub. No. US 2008/0004633), filed May 18, 2007, and hereby incorporated by reference herein in its entirety. If registration has degraded (e.g., because the acetabular tracking array was bumped during reaming), the pelvis 12 is re-registered. Registration verification can be performed any time the surgeon wants to check the integrity of the acetabular registration.

In step S10 of FIG. 5, the prosthetic component 316 is implanted on the reamed acetabulum 22 using an impactor tool. In a manner identical to that described above in connection with step S8 (reaming), during the impaction step S10, the display device 9 can show the planned pose 500, the activation region 510, the representations 512, 514 of the anatomy, and a representation of the surgical tool, as seen in FIG. 4. Also as described above in connection with step S8, if the surgeon moves the end effector 40 to override the haptic feedback, the controller can initiate automatic control of the surgical tool to substantially align at least one aspect of the actual pose with the corresponding desired aspect of the target pose.

In step S11 of FIG. 5, the surgeon installs the femoral component on the femur 14, and in step S12, the surgeon determines leg length and femoral offset. At any time during the surgical procedure, the display device 9 can show data related to progress and/or outcome. For example, after reaming in step S8 and/or impacting in step S10, data relating to the actual position of the reamed acetabulum 22 (or the implanted acetabular cup) can include, for example, numerical data representing error between the actual and planned locations in the three orthogonal planes of the patient's anatomy (i.e., medial/lateral, superior/inferior, and anterior/posterior).

V. Tools and Methods for Bone Registration of Femur, Pelvis, and Vertebrae, Among Other Bones Point-picking based bone registration is one method of registration in navigated and robotic assisted orthopedic surgeries. During a surgical procedure, an incision is made at the surgical site (e.g., hip, knee). A localization pointer or tracked probe is utilized to pick a digitized point-cloud (a set of data points in a coordinate system representing a surface contour) on boney areas of the patient's body that are accessible through the incision. By using point-pair and iterative closest point (ICP) algorithms, the patient point-cloud data in "tracker space" (coordinate system with position data corresponding to trackers on the patient body and the point-cloud of patient collected points) is transformed to the three-dimensional bone model of the patient's bone formed from segmented medical images, or otherwise. An accurate registration transform is determined as the minimum root-mean-square of the point-cloud fitting.

In the context of point-picking based registration (femoral, pelvic, or otherwise), intra-operatively picking points on the bone surface with a probe generally requires the surgeon to have access to the bones though the initial incision at the surgical site. Due to small incision areas, especially in minimally invasive surgeries, it can be difficult to ensure six degrees of freedom accuracy in registration when relying on point-cloud data collected only within the surgical incision. To increase accuracy of such registrations, points can be added to the point-cloud that are far from the surgical site. For example, in a total hip arthroplasty procedure, a surgeon may capture points on the patient's acetabulum, and additionally capture points on the iliac crest surface of the patient's ilium to increase registration accuracy. Still in the context of a total hip arthroplasty, a surgeon may pick points on the proximal femur (e.g., femoral head), and may additionally capture points on a distal or mid-distal femur surface to increase the registration accuracy. The iliac crest and distal femur are, however, not within the initial surgical incision.

In order to pick such distant points on the iliac crest and distal femur (i.e., that are not within the initial surgical incision), the surgeon may need to make an additional incision (e.g., stab incision) remote from the initial incision for the sole purpose of contacting a tracked probe or localization pointer against the patient's bone(s). Making additional incisions into the patient's body may not be ideal as there is an increased chance of infection, pain, scarring, and time associated with such a method.

Figure 16C:
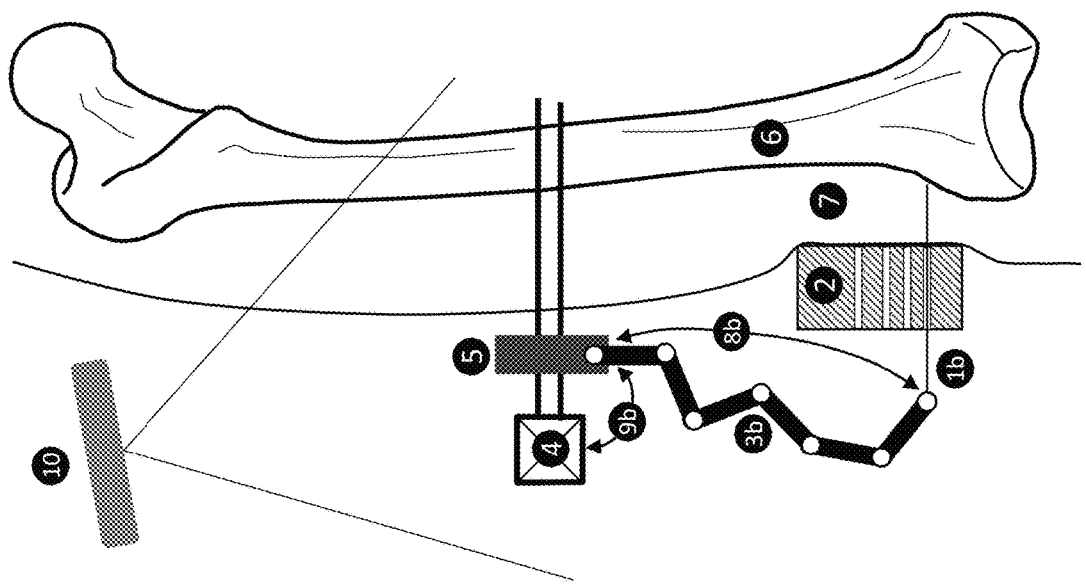
FIG. 16C depicts an anterior view of a femur with a second embodiment of a needle-based registration system.
Figure 16B:
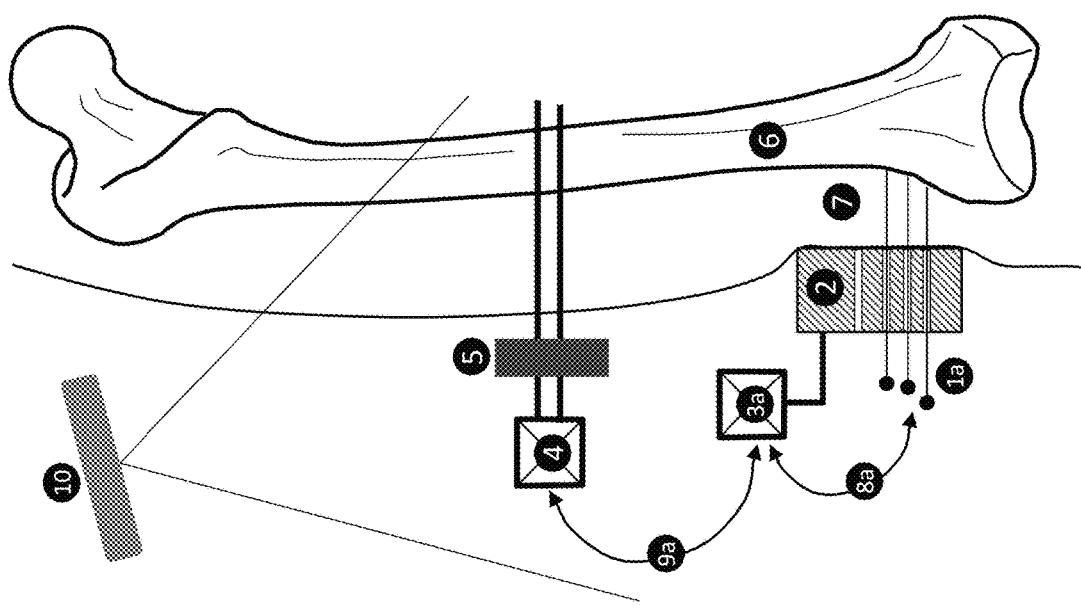
FIG. 16B depicts an anterior view of a femur with a first embodiment of a needle-based registration system.
Figure 16A:
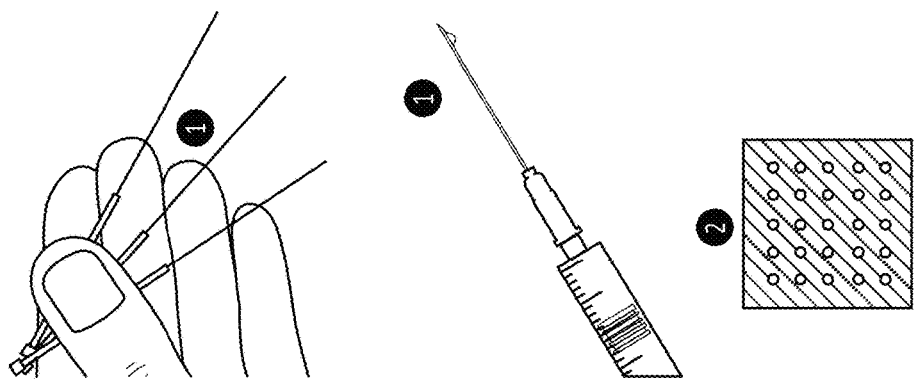
FIG. 16A depicts needles of various lengths and diameters, and a needle template.

Described herein in reference to FIGS. 16A-16C are registration tools and methods for use in zones of the patient's body that are remote from the surgical site (i.e., outside the surgical incision) and that do not involve additional incisions in the patient's skin. As seen in FIG. 16A, needles 1 of varying lengths and diameters, such as an acupuncture needle or a syringe needle, may be used to digitize points on hard bone surface without incision though the patient's skin. The needle 1 diameter may be small enough to easily penetrate patient skin, the soft tissue, and the cartilage of the patient with no side effect on patient satisfaction. Using needles 1, bone registration points can be picked in anatomic regions which are normally not accessible through in-wound point picking method, especially in MIS.

As seen in FIG. 16B, which is an anterior view of a femur 6 in accordance with the present disclosure, one or more needles 1a may be inserted into soft tissue 7 through one of a plurality of holes of a needle fixture or template 2. The needle fixture 2 may guide the needles 1a through the skin, and the needles 1a may stop at the hard bone surface of the femur 6. A passive or active localization marker may be attached to the needles 1a so as to navigate the position of the needle-top via one or more cameras 10 (e.g., optical camera). A needle tracker 3a may be coupled to the needle fixture 2. However, a needle tracker 3a may not be needed if the needle tips are tracked. The fixture 2 may have multiple functions, including: (1) compressing the soft tissue; (2) guiding insertion of the needles 1a; and (3) measuring the position of the needle tip relative to the needle tracker 3a via a transform 8a.

Still referring to FIG. 16B, a bone tracker 4 may be rigidly attached to a hard bone surface of the femur 6 by a clamp and bone pin 5. A needle tip position in bone tracker 4 space may be determined through a transform 9a. The needle fixture 2, together with needle tracker 3a, can be freely moved to different anatomical locations of the bone to digitize multiple points on bone surface 6, and add those points to the point-cloud. The camera 10 may track the position of the bone tracker 4 and the needle tracker 3a.

As seen in FIG. 16C, which is an anterior view of a femur 6 in accordance with the present disclosure, a proximal end of a needle 1b is attached to a mechanical tracker 3b so as to navigate the position of needle tip (distal end of needle) in mechanical tracker 3b space through transform 8b. The mechanical tracker 3b may be attached to the bone clamp 5 or another reference position. The mechanical tracker 3b may be registered to an optical tracker 4 by transform 9b. Mechanical tracker 3b may indicate the position of each joint—such as via encoders, or fiber optic trackers. A camera (e.g., optical camera) may track the movement of the optical tracker 4. And, a needle tip position in bone tracker 4 space is further determined through transform 9b. The needle fixture 2 and tip-center point (TCP) of mechanical tracker 3b can be freely moved to different anatomical locations of the bone to digitize multiple points on the bone surfaces 6, and add those points to the point-cloud.

Figure 17C:
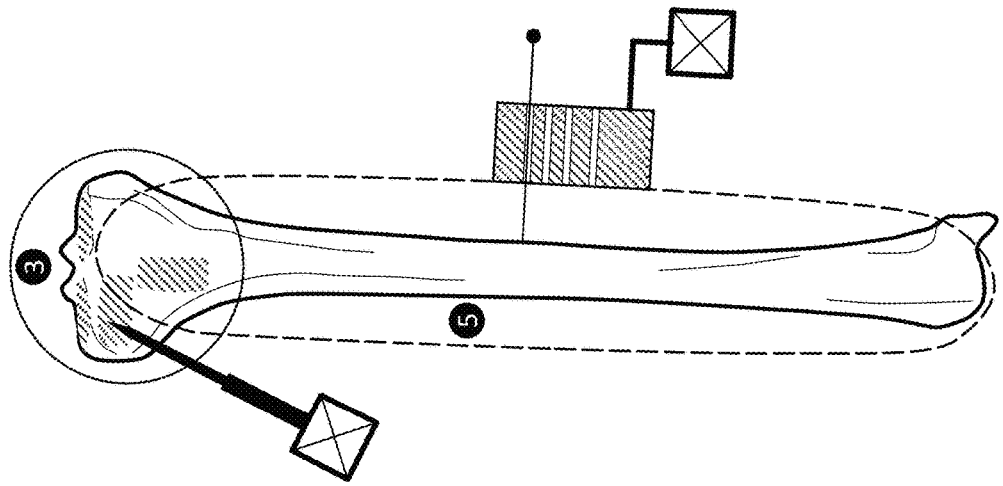
FIG. 17C depicts the needle-based registration system used on a mid-distal portion of a tibia.
Figure 17B:
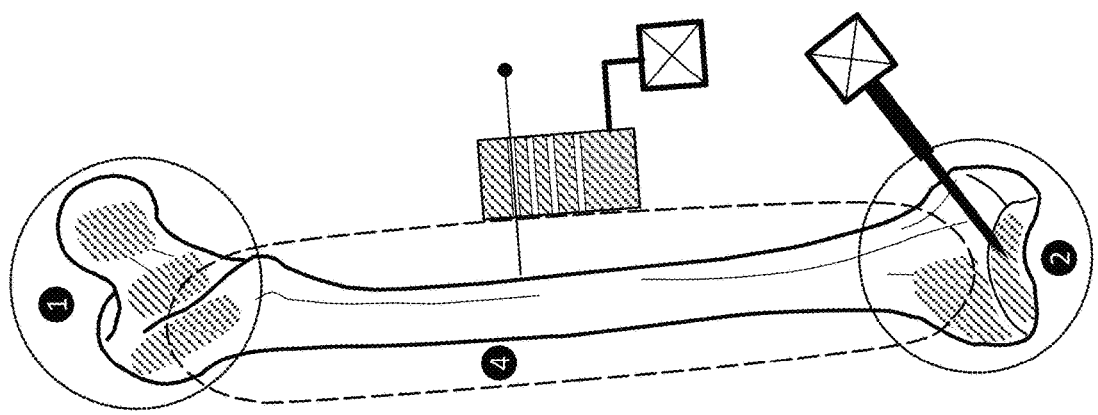
FIGS. 17A and 17B depict a needle-based registration system used on a mid-distal portion of a femur.
Figure 17A:
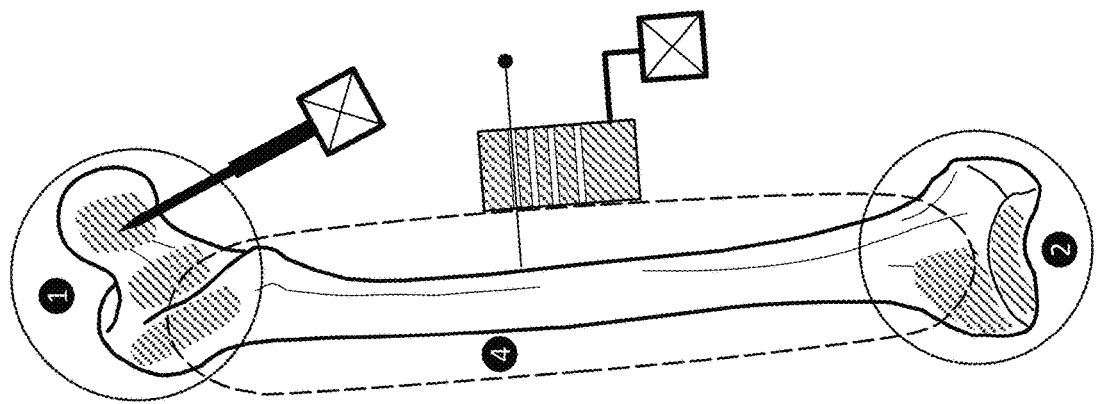

In certain instances, a registration system 1700 may be utilized as seen in FIGS. 17A-17C. FIG. 17A shows an anterior view of a femur 4 being registered with the registration system 1700 in a total hip arthroplasty context, FIG. 17B shows an anterior view of the femur 4 being registered with the registration system 1700 in a total knee arthroplasty context, and FIG. 17C shows an anterior view of a tibia 5 being registered with the registration system 1700 in a total knee arthroplasty context.

As seen in FIG. 17A, the proximal end of the femur 4 may be subject to point-picking via a tracked pointer through the incision in the patient at the surgical site (e.g., hip region). In the case of a total hip arthroplasty, the femoral head may be exposed and easily accessible for point-picking via the tracked pointer for developing a point-cloud of data to be used in the registration process. To increase accuracy of the registration transform, the registration system 1700 including a needle template 2 including a plurality of through-holes, a needle tracker 3, and a tracking needle 1a are used on the shaft of the femur 4 approximately midway between the proximal femoral head and the distal femoral condyles. The needle template 2 may be pressed against the patient's skin, and the needle template 2 may be used to guide one or more needles 1a into the patient's skin until it contacts the bone surface of the femur. The optical camera (not shown) may sense the position of the needle template 2, and the corresponding position of the needle within one of the through-holes of the template 2.

Thus, when the registration transform is ran, the system may use point-cloud data associated with surface points on the femoral head and on a mid-distal femoral bone surface to increase the accuracy of the process.

As seen in FIG. 17B, the distal end of the femur 4 may be subject to point-picking via a tracked pointer through the incision in the patient at the surgical site (e.g., knee region). In the case of a total knee arthroplasty, the femoral condyles may be exposed and easily accessible for point-picking via the tracked pointer for developing a point-cloud of data to be used in the registration process. To increase accuracy of the registration transform, the registration system 1700 including a needle template 2 including a plurality of through-holes, a needle tracker 3, and a tracking needle 1a are used on the shaft of the femur 4 approximately midway between the proximal femoral head and the distal femoral condyles. The needle template 2 may be pressed against the patient's skin, and the needle template 2 may be used to guide the needle 1a into the patient's skin until it contacts the bone surface of the femur. The optical camera (not shown) may sense the position of the needle template 2, and the corresponding position of the needle within one of the through-holes of the template 2.

Thus, when the registration transform is ran, the system may use point-cloud data associated with surface points on the femoral condyles and on a mid-distal femoral bone surface to increase the accuracy of the process.

As seen in FIG. 17C, the proximal end of the tibia 5 may be subject to point-picking via a tracked pointer through the incision in the patient at the surgical site (e.g., knee region). In the case of a total knee arthroplasty, the proximal tibia (e.g., tibial plateau) may be exposed and easily accessible for point-picking via the tracked pointer for developing a point-cloud of data to be used in the registration process. To increase accuracy of the registration transform, the registration system 1700 including a needle template 2 including a plurality of through-holes, a needle tracker 3, and a tracking needle 1a are used on the shaft of the tibia 5 approximately midway between the proximal tibia and the distal tibia. The needle template 2 may be pressed against the patient's skin, and the needle template 2 may be used to guide the needle 1a into the patient's skin until it contacts the bone surface of the tibia. The optical camera (not shown) may sense the position of the needle template 2, and the corresponding position of the needle within one of the through-holes of the template 2.

Thus, when the registration transform is ran, the system may use point-cloud data associated with surface points on the proximal tibia and on a mid-distal tibial bone surface to increase the accuracy of the process.

Figure 18:
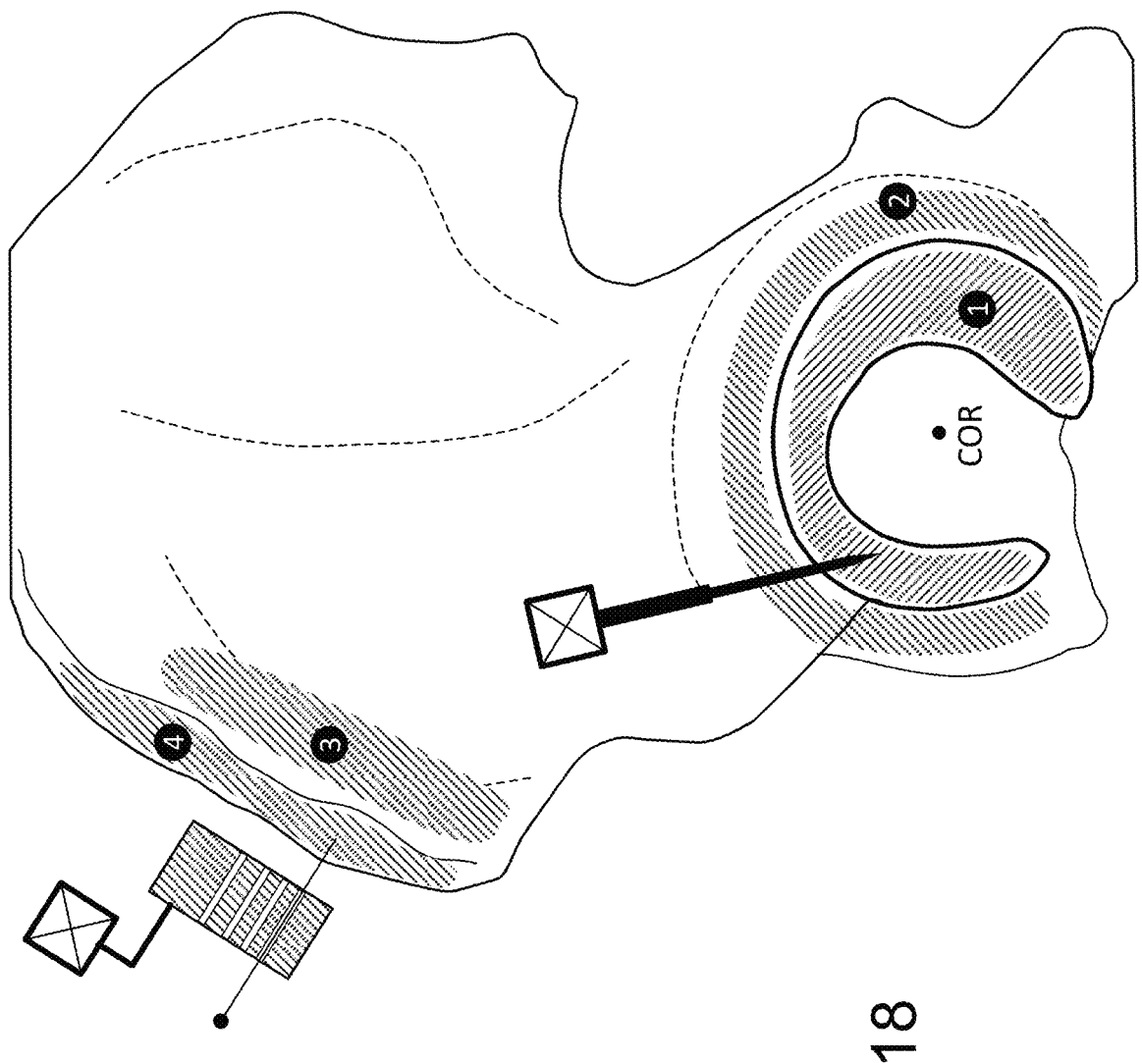
FIG. 18 depicts a side view of an ilium with the needle-based registration system utilized on the iliac crest.

The registration system 1700 described with reference to FIGS. 17A-17C may be employed on the ilium, as seen in FIG. 18. More particularly, the acetabular rim 2 and acetabular articular surface 1 may be accessible in a hip arthroplasty procedure, but, the iliac crest 4, and an area just inferior to the lip of the iliac crest (i.e., the portion of the dorsus ossis ilium between the iliac crest 4 and the anterior gluteal line) is generally not within the surgical incision for conventional hip arthroplasty procedures. As seen in FIG. 18, the articular surface 1 and the rim 2 of the acetabular may be point-picked via a tracked pointer through the incision in the hip region. From the articular surface 1 and the rim 2, the system may determine a center of rotation COR by, for example, the method described in PCT/US2017/049466, filed Aug. 30, 2017, which is hereby incorporated by reference in its entirety into the present application. To increase the accuracy of the registration transform, the registration system 1700 including a needle template 2 including a plurality of through-holes, a needle tracker 3, and a tracking needle 1*a* are used on the iliac crest proximate the anterior superior iliac spine. The needle template 2 may be pressed against the patient's skin, and the needle template 2 may be used to guide the needle 1*a* into the patient's skin until it contacts the bone surface of the ilium. The optical camera (not shown) may sense the position of the needle template 2, and the corresponding position of the needle within one of the through-holes of the template 2.

Thus, when the registration transform is ran, the system may use point-cloud data associated with surface points on the acetabular region of the ilium and on the iliac crest surface to increase the accuracy of the process.

Figure 19B:
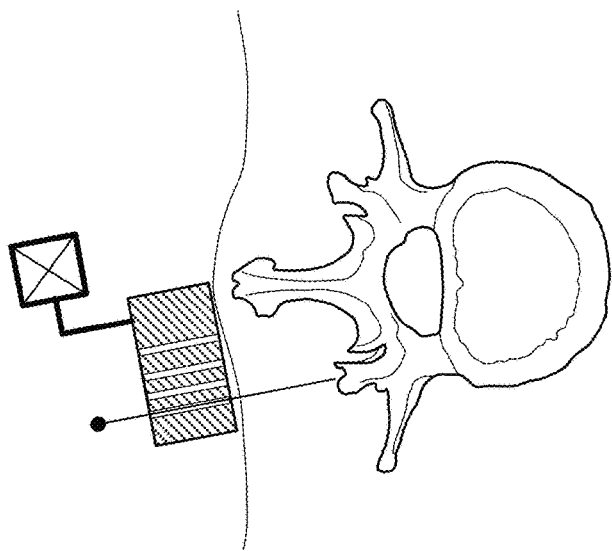
FIGS. 19A and 19B depict, respectively, a side view and a cross-sectional axial view of the needle-based registration system utilized on the spine.
Figure 19A:
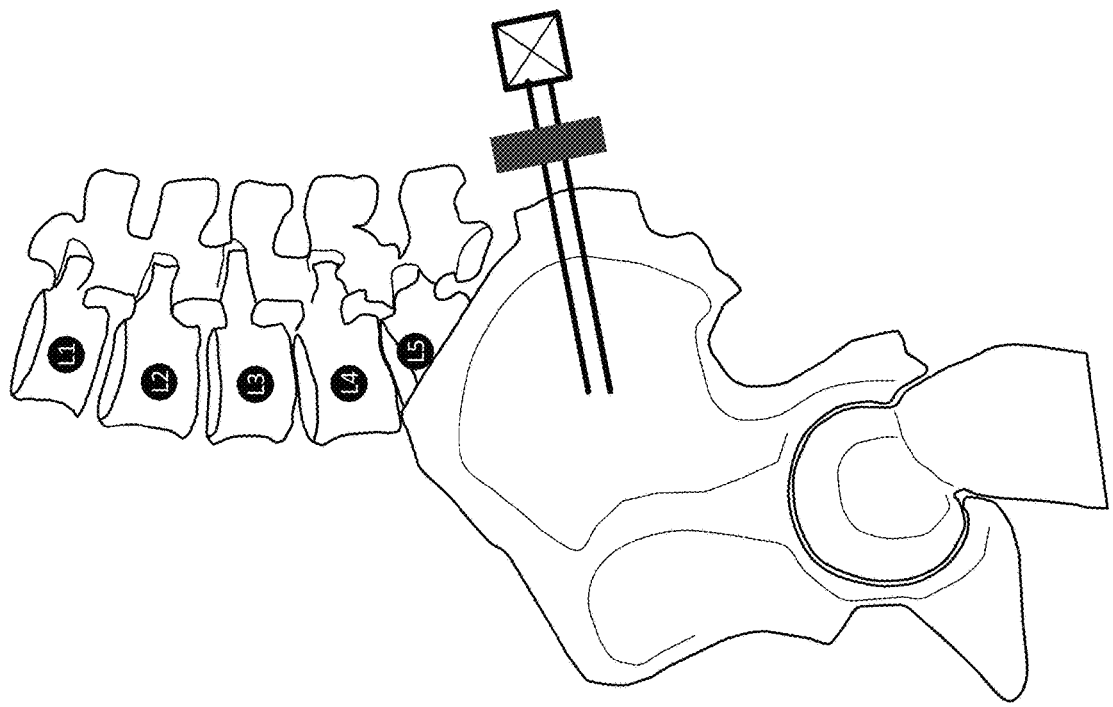

The registration system 1700 may additionally or alternatively be used on other parts of the patient's body that may be segmented, such as the spine (L1, L2, L3, L4, L5). As seen in FIG. 19A, which is a side view of an ilium and a spinal column, a tracking array may be positioned on the patient's ilium. Additionally, the registration system 1700 including a needle template 2 including a plurality of through-holes, a needle tracker 3, and a tracking needle 1*a* may be used on the boney portions of the posterior aspect of the vertebrae of the spine. The needle template 2 may be pressed against the patient's skin, and the needle template 2 may be used to guide the needle 1*a* into the patient's skin until it contacts the bone surface of the vertebrae. The optical camera (not shown) may sense the position of the needle template 2, and the corresponding position of the needle within one of the through-holes of the template 2.

Thus, when the registration transform is run, the system may use point-cloud data associated with the vertebrae, along with another registration area, to increase the accuracy of the process. The method described herein may be utilized on any bone, and is not limited to bones of the legs and vertebrae. The needle-based registration method may be used on bones of the arms, hands, feet, upper body, and head, without limitation.

Reference is made to FIGS. 20A-20D, which depict, respectively, an axial cross-section image of a vertebra 2000 and a bone anchor 2002 positioned therein, an axial cross-section image of a vertebra 2000 with a rotating burr 2004 positioned partially within the vertebra 2000, another axial cross-section image of a vertebra 2000 with a rotating burr 2004 positioned partially within the vertebra 2000, and an axial cross-section image of a burr 2004 extending through a vertebra 2000 to a far inner wall of the cortical bone 2006.

Accuracy in spinal registration can be challenging. Conventionally, a tracker device is placed in the pelvis of the patient so the vertebrae (which is the subject of a surgical procedure) could be several non-rigid joints away from the tracker. Thus, when the patient is positioned in a prone position (i.e., on the stomach), among other positions, there may be a significant soft tissue pushing against the vertebrae that could alter the position of the vertebrae. Additionally, working on adjacent vertebral segments may move the spine slightly.

Figure 20A:
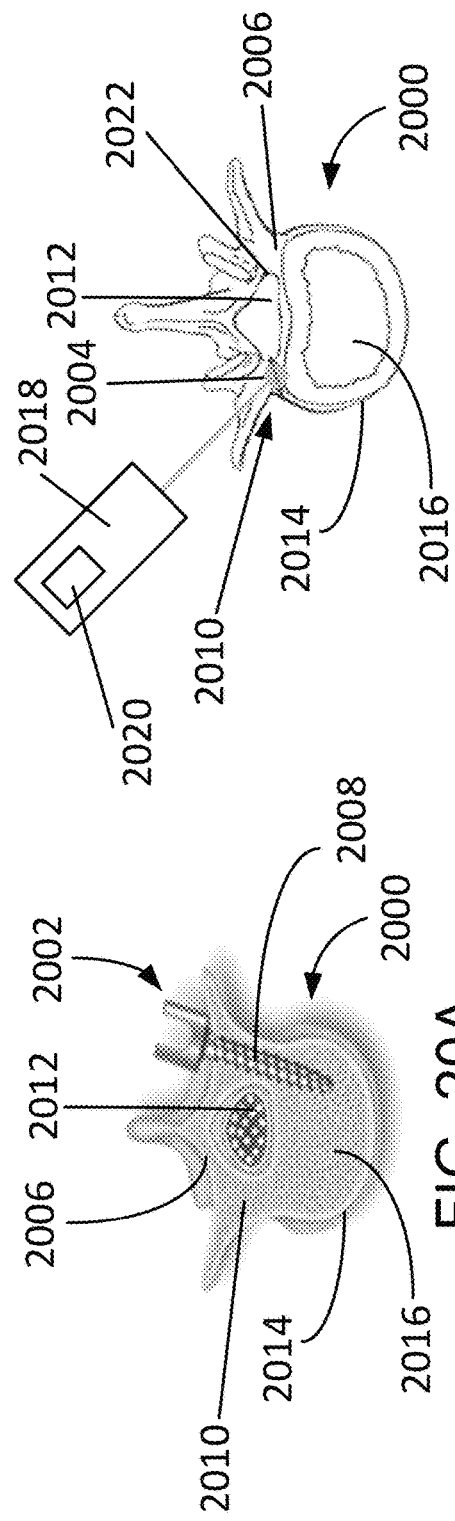
FIG. 20A (prior art) is an axial cross-section image of a vertebra with a bone anchor positioned within the pedicle.

A goal of the tools, systems, and methods described subsequently is to confirm and improve registration by identifying contact with the internal cortical bone of the vertebra 2000 after initial penetration of the outer surface of the vertebra 2000. To that end, FIG. 20A shows an axial cross-section image of a vertebra 2000 with a bone anchor 2002 positioned therein. As seen in the figure, a shank 2008 of the bone anchor 2002 extends through a pedicle 2010 of the vertebra 2000 while avoiding contact with the spinal cord 2012. The vertebra 2000 includes cortical bone 2006 (compact bone) on outer portions or outer shell including a cortical rim 2014 surrounding the vertebral body, and cancellous bone 2016 (spongy or trabecular bone) interior of the cortical bone 2006. The cortical bone 2006 is harder and denser than the cancellous bone 2016, which is porous, weaker, and easier to fracture than cortical bone 2006. Cancellous bone 2016 makes up the shafts of long bones (e.g., femur, tibia). Cortical bone 2006 surrounds and protects the spinal cord 2012.

When inserting a bone anchor 2002 into a vertebra 2000, as seen in FIG. 20A, the surgeon attempts to position the anchor 2002 as shown in the figure where the shank 2008 remains within the vertebra 2000 (i.e., does not exit either side of the cortical bone 2006). That is, the shank 2008 remains within the cancellous bone 2016 once it initially penetrates through the cortical bone 2006. Conventional ways to ensure placement of the shank 2008 within the interior of the vertebra 2000 is for a surgeon to drill through the outer cortical layer of the vertebra 2000 in the vicinity of the pedicle 2010 and attempt to identify an inner surface of the cortical surface or wall by the "feel" of the tip of the drill bit contacting the inner cortical surface. Once the surgeon senses contact with the inner wall of the cortical bone 2006, the surgeon knows not to extend the drill any farther.

During a registration procedure, once cortical contact is achieved, the point of contact between the bone and the burr 2004 may be used to update the registration of the bone position. The surgeon may also update the screw insertion plan if needed. Registration improvement may be optimized by the load cell 2020 detecting the direction of the contact of the burr 2004 with the bone. The system may identify an error by comparing the contact position with the anticipated contact based upon the surgical navigation system tracking the position of the burr 2004 with respect to the registered position of the patient. If there is a difference, the registration could be updated using the contact point as an internal registration point.

Figure 20B:
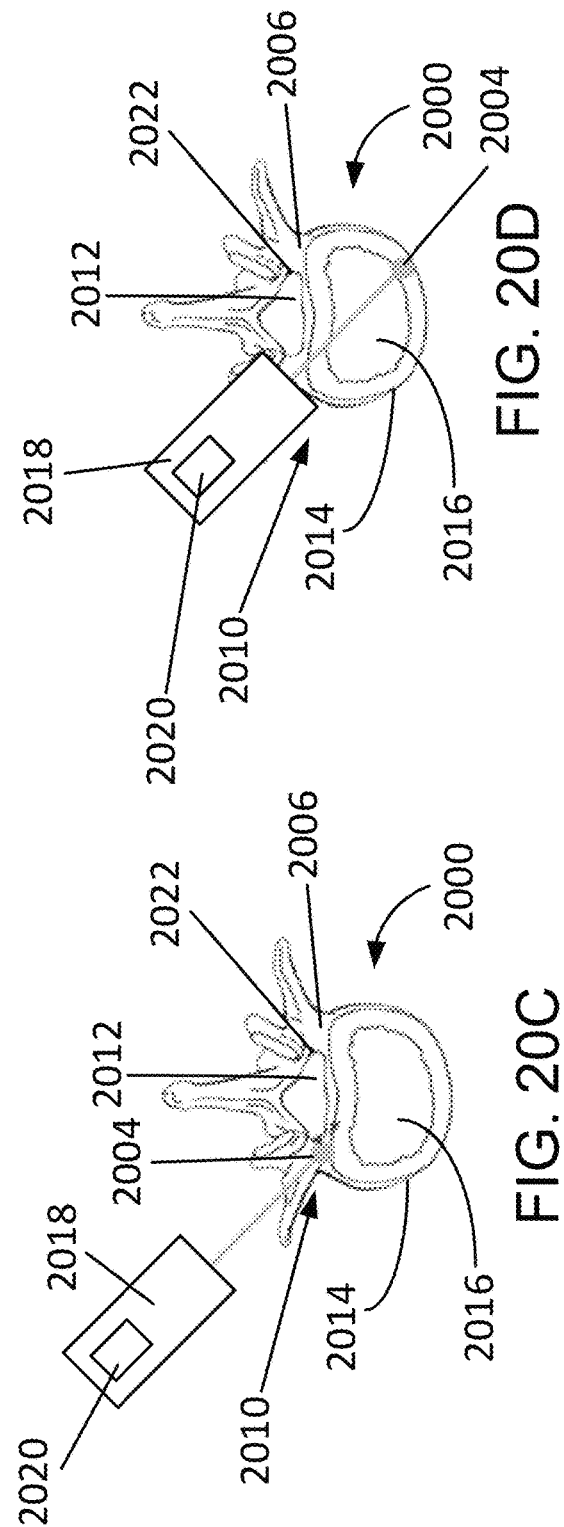
FIG. 20B is an axial cross-section image of a vertebra with a burr positioned within a neck region of the pedicle.
Figure 20C:
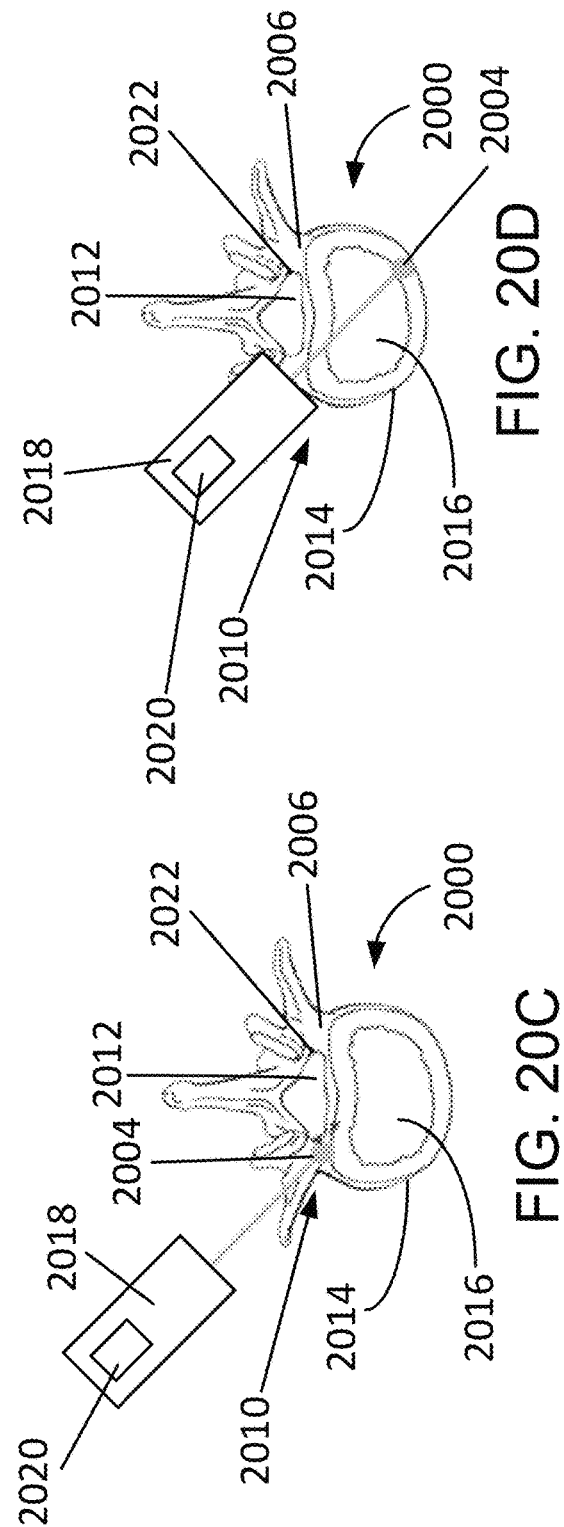
FIG. 20C is an axial cross-section image of a vertebra with a burr positioned within a neck region of the pedicle.
Figure 20D:
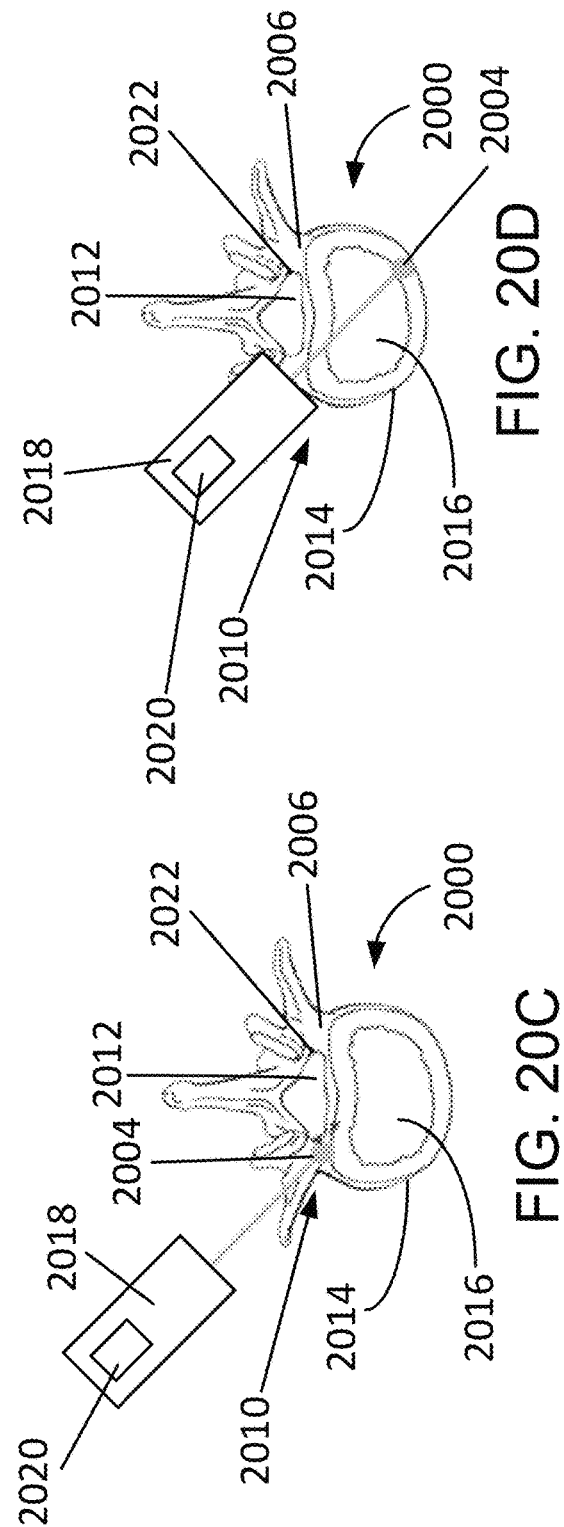
FIG. 20D is an axial cross-section image of a vertebra with a burr positioned through a neck region of the pedicle to a far inner cortical wall.

FIGS. 20B-20D illustrate a system and method of registering a vertebra 2000 using a burr 2004 of an end effector 2018 of surgical robotic system (not shown in FIGS. 20B-20D, but as shown and described in this application). Generally, the burr 2004 may be used to create a pathway into the pedicle 2010. Once inside the bone, the burr 2004 may be shut off so as to cease rotating. The surgeon may advance the burr 2004 through the cancellous bone 2016. A load cell 2020 on the end effector 2018 would be able to indicate if the burr 2004 contacts cortical bone 2006. The load cell 2020 may be configured so as to identify and distinguish cancellous bone 2016 from cortical bone 2006 as each bone type has a different stiffness. The load cell 2020 may audibly or otherwise (visually, haptic) signal the burr's 2004 contact with the cortical bone 2006. With a haptic setting, the surgical robotic system may prevent the surgeon from extending the burr 2004 further in a direction of the cortical bone 2006 once a certain stiffness value is reached.

As seen in FIG. 20B, the surgeon may insert the burr 2004 into the pedicle 2010 into the smallest neck region between the cortical bone 2006 around the spinal cord 2012 and the cortical canal 2022 around the exterior of the vertebra 2000. The burr 2004 may be moved from side-to-side (as indicated by the arrows in FIG. 20B) to intentionally contact the cortical walls 2006 and register the internal features thereof. The burr 2004 may be pivoted about the entry point in order to minimize any disruption of screw thread purchase areas.

As seen in FIG. 20C, the surgeon may insert the burr 2004 into the pedicle 2010 into the smallest neck region between the cortical bone 2006 around the spinal cord 2012 and the cortical con around the exterior of the vertebra 2000. The burr 2004 may be moved (as indicated by the arrows in FIG. 20C) over the internal surface of the cortical canal 2022 to map out or create a registration surface thereon. The identified surface on the cortical con may then be compared with the model to improve or adjust registration.

As seen in FIG. 20D, the surgeon may insert the burr 2004 through the pedicle 2010 and through the cancellous bone 2016 until the burr 2004 contacts a far inner surface of the cortical rim 2014. If there were no contacts with the burr 2004 against the cortical bone 2006 of the neck region of the pedicle 2012, contact with the inner surface of the cortical rim 2014 would be confirmed. When the load cell 2020 detects the far cortex, then the system may indicate such contact and the registration may be updated or improved accordingly.

In addition to the system detecting when the burr 2004 contacts the cortical bone 2006, the system may also detect potential breaches of the cortical bone 2006. For example, once the burr 2004 contacts the cortical bone 2006, as determined by the load experienced by the load cell 2020 of the end effector 2018, any loads experienced at that boundary wall that vary from the previous loads (e.g., a sudden decrease in resistance/stiffness indicating a break though of the cortical wall) may be considered potential breaches of the cortical surface 2006.

In certain instances, a system and method of surgical registration may be as follows. A system may register patient data gathered intra-operatively of a vertebra 2000 with a computer model of the vertebra in a coordinate system. The vertebra 2000 may include a cortical bone shell 2006 having an outer surface and an inner surface, and cancellous bone interior 2016 of the cortical bone shell 2006. The vertebra 2000 may define a spinal cord canal 2022 bounded by the cortical bone shell 2006. In certain instances, the system may include a surgical navigation system, and at least one computing device. The surgical navigation system may include a tracking device and at least one tool 2018 that is tracked by the tracking device. The at least one tool may include an end effector 2018 having a cutting element 2004 at a distal end thereof, and a load cell 2018 to sense a load on the cutting element 2004. The computing device may be in communication with the surgical navigation system. And the at least one computing device may store the computer model of the vertebra in the coordinate system.

In certain instances, the at least one computing device may receive load data associated with a load experienced by the cutting element 2004 at the distal end of the end effector 2018 when the cutting element 2004 contacts the cortical bone shell 2006 and the cancellous bone 2016. The at least one computing device may also identify, based on the load data, when the cutting element 2004 contacts the inner surface of the cortical bone shell 2006. The at least one computing device may also receive a point-cloud of data associated with the vertebra 2000. The point-cloud of data may include coordinate locations on the inner surface of the cortical bone shell 2006 that are collected via the cutting element 2004. The at least one computing device may also run or update a transform to register the point-cloud of data associated with the vertebra 2000 to the computer model of the vertebra in a common coordinate system.

VI. Example Computing System

Figure 21:
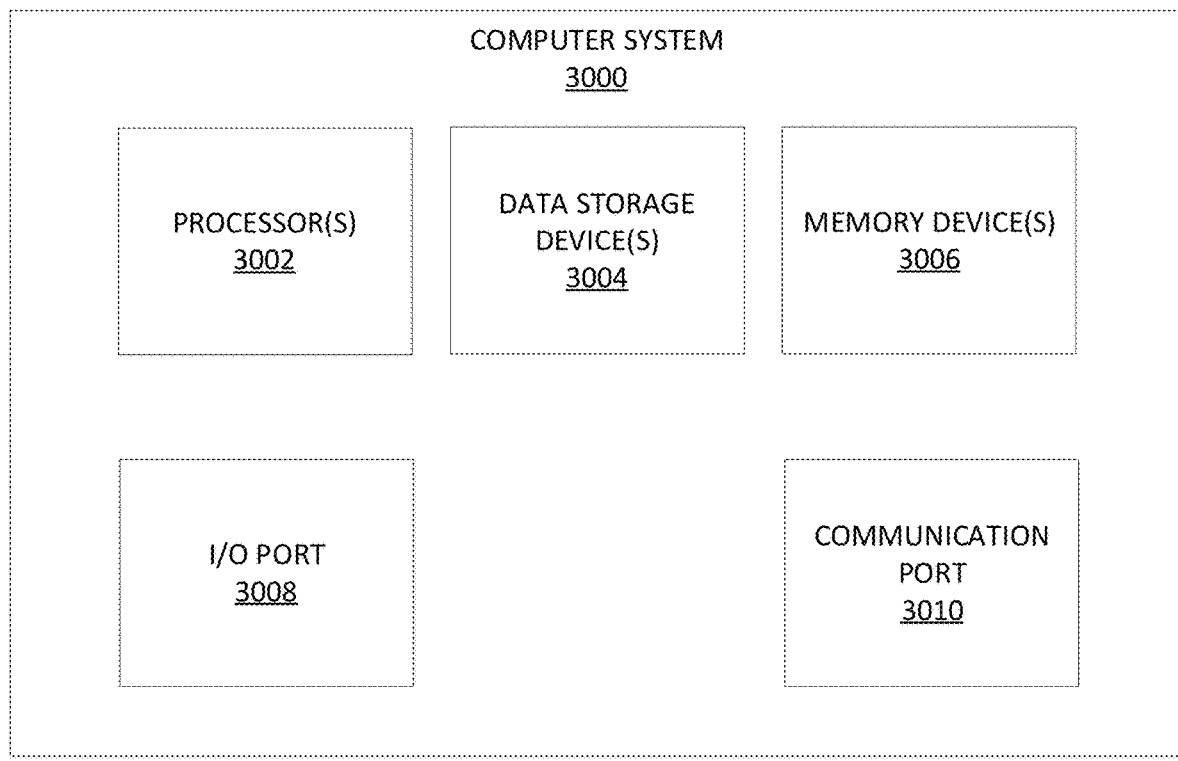
FIG. 21 is an example computing system having one or more computing units that may implement various systems and methods discussed herein is provided.

Referring to FIG. 21, a detailed description of an example computing system 3000 having one or more computing units that may implement various systems and methods discussed herein is provided. The computing system 3000 may be applicable to any of the computers or systems utilized in the preoperative or intra-operative planning of the arthroplasty procedure (e.g., registration), and other computing or network devices. It will be appreciated that specific implementations of these devices may be of differing possible specific computing architectures not all of which are specifically discussed herein but will be understood by those of ordinary skill in the art.

The computer system 3000 may be a computing system that is capable of executing a computer program product to execute a computer process. Data and program files may be input to the computer system 3000, which reads the files and executes the programs therein. Some of the elements of the computer system 3000 are shown in FIG. 21, including one or more hardware processors 3002, one or more data storage devices 3004, one or more memory devices 3008, and/or one or more ports 3008-3010. Additionally, other elements that will be recognized by those skilled in the art may be included in the computing system 3000 but are not explicitly depicted in FIG. 21 or discussed further herein. Various elements of the computer system 3000 may communicate with one another by way of one or more communication buses, point-to-point communication paths, or other communication means not explicitly depicted in FIG. 21.

The processor 3002 may include, for example, a central processing unit (CPU), a microprocessor, a microcontroller, a digital signal processor (DSP), and/or one or more internal levels of cache. There may be one or more processors 3002, such that the processor 3002 comprises a single central-processing unit, or a plurality of processing units capable of executing instructions and performing operations in parallel with each other, commonly referred to as a parallel processing environment.

The computer system 3000 may be a conventional computer, a distributed computer, or any other type of computer, such as one or more external computers made available via a cloud computing architecture. The presently described technology is optionally implemented in software stored on the data stored device(s) 3004, stored on the memory device(s) 3006, and/or communicated via one or more of the ports 3008-3010, thereby transforming the computer system 3000 in FIG. 21 to a special purpose machine for implementing the operations described herein. Examples of the computer system 3000 include personal computers, terminals, workstations, mobile phones, tablets, laptops, personal computers, multimedia consoles, gaming consoles, set top boxes, and the like.

The one or more data storage devices 3004 may include any non-volatile data storage device capable of storing data generated or employed within the computing system 3000, such as computer executable instructions for performing a computer process, which may include instructions of both application programs and an operating system (OS) that manages the various components of the computing system 3000. The data storage devices 3004 may include, without limitation, magnetic disk drives, optical disk drives, solid state drives (SSDs), flash drives, and the like. The data storage devices 3004 may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 3006 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in the data storage devices 3004 and/or the memory devices 3006, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computer system 3000 includes one or more ports, such as an input/output (I/O) port 3008 and a communication port 3010, for communicating with other computing, network, navigation, or robotic devices. It will be appreciated that the ports 3008-3010 may be combined or separate and that more or fewer ports may be included in the computer system 3000.

The I/O port 3008 may be connected to an I/O device, or other device, by which information is input to or output from the computing system 3000. Such I/O devices may include, without limitation, one or more input devices, or output devices, such as, for example, robotic arms, and navigation and tracking systems.

In one implementation, the input devices convert a human-generated signal, such as, human voice, physical movement, physical touch or pressure, and/or the like, into electrical signals as input data into the computing system 3000 via the I/O port 3008. Similarly, the output devices may convert electrical signals received from computing system 3000 via the I/O port 3008 into signals that may be sensed as output by a human, such as sound, light, and/or touch. The input device may be an alphanumeric input device, including alphanumeric and other keys for communicating information and/or command selections to the processor 3002 via the I/O port 3008. The input device may be another type of user input device including, but not limited to: direction and selection control devices, such as a mouse, a trackball, cursor direction keys, a joystick, and/or a wheel; one or more sensors, such as a camera, a microphone, a positional sensor, an orientation sensor, a gravitational sensor, an inertial sensor, and/or an accelerometer; and/or a touch-sensitive display screen ("touchscreen"), and/or tracking/probe devices associated with the navigation and tracking systems. The output devices may include, without limitation, a display, a touchscreen, a speaker, a tactile and/or haptic output device, and/or the like. In some implementations, the input device and the output device may be the same device, for example, in the case of a touchscreen.

In one implementation, a communication port 3010 is connected to a network by way of which the computer system 3000 may receive network data useful in executing the methods and systems set out herein as well as transmitting information and network configuration changes determined thereby. Stated differently, the communication port 3010 connects the computer system 3000 to one or more communication interface devices configured to transmit and/or receive information between the computing system 3000 and other devices by way of one or more wired or wireless communication networks or connections. Examples of such networks or connections include, without limitation, Universal Serial Bus (USB), Ethernet, Wi-Fi, Bluetooth®, Near Field Communication (NFC), Long-Term Evolution (LTE), and so on. One or more such communication interface devices may be utilized via the communication port 3010 to communicate one or more other machines, either directly over a point-to-point communication path, over a wide area network (WAN) (e.g., the Internet), over a local area network (LAN), over a cellular (e.g., third generation (3G) or fourth generation (4G)) network, or over another communication means. Further, the communication port 3010 may communicate with an antenna or other link for electromagnetic signal transmission and/or reception.

In an example implementation, patient data, bone models (e.g., generic, patient specific), transformation software, tracking and navigation software, registration software, and other software and other modules and services may be embodied by instructions stored on the data storage devices 3004 and/or the memory devices 3006 and executed by the processor 3002. The computer system 3000 may be integrated with or otherwise form part of the surgical system 100. The system may be configured for registering patient data gathered intra-operatively from a first bone with a computer model of the first bone in a common coordinate system. The first bone may joint a second bone to form a joint such as, for example, a hip joint, a knee joint, a shoulder joint, an elbow joint, or ankle joint, among others. The system may include a surgical navigations system including a tracking device and a tool (e.g., navigation probe, end of a surgical robotic arm) to be tracked in its movement by the tracking device. Additionally, the system may include a computing device (one or more) in communication with the navigation system. The computing device may perform the following steps: 1) receive first data points of the patient data from first intra-operatively collected points on an articular surface of the concave portion of the bone. The first data points may be collected using the at least one tool. The first data points may correspond in location to a first articular region on the computer model. 2) receive a second data point from a second intra-operatively collected point on the first bone. The second data point may be collected using the at least one tool. The second data point may correspond in location to a second virtual data point on the computer model. 3) determine an intra-operative center of rotation from the first data points. The intra-operative center of rotation may correspond to a physical center of rotation of the second bone relative to the first bone. 4) compare a first distance between the virtual center of rotation and the second virtual data point and a second distance between the intra-operative center of rotation and the second data point. And, 5) run a transformation with the patient data and the computer model so as to have them correspond with respect to position and orientation.

The system set forth in FIG. 21 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized.

In the present disclosure, the methods disclosed herein, for example, those shown in FIG. 5, among others, may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure including any of the methods described herein may be provided as a computer program product, software, or computerized method that may include a non-transitory machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium, optical storage medium; magneto-optical storage medium, read only memory (ROM); random access memory (RAM); erasable programmable memory (e.g., EPROM and EEPROM); flash memory; or other types of medium suitable for storing electronic instructions.

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow. For example, while the description discusses methods involving the hip, the disclosure is similarly applicable to other joints including the shoulder, ankle, and spine, among others.

In general, while the embodiments described herein have been described with reference to particular embodiments, modifications can be made thereto without departing from the spirit and scope of the disclosure. Note also that the term "including" as used herein is intended to be inclusive, i.e. "including but not limited to."

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A system for registering patient data gathered intra-operatively of a vertebra with a computer model of the vertebra in a coordinate system, the vertebra comprising a cortical bone shell, the cortical bone shell having an outer surface and an inner surface, and a cancellous bone interior, the system comprising:
   a) a surgical navigation system comprising a tracking device and at least one tool configured to be tracked in its movement by the tracking device, the at least one tool comprising an end effector having a cutting element at a distal end thereof, and a load cell configured to sense a load on the cutting element; and
   b) at least one computing device in communication with the surgical navigation system, the at least one computing device storing the computer model of the vertebra in the coordinate system, the at least one computing device:
      i) receiving load data associated with the load on the cutting element at the distal end of the end effector when the cutting element is within the cancellous bone interior of the cortical bone shell;
      ii) identifying, based on the load data, when the cutting element contacts the inner surface of the cortical bone shell;
      iii) receiving a point-cloud of data associated with the vertebra, the point-cloud of data comprising coordinate locations on the inner surface of the cortical bone shell, the point-cloud of data being collected via the cutting element at the distal end of the end effector; and
      iv) at least one of running or updating a transform to register the point-cloud of data associated with the vertebra to the computer model of the vertebra in a common coordinate system.

2. The system of claim 1, wherein the surgical navigation system is configured to provide a signal based on the load data.

3. The system of claim 2, wherein the signal comprises one or more of an audible signal, a visual signal, and a haptic signal.

4. The system of claim 1, wherein the at least one computing device is further configured for identifying, based on the load data, a potential breach of the cortical bone shell.

5. The system of claim 4, wherein the potential breach is identified when the load on the cutting element along the inner surface of the cortical bone shell varies from previous loads along the inner surface of the cortical bone shell.

6. The system of claim 1, wherein the cutting element is configured to cut the outer surface of the cortical bone shell.

7. The system of claim 6, wherein the at least one computing device is further configured for receiving additional load data associated with the load on the cutting element when the cutting element is cutting the outer surface of the cortical bone shell.

8. The system of claim 7, wherein the at least one computing device is further configured for identifying, based on the additional load data, when the cutting element contacts the cancellous bone interior.

9. The system of claim 8, wherein the at least one computing device is further configured for shutting off the cutting element when the cutting element contacts the cancellous bone interior.

10. The system of claim 1, wherein the at least one computing device is further configured for receiving additional load data associated with the load on the cutting element.

11. The system of claim 10, wherein the at least one computing device is further configured for identifying, based on the additional load data, a stiffness of a bone in contact with the cutting element.

12. The system of claim 11, wherein the at least one computing device is further configured for determining when the stiffness of the bone in contact with the cutting element meets or exceeds a threshold stiffness.

13. The system of claim 1, wherein the point-cloud of data is collected by the cutting element along a path.

14. The system of claim 13, wherein the path includes a side-to-side path within the cortical bone shell, a linear path within the cortical bone shell, and/or a pivoting path within the cortical bone shell.

15. The system of claim 10, wherein the cutting element comprises a burr.

16. The system of claim 1, wherein the load data is collected while the cutting element is in operation.

17. The system of claim 1, wherein the load data is collected while the cutting element is not in operation.

* * * * *